US008735620B2

(12) United States Patent
Sirigireddy

(10) Patent No.: US 8,735,620 B2
(45) Date of Patent: May 27, 2014

(54) PROCESSES FOR PREPARING (E)-STYRYLBENZYLSULFONE COMPOUNDS AND USES THEREOF FOR TREATING PROLIFERATIVE DISORDERS

(75) Inventor: Reddy Sirigireddy, Andhra Prdesh (IN)

(73) Assignee: EPR Pharmaceuticals PVT. Ltd, Hyderabad (IN)

( * ) Notice: Subject to any disclaimer, the term of this patent is extended or adjusted under 35 U.S.C. 154(b) by 768 days.

(21) Appl. No.: 12/337,121

(22) Filed: Dec. 17, 2008

(65) Prior Publication Data

US 2010/0152491 A1 Jun. 17, 2010

(51) Int. Cl.
*C07F 9/12* (2006.01)
(52) U.S. Cl.
USPC .......................................................... 558/92
(58) Field of Classification Search
CPC ...................................................... C07F 9/12
See application file for complete search history.

(56) References Cited

U.S. PATENT DOCUMENTS

| | | | | |
|---|---|---|---|---|
| 6,486,210 | B2 * | 11/2002 | Reddy et al. | 514/708 |
| 6,833,480 | B2 | 12/2004 | Reddy et al. | |
| 2008/0058290 | A1 | 3/2008 | Reddy et al. | |
| 2008/0095866 | A1 * | 4/2008 | Declercq et al. | 424/729 |

FOREIGN PATENT DOCUMENTS

WO  WO 2005089269  *  9/2005

OTHER PUBLICATIONS

Reddy et al, {Design, Synthesis, and Biological Evaluation of E)-Styrylbenzylsulfones as Novel Anticancer Agents, Journal of Medicinal Chemistry (2008), 51(1), 86-100}.*
Reddy M .V. R.; Reddy, S. Synthesis of α, β-Unsaturated Suflones. *Acta Chim.Hung.* 1984, 115, 269-271.
Morgan, D. O. Cyclin-dependent kinases: Engines, Clocks, and Microprocessors. *Annu Rev Cell Dev Biol.* 1997, 13, 261-291.
Soldani, C.; Scovassi, A. I. Poly (ADP-ribose) polymerase-1 cleavage during apoptosis: an update. *Apoptosis* 2002, 7, 321-328.
Sherr, C.J.; McCormick, F. The Rb and p53 pathways in cancer. *Cancer Cell* 2002, 2, 103-112.
Harker, W. G.; Sikic, B. I. Multidrug (pleiotropic) resistance in doxorubicin selected variants of the human sarcoma cell line MES-SA. *Cancer Res.* 1985, 45, 4091-4096.
Fujimori, A.; Arker, W. G.; Kohlhagen, G.; Hoki, Y.; Pommier, Y. Mutation at the catalytic site of topoisomerase 1 in CEM/C2, a human leukemia cell line resistant to camptothecin. *Cancer Res.* 1995, 55, 1339-1346.

Hunter, T. Oncoprotein Networks. Cell 1997, 88, 333-346.
Blagosklonny, M. V.; Pardee, A. B. The Restriction Point of the Cell Cycle. *Cell Cycle* 2002, 1, 103-105.
Donjerkovic, D.; Scott, D. W. Regulation of the G1 phase of the mammalian cell cycle. Cell Res. 2000, 10, 1-16.
Pettit, G. R.; Lippert, J. W. Antineoplastic Agents. 429. Synthesis of the combretastatin A-1 and combretastatin B-1 prodrugs. *Anti-Cancer drug. Des.* 2000, 15, 203-216.
Pettit, G. R.; Grealish, M. P.; Jung, K.; Hamel, E.; Pettit, R. K.; Chapuis, J-C.; Schmidt, J.M. Antineoplastic Agents. 465. Structural Modification of Resveratrol: Sodium Resverastatin Phosphate1. *J. Med. Chem.* 2002, 45, 2534-2542.
Corey, E. J.; Venkateswarulu, A. Protection of hydroxyl groups as tert-butyldimethylsilyl derivatives. *J. Am. Chem. Soc.* 1972, 94, 6190-6191.
Reddy, M. V. Ratnana Reddy, Muralidhat R. Mallireddigari, Stephen C. Cosenza, Venkat R. Pallela, Nabisa M. Iqbal, Kimberly A. Robell, Anthony D. Kang, and E. Premkumar Reddy; Design, Synthesis, and Biological Evaluation of (*E*)-Styrylbenzylsulfones as Novel Anticancer Agents. *J. Med. Chem.* 2008, 51, 86-100.
Wolfrom, M. L.; Koos, E. W.; Bhat, H. B. Osage orange pigment. XV111. Synthesis of osajaxanthone. *J. Org. Chem.* 1967, 32, 1058-1060.
Kendall, P. M.; Johnson, J.V.; Cook, C. E. Synthetic route to an aromatic analog of strigol. *J. Org. Chem.* 1979. 44, 1421-1424.
Ronald, R.C.; Lansinger, T. S.; Lillie, T. S.; Wheeler, C. J. Total synthesis of frustulosin and aurocitrin. *J. Org. Chem.* 1982, 47, 2541-2549.
Adrian L. Schwan et al., 1 Alkenesulfinyl Chlorides: Synthesis, Characterization, and Some Substitution Reactions. *J. Org. Chem.* 1998, 63, 7825-7832.
Malumbres, M.; Barbacid, M. To cycle or not to cycle: A critical decision in cancer. *Nat. Rev. Cancer* 2001, 1, 222-231.
Park, I.W.; Reddy, M. V. R.; Reddy, E. P.; Groopman, J. E. Evaluation of novel cell cycle inhibitors in mantle cell lymphoma. *Oncogene* 2007, 26, 5635-5642.
Reddy, M. V. R.; Reddy, S.; Reddy, D. B. Facile method for the synthesis of 2-(arylsulfony1)-1-phenyl-3-aryl-2-propen-1-ones. *Sulfur Lett.* 1987, 7, 43-48.
Diczfalusy et al., Acta Chem Scand, 7, 913, 1953.
Baumann, Polyphenols Everywhere, Skin & Allergy News, Jan. 4, 2010.
Houben-Weyl, Methoden der Organischen Chemie (Methods in Organic Chemistry)-Vierte Auflage (Fourth Edition), Band XII (vol. 12), Teil 2 (Part 2), p. 172-175.

* cited by examiner

*Primary Examiner* — Paul A Zucker
(74) *Attorney, Agent, or Firm* — Houri Kalilian; Law Offices of Khalilian Sira, LLC

(57) ABSTRACT

Processes for preparing (E)-2,4,6-(Trimethoxystyryl)-3-O-Phosphate Disodium-4-Methoxybenzyl Sulfones and uses thereof as antiproliferative agents, including, for example, anticancer agents, and as radioprotective and chemoprotective agents.

9 Claims, 4 Drawing Sheets
(3 of 4 Drawing Sheet(s) Filed in Color)

A

B

PROCESSES FOR PREPARING (E)-STYRYLBENZYLSULFONE COMPOUNDS AND USES THEREOF FOR TREATING PROLIFERATIVE DISORDERS

FIELD OF THE INVENTION

The invention relates to methods for preparing (E)-styrylbenzylsulfone compounds. The invention further relates to methods for use of such (E)-styrylbenzylsulfone compounds in the treatment of proliferative disorders, and protection from the cytotoxic effects of ionizing radiation and of cytotoxic chemotherapeutic agents.

BACKGROUND OF THE INVENTION

Cancer is now believed to result from unlimited growth of a given cell, which is often due to a block in the ability of cells to undergo differentiation and/or apoptosis. Most of our understanding of how cells grow and divide comes from the study of cells grown in vitro. The cell cycle is typically divided into four phases, G1, S, G2 and M. The periods associated with DNA synthesis (S phase) and mitosis (M phase) are separated by gaps called G1 and G2 (Malumbres, M.; Barbacid, M. *Nat. Rev. Cancer* 2001, 1, 222-231; Sherr, C. J.; McCormick, F. Cancer Cell 2002, 2, 103-112; Grana, X,; Reddy, E. P. Oncogene 1995, 11, 211-219). The last two decades have seen a series of discoveries, which have provided us with a better understanding of the complexity of the control mechanisms, which ensure ordered progression of cell cycle. It is becoming apparent that the order and timing of the cell cycle is critical for accurate transmission of genetic information, and consequently a number of biochemical pathways have evolved to ensure that initiation of a particular cell cycle event is dependent on the accurate completion of the others. These biochemical pathways have been termed 'Checkpoints.'

Most normal cells, unless they have received a stimulus to proliferate or differentiate, remain in a resting state, termed $G_o$. However, when the organism requires additional cells, extracellular stimuli induce the cells to enter the $G_1$ phase of the cell cycle and become committed to cell division. It is at a late point in the $G_1$ phase of the cell cycle that a potentially dividing cell reaches the "restriction point," a time at which the cell must determine whether the conditions are suitable for continued proliferation (Blagosklonny, M. V.; Pardee, A. B. Cell Cycle 2002, 1, 103-105; Donjerkovic, D.; Scott, D. W. Cell Res. 2000, 10, 1-16; O'Connor, P. M. Cancer Surv. 1997, 29, 151-182). Provided that conditions are conducive to proliferation, the cell proceeds past this checkpoint. An absolute prerequisite for cell growth is the duplication of its genetic material, which occurs during the S phase. Once the DNA has been replicated, the cell "ascertains" whether this process has been correctly executed during the second checkpoint during $G_2$, and provided that it has, the cell divides during mitosis, or M phase (Millard, S. S.; Kof, A. J. Cell Biochem. 1998, suppl. 30-31, 37-42). The ordered growth process seen in normal cells is a result of regulatory control mechanisms that restrain cell cycle machinery. The genetic changes seen in a malignant cell are primarily aimed at overriding this negative regulation and result in the loss of one or both of the intrinsic checkpoints that are normally used by their normal counterparts. While some of the oncogenes, such as ras, force progression through $G_1$, other genes such as Rb, which are termed tumor suppressor genes, function as "gatekeepers" of these restriction points (Mc Donald, E. R.; El-Diery, W. S. Ann. Med. 2001, 33, 113-122; Ewen, M. E. Prog. Cell Cycle Res. 2000, 4, 1-17). Cancer is characterized by a loss of one or more tumor suppressor genes, which enables a malignant cell to ignore all of the safeguards that are aimed at preventing unwanted cell division.

An important rule associated with cell cycle progression (for both normal and tumor cells) is the fact that once a cell crosses the "restriction point" (which is the G1/S boundary), it has to either divide into two daughter cells or die[4] due to the fact that most eukaryotic cells can exist in S, G2 and M phases of the cell cycle for only a limited span of time. Most chemotherapeutic agents, such as paclitaxel, that are currently used in cancer therapy function by blocking cell cycle progression at a point beyond $G_1/S$ boundary (M phase in the case of paclitaxel), resulting in the death of the tumor cell (Wang, T.; Wang, H.; Soong, Y. 88, 2619-2628). A major problem with many of the current drugs is their inability to discriminate between normal and tumor cells. As a result, normal cells undergoing active cell division also become blocked at the mitotic phase of the cell cycle and enter programmed cell death pathways, the effects of which are often manifested as the toxic side-effects seen in patients treated by these drugs. A second problem appears to be the development of resistance to many of the chemotherapeutic agents often due to over-expression of drug transporters. Our quest was to design new chemical entities that exhibit reduced toxicity in normal cells and are not recognized by drug transporters that are over-expressed in drug-resistant tumor cells.

What are needed are methods of preparing effective anti-proliferative, radioprotective and chemoprotective activity agents. The methods and compositions of the present invention satisfy these and other long felt needs with the following invention that provides the synthesis of a group of styryl benzyl sulfones which induce apoptotic death of a wide variety of human tumor cell lines at sub nanomolar concentrations while exhibiting relatively low toxicity to normal human cells. More importantly, compounds prepared by these methods were found to be active against a wide variety of human tumor cell lines that are resistant to the activity of many of the cytotoxic agents.

SUMMARY OF THE INVENTION

In one aspect of the invention, compounds, processes, pharmaceutical compositions and therapeutic methods are provided. The biologically active compounds are in the form of aromatic olefins, structurally linked via an optionally substituted methylene sulfone, an optionally substituted methylene sulfoxide, an optionally N-substituted sulfonamide, or an optionally N-substituted carboxamide linker, to a phenol or thiophenol functionality, or a derivative of such a phenol or thiophenol functionality.

According to one aspect of the invention, processes for preparing compounds according to Formula I are provided,

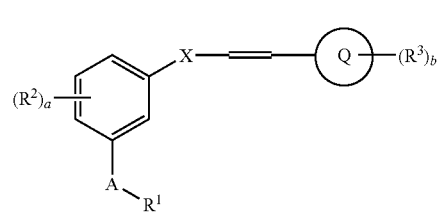

I wherein,

A is —S— or —O—;

$R^1$ is selected from the group consisting of —H; halo($C_1$-$C_6$)alkyl, preferably trifluoro($C_1$-$C_6$)alkyl, difluoro($C_1$-$C_6$)

alkyl and chloro($C_1$-$C_6$)alkyl more preferably trifluoro($C_1$-$C_3$)alkyl, difluoro($C_1$-$C_3$)alkyl and chloro($C_1$-$C_3$)alkyl, most preferably —$CF_3$, —$CHF_2$ and —$CH_2Cl$; —C(=O)$R^w$; —S(=O)$R^w$; —$SO_2R^w$; —($C_1$-$C_6$ hydrocarbylene)$R^z$, preferably —($C_1$-$C_6$)alkylene$R^z$, more preferably —($C_1$-$C_6$) alkylene-CO$R^y$; —P(=O)(O$R^v$)$_2$; —C($R^a$)($R^v$)—C(=O)— $R^n$; substituted and unsubstituted aryl, preferably substituted and unsubstituted phenyl; substituted and unsubstituted heteroaryl, preferably substituted and unsubstituted monocyclic heteroaryl; —Si[($C_1$-$C_6$)alkyl]$_3$, preferably, —Si($CH_3$)$_2$—C($CH_3$)$_3$ (tert-butyldimethylsilyl); and —$CH_2CH_2$Si[($C_1$-$C_6$)alkyl]$_3$, preferably —$CH_2CH_2$Si($CH_3$)$_2$—C($CH_3$)$_3$ and —$CH_2CH_2$Si($CH_3$)$_3$;

each $R^v$ is independently selected from the group consisting of —H and —($C_1$-$C_7$)hydrocarbyl, preferably —($C_1$-$C_6$) alkyl, more preferably —($C_1$-$C_3$)alkyl, most preferably —$CH_3$ or —$C_2H_5$;

$R^w$ is selected from the group consisting of —($C_1$-$C_7$) hydrocarbyl, preferably —($C_1$-$C_6$)alkyl, more preferably —($C_1$-$C_3$)alkyl, most preferably —$CH_3$ or —$C_2H_5$; —$NR^v_2$; —O$R^v$; halo($C_1$-$C_3$ alkyl), preferably chloro($C_1$-$C_3$ alkyl) and trifluoro($C_1$-$C_3$ alkyl); —$NR^vCR^vR^a$—C(=O)—$R^n$; —$CR^vR^a$—N($R^v$)—$R^c$; substituted and unsubstituted aryl, preferably substituted and unsubstituted phenyl; substituted and unsubstituted aryl($C_1$-$C_3$)alkyl, preferably substituted and unsubstituted phenyl($C_1$-$C_3$)alkyl; substituted and unsubstituted heteroaryl, preferably substituted and unsubstituted monocyclic heteroaryl; substituted and unsubstituted heteroaryl($C_1$-$C_3$)alkyl, preferably substituted and unsubstituted monocyclic heteroaryl($C_1$-$C_3$)alkyl; substituted and unsubstituted heterocyclyl; substituted and unsubstituted heterocyclyl($C_1$-$C_3$)alkyl; —($C_1$-$C_3$ alkylene)P(=O)(O$R^v$)$_2$; —($C_1$-$C_3$)perfluoroalkylene-N($CH_3$)$_2$; —($C_1$-$C_3$)alkylene-$N^+$($C_1$-$C_3$)$_3$; —($C_1$-$C_3$)alkylene-$N^+$($CH_2CH_2OH$)$_3$; —($C_1$-$C_4$alkylene)-C(=O)-halogen; —($C_1$-$C_4$)perfluoroalkylene-$CO_2R^v$; —($C_1$-$C_3$alkylene)C(=O)O$R^v$; and —($C_1$-$C_3$alkylene)OC(=O)—($C_1$-$C_3$ alkylene)C(=O)$R^v$;

$R^y$ is selected from the group consisting of —O$R^v$, —$NR^v_2$ and —($C_1$-$C_6$)alkyl;

$R^z$ is selected from the group consisting of —C(=O)$R^y$; —$NR^vCR^vR^a$—C(=O)—$R^n$; —$NR^v_2$; —O$R^v$; substituted and unsubstituted aryl, preferably substituted and unsubstituted phenyl; substituted and unsubstituted heteroaryl, preferably substituted and unsubstituted monocyclic heteroaryl; and —C(=O)($C_1$-$C_3$)alkyl;

each $R^a$ is independently selected from the group consisting of —H; —($C_1$-$C_6$)alkyl; —($C_1$-$C_6$)heteroalkyl, particularly —$CH_2SH$, —($CH_2$)$_2$C(=O)—$NH_2$, —$CH_2$—OH, —CH(OH)—$CH_3$, —($CH_2$)$_4$—$NH_2$, and —($CH_2$)$_2$—S—$CH_3$; —($CH_2$)$_3$—NH—C($NH_2$)(=NH); —$CH_2$C(=O)$NH_2$; —$CH_2COOH$; —($CH_2$)$_2COOH$; substituted and unsubstituted aryl, preferably substituted and unsubstituted phenyl; substituted and unsubstituted aryl($C_1$-$C_3$)alkyl, preferably substituted and unsubstituted phenyl($C_1$-$C_3$)alkyl, more preferably substituted and unsubstituted benzyl, particularly 4-hydroxybenzyl; substituted and unsubstituted heterocyclyl, preferably substituted and unsubstituted heteroaryl, particularly —$CH_2$-(3-indolyl), more preferably substituted and unsubstituted monocyclic heteroaryl; and substituted and unsubstituted heterocyclyl($C_1$-$C_3$)alkyl, preferably substituted and unsubstituted heteroaryl($C_1$-$C_3$)alkyl, more preferably substituted and unsubstituted monocyclic heteroaryl($C_1$-$C_3$)alkyl, most preferably substituted and unsubstituted monocyclic heteroaryl-$CH_2$—, particularly —$CH_2$-inidazolyl;

each $R^n$ is independently selected from the group consisting of —O$R^v$, —$NR^v_2$, and an N-terminally linked peptidyl residue containing from 1 to 3 amino acids in which the terminal carboxyl group of the peptidyl residue is present as a functional group selected from the group consisting of —$CO_2R^v$ and —C(=O)$NR^v_2$;

each $R^c$ is independently selected from the group consisting of —H and a carboxy terminally linked peptidyl residue containing from 1 to 3 amino acids in which the terminal amino group of the peptidyl residue is present as a functional group selected from the group consisting of —$NH_2$; —NHC(=O)($C_1$-$C_6$)alkyl; —NH($C_1$-$C_6$)alkyl; —NH($C_1$-$C_6$ alkyl)$_2$ and —NHC(=O)O($C_1$-$C_7$)hydrocarbyl, preferably —NHC(=O)O($C_1$-$C_6$)alkyl and —NHC(=O)O-benzyl;

Q is aryl or heteroaryl;

each $R^2$ and $R^3$ are independently selected from the group consisting of halogen; —($C_1$-$C_7$)hydrocarbyl, preferably —($C_1$-$C_6$)alkyl, more preferably —($C_1$-$C_3$)alkyl, most preferably —$CH_3$ and —$C_2H_5$; —C(=O)$R^v$; —$NR^v_2$; —NHC(=O)$R^v$; —$NHSO_2R^v$; —$NHR^a$; —NHCR$^v$R$^a$C(=O)$R^n$; —$NHSO_2R^v$; —C(=O)O$R^v$; —C(=O)NH$R^v$; —$NO_2$; —CN; —O$R^v$; —P(=O)(O$R^v$)$_2$; —C(=NH)$NH_2$, dimethylamino($C_2$-$C_6$ alkoxy); —NHC(=$NR^v$)NH$R^v$; —($C_1$-$C_6$)haloalkyl, preferably trifluoro($C_1$-$C_6$)alkyl and difluoro($C_1$-$C_6$) alkyl, more preferably trifluoro($C_1$-$C_3$)alkyl and difluoro($C_1$-$C_3$)alkyl, most preferably —$CF_3$ and —$CHF_2$; and —($C_1$-$C_6$) haloalkoxy, preferably trifluoro($C_1$-$C_6$)alkoxy and difluoro($C_1$-$C_6$)alkoxy, more preferably trifluoro($C_1$-$C_3$)alkoxy and difluoro($C_1$-$C_3$)alkoxy, most preferably —$OCF_3$ and —$OCHF_2$;

wherein, the two $R^v$ groups on —P(=O)(O$R^v$)$_2$ and —$NR^v_2$ may optionally form a five- or six-membered heterocyclic ring, preferably a five-membered ring, which may further optionally be fused to an aryl or carbocyclic ring, preferably an aryl ring, more preferably a phenyl ring;

a is 0, 1, 2 or 3;

b is 0, 1, 2 or 3;

wherein the sum of a and b is preferably at least 1;

the conformation of the substituents on the exocyclic carbon-carbon double bond is either E- or Z-;

X is —C*H($R^x$)Y— or —$NR^x$—Z—;

Y is —S(=O)— or —$SO_2$—;

Z is —C(=O)— or —$SO_2$—;

$R^x$ is selected from the group consisting of —H; —($C_1$-$C_6$) alkyl, preferably —($C_1$-$C_3$)alkyl, more preferably methyl and ethyl; and —C(=O)($C_1$-$C_6$)alkyl, preferably —C(=O)($C_1$-$C_3$)alkyl, more preferably acetyl and propionyl; and

* indicates that, when $R^x$ is other than —H, the conformation of the substituents on the designated carbon atom is (R)-, (S)- or any mixture of (R)- and (S)-; or a salt of such a compound, preferably a pharmaceutically acceptable salt of such a compound;

provided that;

(a) when A is —O— and $R^1$ is —H;

b is greater than 0; and $R^3$ is other than ($C_1$-$C_6$)alkyl, —OH and —$NO_2$.

(b) when X is —$NR^x$—Z— and A is —O—;

$R^z$ is other than —C(=O)$R^y$, —$NR^v_2$ and unsubstituted aryl; and $R^w$ is other than —($C_1$-$C_6$)alkyl; and (c) when X is —C*H($R^x$)Y— and A is —O—;

$R^1$ is other than halo($C_1$-$C_6$)alkyl and unsubstituted aryl;

$R^z$ is other than —$NR^v_2$ and unsubstituted aryl; and $R^w$ is other than —($C_1$-$C_7$)hydrocarbyl.

According to some embodiments of compounds of Formula I, Q is aryl, preferably phenyl or naphthyl, more preferably phenyl.

According to other embodiments of compounds of Formula I, Q is heteroaryl, preferably monocyclic heteroaryl.

According to some embodiments of compounds of Formula I, there are provided compounds of Formula IE:

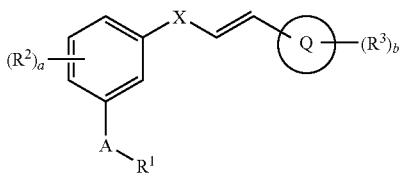

wherein the exocyclic carbon-carbon double bond is in the (E)-configuration.

According to some embodiments of compounds of Formula I, $R^1$ is —H.

According to other embodiments of compounds of Formula I, $R^1$ is other than —H.

Preferably, when one or more of Q, $R^1$, $R^w$, $R^a$ or $R^z$ is a monocyclic heteroaryl group, the monocyclic heteroaryl group is independently selected from the group consisting of pyridyl, pyrazinyl, pyrimidinyl, pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

More preferably, when one or more of Q, $R^1$, $R^a$, $R^w$ or $R^z$ is a monocyclic heteroaryl group, the monocyclic heteroaryl group is independently selected from the group consisting of pyridyl, thienyl, furyl, pyrrolyl, imidazolyl, thiazolyl, oxazolyl, pyrazolyl, and isothiazolyl.

Most preferably, when one or more of Q, $R^1$, $R^a$, $R^w$ or $R^z$ is a monocyclic heteroaryl group, the monocyclic heteroaryl group is independently selected from the group consisting of pyridyl, thienyl, and furyl.

Preferably, when one or more of Q, $R^1$, $R^a$, $R^w$ or $R^z$ is a heteroaryl group other than a monocycyclic heteroaryl group, the heteroaryl group is selected from the group consisting of indolyl, quinolyl, isoquinolyl, cinnolinyl, quinoxalinyl, quinazolinyl, phthalazinyl, 1,8-naphthyridinyl, 1,4-benzodioxanyl, coumarin, benzofuryl, 1,2-benzisoxazolyl, benzothienyl, benzoxazolyl, benzthiazolyl, purinyl, benzimidazolyl, benztriazolyl, thioxanthinyl, carbazolyl, carbolinyl, acridinyl, pyrrolizidinyl, and quinolizidinyl.

More preferably, when one or more of Q, $R^1$, $R^a$, $R^w$ or $R^z$ is a heteroaryl group other than a monocycyclic heteroaryl group, the heteroaryl group is selected from the group consisting of indolyl, quinolyl, isoquinolyl, benzofuryl, benzothienyl, benzoxazolyl, benzthiazolyl, and benzimidazolyl.

Most preferably, when one or more of Q, $R^1$, $R^a$, $R^w$ or $R^z$ is a heteroaryl group other than a monocycyclic heteroaryl group, the heteroaryl group is selected from the group consisting of indolyl, quinolyl, isoquinolyl, benzofuryl and benzothienyl.

Preferably, substituted aryl and heteroaryl rings in $R^1$, $R^a$, $R^w$ and $R^z$ groups are mono-, di- or tri-substituted, more preferably mono- or di-substituted by substituents selected from the group consisting of halogen; $(C_1-C_7)$hydrocarbyl, preferably benzyl and $(C_1-C_6)$alkyl, more preferably benzyl and $(C_1-C_3)$alkyl, most preferably benzyl, methyl and ethyl; —$NR^v_2$; —$NO_2$; —CN; heterocyclyl, preferably N-methylpiperazinyl, morpholinyl and thiomorpholinyl; —$OR^v$ and —$O(C_1-C_7)$hydrocarbyl, preferably —$O(C_1-C_6)$alkyl and —O-benzyl, more preferably —$O(C_1-C_3)$alkyl, most preferably benzyl, methoxy and ethoxy.

More preferably, substituted aryl and heteroaryl rings in $R^1$, $R^a$, $R^w$ and $R^z$ groups are mono-, di- or tri-substituted, more preferably mono- or di-substituted by substituents selected from the group consisting of chloro; fluoro; bromo; —$(C_1-C_6)$alkyl, more preferably —$(C_1-C_3)$alkyl, most preferably methyl and ethyl; —$NH_2$; —$NO_2$; —CN; heterocyclyl, preferably N-methylpiperazinyl, morpholinyl and thiomorpholinyl; —OH and —$O(C_1-C_6)$alkyl, more preferably —$O(C_1-C_3)$alkyl, most preferably methoxy and ethoxy.

Most preferably, substituted aryl and heteroaryl rings in $R^1$, $R^a$, $R^w$ and $R^z$ groups are mono-, di- or tri-substituted, more preferably mono- or di-substituted by substituents selected from the group consisting of chloro, fluoro, bromo, methyl, —$NO_2$, —CN, —OH, and methoxy.

Preferably substituted heterocyclyl groups contained within $R^a$ and $R^w$ groups are mono-, di- or tri-substituted, more preferably mono- or di-substituted, by substituents selected from the group consisting of —$(C_1-C_7)$hydrocarbyl, preferably benzyl and —$(C_1-C_6)$alkyl; more preferably methyl, ethyl and benzyl; —C(=O)$(C_1-C_6)$alkyl, preferably —C(=O)$(C_1-C_3)$alkyl, more preferably acetyl; and —$(C_1-C_6)$perfluoroalkyl, preferably —$(C_1-C_3)$perfluoroalkyl, more preferably —$CF_3$.

More preferably substituted heterocyclyl groups contained within $R^a$ and $R^w$ groups are mono-, or di-substituted, by substituents selected from the group consisting of —$(C_1-C_6)$alkyl; more preferably methyl and ethyl, and —C(=O)$(C_1-C_3)$alkyl, more preferably acetyl.

According to some embodiments of the invention, the sum of a and b is at least 2. According to other embodiments of the invention, the sum of a and b is at least 3. According to still other embodiments of the invention, the sum of a and b is at least 4. According to some embodiments of the invention, both a and b are at least 1. According to other embodiments of the invention, a is at least 1 and b is at least 2. According to other embodiments of the invention, b is at least 1 and a is at least 2. According to still other embodiments of the invention, both a and b are at least 2.

According to preferred embodiments of compounds of Formula I:
  when b is 1, substitution of $R^3$ groups on Q is at the ortho- or para-position;
  when b is 2, substitution of $R^3$ groups on Q is at either ortho- and para-positions, or at both ortho-positions; and
  when b is 3, substitution of $R^3$ groups on Q is at the para-position and at both ortho-positions.

Preferably, for compounds according to Formula I, Q is aryl; b is 1, 2 or 3; and each $R^2$ is —$OR^v$ or halogen, which may be the same or different.

More preferably, for compounds according to Formula I, Q is phenyl; b is 2 or 3; and each $R^2$ is —$OR^v$, which may be the same or different. Most preferably, each $R^2$ is —$OCH^3$.

In one aspect of the invention, processes for preparing compounds according to Formula IE are provided.

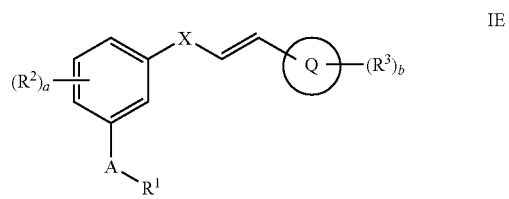

wherein $R^1$, $R^2$, $R^3$, A, Q, a and b, and X are as defined herein for compounds of Formula I.

In one embodiment of the invention, processes for preparing (E)-styrylbenzylsulfones compounds according to Formula IE wherein $R^1, R^2, R^3, A, Q, a$ and b are as defined herein for compounds of Formula I, and X is —CH*$R^x$—Y—, are provided, comprising a synthesis reaction as shown in Scheme 1.

In another embodiment of the invention, processes for preparing (E)-styrylbenzylsulfones compounds according to Formula IE wherein $R^1, R^2, R^3, A, Q, a$ and b are as defined herein for compounds of Formula I, and X is —CH*$R^x$—Y—, are provided, comprising Knoevenagel-type condensation synthesis reaction as shown in Scheme 2.

In one preferred embodiment of the invention, processes for preparing (E)-styrylbenzylsulfones compounds according to Formula IE wherein $R^1, R^2, R^3, A, Q, a$ and b are as defined herein for compounds of Formula I, and X is —CH*$R^x$—Y—, are provided, comprising an aldehyde condensation synthesis reaction as shown in Scheme 3.

In another preferred embodiment of the invention, processes for preparing (E)-styrylbenzylsulfones compounds according to Formula IE wherein $R^1, R^2, R^3, A, Q, a$ and b are as defined herein for compounds of Formula I, and X is —CH*$R^x$—Y—, are provided, comprising an Knoevenagel-type condensation synthesis reaction as shown in Scheme 4.

In yet another preferred embodiment of the invention, processes for preparing bioavailable water soluble prodrug (E)-styrylbenzylsulfones compounds according to Formula IE wherein $R^1, R^2, R^3, A, Q, a$ and b are as defined herein for compounds of Formula I, and X is —CH*$R^x$—Y—, are provided, comprising a synthesis reaction as shown in Scheme 5.

In yet another preferred embodiment of the invention, processes for preparing (E)-styrylbenzylsulfones compounds according to Formula IE wherein $R^1, R^2, R^3, A, Q, a$ and b are as defined herein for compounds of Formula I, and X is —CH*$R^x$—Y—, are provided, comprising a synthesis reaction as shown in Scheme 6.

In yet another preferred embodiment of the invention, a process for preparing compound (E)-2,4,6-Trimethoxystyryl-3-Hydroxy-4-Methoxybenzyl Sulfone (Compound ON 013100) is provided, comprising the synthesis reaction shown in Scheme 3.

In yet another preferred embodiment of the invention, a process for preparing compound (E)-2,4,6-Trimethoxystyryl-3-Hydroxy-4-Methoxybenzyl Sulfone (Compound ON 013100) is provided, comprising the synthesis reaction shown in Scheme 4.

In yet another preferred embodiment of the invention, a process for preparing bioavailable water soluble prodrug compound (E)-2,4,6-(Trimethoxystyryl)-3-O-Phosphate Disodium-4-Methoxybenzyl Sulfone (Compound ON 013105), is provided, comprising a synthesis reaction as shown in Scheme 5.

In yet another preferred embodiment of the invention, a process for preparing bioavailable water soluble prodrug compound (E)-2,4,6-(Trimethoxystyryl)-3-O-Phosphate Disodium-4-Methoxybenzyl Sulfone (Compound ON 013105) is provided, comprising the synthesis reaction shown in Scheme 6.

In yet another preferred embodiment of the invention, a process for bioavailable water soluble prodrug compound (E)-2,4,6-(Trimethoxystyryl)-3-O-Phosphate Disodium-4-Methoxybenzyl Sulfone (Compound 013105) is provided, comprising the synthesis reaction shown in Scheme 7.

In yet another aspect of the invention, compounds, compositions and methods for the treatment and/or prevention of cancer and other proliferative disorders are provided.

In yet another aspect of the invention, compounds which are selective in killing tumor cells at therapeutically useful concentrations are provided.

In yet another aspect of the invention, compounds, compositions and methods for inducing neoplastic cells to selectively undergo apoptosis are provided.

In yet another aspect of the invention, compounds, compositions and methods which enable prophylactic treatment of proliferative disorders are provided.

In yet another aspect of the invention, compounds, compositions and methods for protecting normal cells and tissues from the cytotoxic and genetic effects of exposure to ionizing radiation, in individuals who have incurred, will in the future incur, or are at risk for incurring exposure to ionizing radiation are provided. Exposure to ionizing radiation may occur in controlled doses during the treatment of cancer and other proliferative disorders. Alternatively, exposure to ionizing radiation may occur in uncontrolled doses beyond the norm accepted for the population at large during high risk activities or environmental exposures.

In yet another aspect of the invention, compositions and methods for protecting individuals from the cytotoxic side effects of mitotic phase cell cycle inhibitors and topoisomerase inhibitors, used in the treatment of cancer and other proliferative disorders are provided.

In yet another aspect of the invention, a method for treating cancer or other proliferative disorders which reduces or eliminates cytotoxic effects on normal cells is provided.

In yet another aspect of the invention, compositions and methods for enhancing the effects of mitotic phase cell cycle inhibitors and topoisomerase inhibitors, used for the treatment of cancer or other proliferative disorders are provided.

In yet another aspect of the invention, a therapeutic program for treating cancer or other proliferative disorder which includes administration of a cytoprotective compound prior to administration of a chemotherapeutic agent, which cytoprotective compound induces a reversible cycling quiescent state in non-tumored tissues is provided.

In yet another aspect of the invention, a method for safely increasing the dosage of mitotic phase cell cycle inhibitors and topoisomerase inhibitors, used in the treatment of cancer and other proliferative disorders is provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

General

Figure 1:
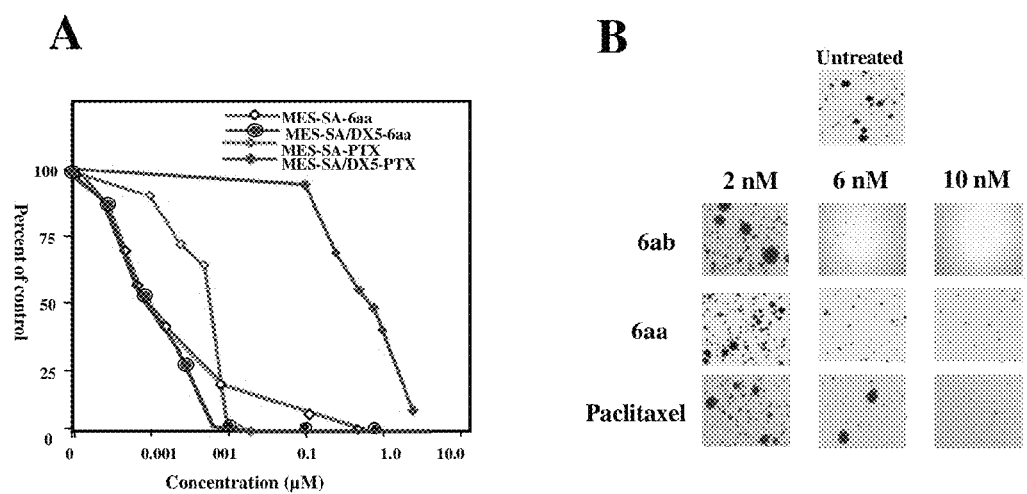
FIG. 1 Anti-tumor effects of (E)-2,4,6-Trimethoxystyryl-3-Hydroxy-4-Methoxybenzyl Sulfone (6aa). A. 6aa inhibits the growth of parental (MES-SA) and Paclitaxel resistant (MES-SA/DX5) cell lines with equal efficiency. The parental uterine sarcoma cells and the MDR positive (MES-SA/DX5) cells were plated into 6 well dishes and treated with various concentrations of 6aa and Paclitaxel for 96 h. The number of viable cells from duplicate plates was determined by trypan blue exclusion. B. Soft Agar Assays. MIA-PaCa-2 cells ($1.0 \times 10^5$) were plated in soft agar containing various concentrations of each compound in triplicates. After three weeks of growth, the plates were stained for 48 h using 0.05% nitroblue tetrazolium solution. Representative plates were photographed using an Olympus stereoscope mounted with a Sony digital camera system (DKC5000, Sony Inc).

The term "individual" or "subject", includes human beings and non-human animals. With respect to the disclosed radioprotective and cytoprotective methods, these terms refer, unless the context indicates otherwise, to an organism that is scheduled to incur, or is at risk for incurring, or has incurred, exposure to ionizing radiation or exposure to one or more cytotoxic chemotherapeutic agents.

The expression "effective amount" when used to describe therapy to a patient suffering from a proliferative disorder, refers to the amount of a compound according to Formula I that inhibits the growth of tumor cells or alternatively induces apoptosis of cancer cells, preferably tumor cells, resulting in a therapeutically useful and selective cytotoxic effect on proliferative cells when administered to a patient suffering from a cancer or other disorder which manifests abnormal cellular proliferation. The term "effective amount" is inclusive of amounts of a compound according to Formula I and its enantiomers, metabolites, prodrugs, polymorphs, the crystalline form, and anhydrous and hydrated forms thereof that may be metabolized to an active metabolite in an amount that inhibits the growth of tumor cells or induces apoptosis of cancer cells.

The term "antibody" is intended to encompass not only intact antigen-binding immunoglobulin molecules, but also to include antigen-binding fragments thereof such as Fab, Fab', F(ab')$_2$, and Fv fragments, capable of binding the epitopic determinant or any other fragment retaining the antigen-binding ability of an intact antibody.

The expression "humanized antibody" refers to an antibody that has its complementary determining regions (CDR's) derived from a non-human species immunoglobulin, and the remainder of the antibody molecule derived from a human immunoglobulin.

The expression "chimeric antibody" means an antibody comprising a variable region and a constant region derived from different species.

The expression "humanized chimeric antibody" is meant a chimeric antibody in which at least the constant region is human-derived.

The expression "monospecific polyclonal antibody" means an antibody preparation comprising multiple antibody species having specificity for a single antigen.

The term "proliferative disorder" means a disorder wherein cells are made by the body at an atypically accelerated rate.

Radioprotection

As used herein, "ionizing radiation" is radiation of sufficient energy that, when absorbed by cells and tissues, induces formation of reactive oxygen species and DNA damage. This type of radiation includes X-Rays, gamma rays, and particle bombardment (e.g., neutron beam, electron beam, protons, mesons and others), and is used for medical testing and treatment, scientific purposes, industrial testing, manufacturing and sterilization, weapons and weapons development, and many other uses. Radiation is typically measured in units of absorbed dose, such as the rad or gray (Gy), wherein 1 rad=0.01 Gy, or in units of dose equivalence, such as the rem or sievert (Sv), wherein 1 rem=0.01 Sv.

The Sv is the Gy dosage multiplied by a factor that includes tissue damage done. For example, penetrating ionizing radiation (e.g., gamma and beta radiation) have a factor of about 1, so 1 Sv=~1 Gy. Alpha rays have a factor of 20, so 1 Gy of alpha radiation=20 Sv.

By "effective amount of ionizing radiation" is meant an amount of ionizing radiation effective in killing, or in reducing the proliferation, of abnormally proliferating cells in an individual. As used with respect to bone marrow purging, "effective amount of ionizing radiation" means an amount of ionizing radiation effective in killing, or in reducing the proliferation, of malignant cells in a bone marrow sample removed from an individual.

By "acute exposure to ionizing radiation" or "acute dose of ionizing radiation" is meant a dose of ionizing radiation absorbed by an individual in less than 24 hours. The acute dose may be localized, as in radiotherapy techniques, or may be absorbed by the individual's entire body. Acute doses are typically above 10,000 millirem (0.1 Gy), but may be lower.

By "chronic exposure to ionizing radiation" or "chronic dose of ionizing radiation" is meant a dose of ionizing radiation absorbed by an individual over a period greater than 24 hours. The dose may be intermittent or continuous, and may be localized or absorbed by the individual's entire body. Chronic doses are typically less than 10,000 millirem (0.1 Gy), but may be higher.

By "at risk of incurring exposure to ionizing radiation" is meant that an individual may intentionally, e.g., by scheduled radiotherapy sessions, or inadvertently be exposed to ionizing radiation in the future. Inadvertent exposure includes accidental or unplanned environmental or occupational exposure.

By "effective amount of a radioprotective compound" is meant an amount of compound according to Formula I effective to reduce or eliminate the toxicity associated with radiation in normal cells of the individual, and also to impart a direct cytotoxic effect to abnormally proliferating cells in the individual. As used with respect to bone marrow purging, "effective amount" of the radioprotective compound according to Formula I means an amount of compound effective to reduce or eliminate the toxicity associated with radiation in bone marrow removed from an individual, and also to impart a direct cytotoxic effect to malignant cells in the bone marrow removed from the individual.

Cytoprotection

By "mitotic phase cell cycle inhibitor" is meant a chemical agent whose mechanism of action includes inhibition of a cell's passage through any portion of the mitotic (M) phase of the cell cycle.

By "effective amount" of a mitotic phase cell cycle inhibitor or topoisomerase inhibitor is meant an amount of said inhibitor effective in killing or reducing the proliferation of cancer cells in a host animal.

By "effective amount" of the cytoprotective compound according to Formula I is meant an amount of compound effective to reduce the toxicity of the mitotic phase cell cycle inhibitor or topoisomerase inhibitor on normal cells of the animal.

The expression "cell cycle" refers to the usual description of cell development in terms of a cycle consisting of a series of phases—interphase and M (mitotic) phase—and the subdivision of interphase into the times when DNA synthesis is proceeding, known as the S-phase (for synthesis phase), and the gaps that separate the S-phase from mitosis. G1 is the gap after mitosis but before DNA synthesis starts, and G2 is the gap after DNA synthesis is complete before mitosis and cell division. Interphase is thus composed of successive G1, s and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

By "topoisomerase" is meant an enzyme that catalyzes the conversion of DNA from one topological form to another by introducing transient breaks in one or both strands of a DNA duplex.

By "topoisomerase inhibitor" is meant a chemical agent whose mechanism of action includes interfering with the function of a topoisomerase.

"Topological isomers" are molecules that differ only in their state of supercoiling. Type I topoisomerase cuts one strand of DNA and relaxes negatively supercoiled DNA, but does not act on positively supercoiled DNA. Type II topoisomerase cuts both strands of DNA and increases the degree of negative supercoiling in DNA.

Chemical

The term "alkyl", by itself or as part of another substituent, e.g., alkoxy, haloalkyl or aminoalkyl, means, unless otherwise stated, a saturated hydrocarbon radical having the number of carbon atoms designated (i.e. $C_1$-$C_6$ means one, two, three, four, five or six carbons) and includes straight, branched chain, cyclic and polycyclic groups. Examples include: methyl, ethyl, propyl, isopropyl, butyl, isobutyl, tert-butyl, pentyl, neopentyl, hexyl, cyclohexyl, norbornyl and cyclopropylmethyl. Preferred alkyl groups are —($C_1$-$C_6$)alkyl. Most preferred is —($C_1$-$C_3$)alkyl, particularly ethyl, methyl and isopropyl.

"Substituted alkyl" means alkyl, as defined above, substituted by one, two or three substituents preferably independently selected from the group consisting of halogen, —OH, —O($C_1$-$C_4$)alkyl, —$NH_2$, —$N(CH_3)_2$, —$CO_2H$, —$CO_2$($C_1$-$C_4$)alkyl, —$CF_3$, —$CONH_2$, —$SO_2NH_2$, —C(=NH)$NH_2$, —CN and —$NO_2$. More preferably, the substituted alkyl contains one or two substituents independently selected from halogen, —OH, $NH_2$, —$N(CH_3)_2$, trifluoromethyl and —$CO_2H$; most preferably, independently selected from halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical having the designated number of carbons. A substitution of another group on alkylene may be at any substitutable carbon, i.e., the expression —C(=O)($C_1$-$C_4$ alkylene)$R^w$ would include, for example:

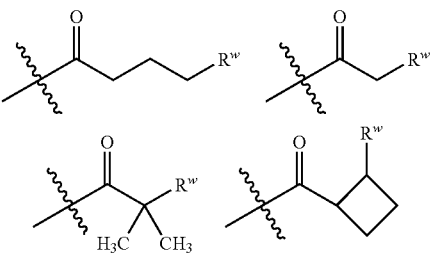

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle. Examples of amino groups include: —$NH_2$, methyl amino, diethyl amino, anilino, benzyl amino, piperidinyl, piperazinyl and indolinyl.

The term "aromatic" refers to a carbocycle or heterocycle having one or more polyunsaturated rings having aromatic character (4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "aryl-($C_1$-$C_3$)alkyl" means a radical wherein a one to three carbon alkylene chain is attached to an aryl group, e.g., —$CH_2CH_2$-phenyl. Preferred is aryl($CH_2$)— and aryl (CH($CH_3$))—. The term "substituted aryl-($C_1$-$C_3$)alkyl" means an aryl-($C_1$-$C_3$)alkyl radical in which the aryl group is substituted. Preferred is substituted aryl($CH_2$)—. Similarly, the term "heteroaryl($C_1$-$C_3$)alkyl" means a radical wherein a one to three carbon alkylene chain is attached to a heteroaryl group, e.g., —CH$_2$CH$_2$-pyridyl. Preferred is heteroaryl (CH$_2$)—. The term "substituted heteroaryl-(C$_1$-C$_3$)alkyl" means a heteroaryl-(C$_1$-C$_3$)alkyl radical in which the heteroaryl group is substituted. Preferred is substituted heteroaryl(CH$_2$)—.

The term "arylene" by itself or as part of another substituent means, unless otherwise stated, a divalent aryl radical. Preferred are divalent phenyl radicals, particularly 1,4-divalent phenyl radicals.

The term "cycloalkyl" refers to ring-containing alkyl radicals. Examples include cyclohexyl, cyclopentyl, cyclopropyl methyl and norbornyl.

The expression "exocyclic double bond," unless otherwise stated, refers herein to a carbon-carbon double bond external to a chemical ring structure. Specifically, the expression refers to the carbon-carbon double bond in compounds of the invention, which is not contained in either the phenyl ring or the aromatic ring, Q, but rather is the double bond which is alpha to the aromatic ring, Q;

The terms "halo" or "halogen" by themselves or as part of another substituent, e.g., haloalkyl, mean, unless otherwise stated, a fluorine, chlorine, bromine, or iodine atom, preferably, fluorine, chlorine, or bromine, more preferably, fluorine or chlorine.

The term "haloalkyl" means, unless otherwise stated, an alkyl group as defined herein containing at least one halogen substituent and no substituent that is other than halogen. Multiple halogen substituents, up to substitution of all substitutable hydrogens on the alkyl group may be the same or different. Preferred haloalkyl groups include, for example, perfluoro(C$_1$-C$_4$)alkyl, gem-difluoro(C$_1$-C$_4$)alkyl, and chloro(C$_1$-C$_4$)alkyl. More preferred haloalkyl groups include, for example, —CF$_3$, —C$_2$F$_5$, —CH$_2$CF$_3$, —CHF$_2$, CF$_2$CH$_3$, and —CH$_2$Cl.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein, in the sulfur heteroatoms may be optionally oxidized and the nitrogen heteroatoms may be optionally quaternized or oxidized. The oxygens bonded to oxidized sulfur or nitrogen may be present in addition to the one or two heteroatoms in the heteroalkyl group. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—SO$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A monocyclic heteroaryl group is a 5-, 6, or 7-membered ring, examples of which are pyrrolyl, furyl, thienyl, pyridyl, pyrimidinyl and pyrazinyl. A polycyclic heteroaryl may comprise multiple aromatic rings or may include one or more rings which are partially saturated. Examples of polycyclic heteroaryl groups containing a partially saturated ring include tetrahydroquinolyl and 2,3-dihydrobenzofuryl. For compounds of Formula I, the attachment point on ring Q is understood to be on an atom which is part of an aromatic monocyclic ring or a ring component of a polycyclic aromatic which is itself an aromatic ring. The attachment point on ring Q may be a ring carbon or a ring nitrogen and includes attachment to form aromatic quaternary ammonium salts such as pyridinium.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The term "heteroarylene" by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from pyridine, piperazine, pyrimidine, pyrazine, furan, thiophene, pyrrole, thiazole, imidazole and oxazole.

For compounds of the present invention, when an aromatic or heteroaromatic ring is attached to a position and the ring comprises a polycyclic ring which is partially saturated, the attachment point on the aromatic or heteroaromatic ring is on a ring atom of an aromatic ring component of the polycyclic ring. For example, on the partially saturated heteroaromatic ring, 1,2,3,4-tetrahydroisoquinoline, attachment points are ring atoms at the 5-, 6-, 7- and 8-positions.

The aforementioned listing of heterocyclyl and heteroaryl moieties is intended to be representative, not limiting.

The term "hydrocarbyl" refers to any moiety comprising only hydrogen and carbon atoms. Preferred hydrocarbyl groups are (C$_1$-C$_{12}$)hydrocarbyl, more preferred are (C$_1$-C$_7$) hydrocarbyl, most preferred are benzyl and (C$_1$-C$_6$)alkyl.

The term "hydrocarbylene" by itself or as part of another substituent means, unless otherwise stated, a divalent moiety comprising only hydrogen and carbon atoms. A substitution of another group on hydrocarbylene may be at any substitutable carbon, i.e., the expression —($C_1$-$C_6$ hydrocarbylene)$R^w$ would include, for example:

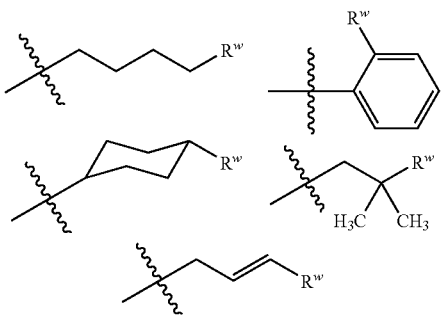

The expression "carboxy terminally-linked peptidyl residue" refers to a peptide radical as a substituent on a molecule of Formula I. The radical is bonded through the carboxyl functionality of a peptidyl residue to form a carboxamide, carboxylic ester or acyl sulfide (—S—C(=O)—).

The amino acid residues comprising the carboxy terminally-linked peptidyl residue may comprise natural or unnatural amino acids or a combination thereof. Unnatural amino acids are amino acids other than the twenty essential amino acids. One example of an unnatural amino acid is a D-amino acid, i.e., an amino acid having a stereochemistry opposite the stereochemistry of natural L-amino acids. Another example of an unnatural amino acid is an amino acid having a side chain that differs from the side chains occurring in the natural amino acids, for example α-ethyl glycine or α-phenyl glycine. A third example is an amino acid having a backbone variation. Examples of amino acid backbone variations include β-alanine and β-turn mimetics such as Freidinger's lactam. A fourth example of an unnatural amino acid is an amino acid having two α-substituents, e.g., α,α-dimethyl glycine.

The amino terminus of the carboxy terminally-linked peptidyl residue may be an unsubstituted amino group, or may be substituted. Substitutions on the amino terminus include mono- and di-($C_1$-$C_6$ alkyl), —C(=O)($C_1$-$C_6$ alkyl), —C(=O)O($C_1$-$C_7$)hydrocarbyl) and commonly employed nitrogen protecting groups such as tert-butoxycarbonyl (BOC), carbobenxyloxy (CBZ), 2,4-dimethoxybenzyl and fluorenylmethoxycarbonyl (FMOC).

The expression "amino terminally-linked peptidyl residue" refers to a peptide radical as a substituent on a compound according to Formula I. The radical is bonded through the terminal amino functionality of the peptidyl residue to form a carboxamide, sulfonamide, urea or thiourea.

The carboxy terminus of the amino terminally-linked peptidyl residue may be a free carboxyl group or a salt thereof, or may be derivatized as an ester or amide. Suitable esters include alkyl, preferably ($C_1$-$C_6$) alkyl; and arylalkyl, preferably benzyl esters. Suitable amides include the primary amide and secondary and tertiary amides comprising one or two nitrogen substituents independently selected from ($C_1$-$C_3$) alkyl, preferably methyl or ethyl; aryl, preferably phenyl; and aryl($C_1$-$C_3$)alkyl groups, preferably benzyl or substituted benzyl.

As with the carboxy terminally-linked peptidyl residues, the amino acids comprising the amino terminally-linked peptidyl residue may comprise natural or unnatural amino acids or a combination thereof.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "trifluoro($C_x$-$C_y$)alkyl" means an alkyl group with a minimum of x carbon atoms and a maximum of y carbon atoms, wherein the three hydrogen atoms on a terminal carbon (—$CH_3$) are replaced by fluorine atoms. Examples include —$CH_2CF_3$, —$(CH_2)_2$—$CF_3$ and —$CH(CH_3)$—$CF_3$.

The term "difluoro($C_x$-$C_y$)alkyl" means an alkyl group with a minimum of x carbon atoms and a maximum of y carbon atoms, wherein one carbon atom is geminally substituted with two fluorine atoms. The fluorine-substituted carbon may be the any carbon in the chain having at least two substitutable hydrogens, including the a terminal —$CH_3$ group and the proximal carbon through which the difluoro ($C_x$-$C_y$)alkyl is bonded to the rest of the molecule. Examples include —$CH_2CF_2H$, —$(CH_2)_2$—$CF_2H$ and —$CF_2$—$CH_3$ and 3,3-difluorocyclohexyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The naming of compounds disclosed herein was done by employing the structure naming programs included in ChemDraw software packages. The compounds, except for the α,b-unsaturated sulfonamides, were named using the "Structure to Name" program within ChemDraw Ultra Version 8.0 (© 1985-2003, CambridgeSoft Corporation, 100 Cambridgepark Drive, Cambridge, Mass. 02140 USA). The structures of the α,b-unsaturated sulfonamides disclosed herein were named using the Nomenclator Plug-in for ChemDraw 7.0.

Compounds of Formula I may be prepared via synthetic organic chemistry methods within the capability of a chemist of ordinary skill. Compounds of Formula I wherein the exocyclic carbon-carbon double bond is (E)- is preferably prepared via procedures that are selective for the preparation of (E)-olefins respectively. The synthetic routes for the preparation of α,β-Unsaturated Sulfoxides and Sulfones of Formula IE are shown below in Schemes 1, 2, 3, 4, 5, and 6.

A. Preparation of α,β-Unsaturated Sulfoxides and Sulfones of Formula I (i) Preparation of Compounds of Formula IE One preferred preparation of (E)-compounds of Formula I wherein X is —C*H($R^x$)SO— or —C*H($R^x$)$SO_2$—, is by a Knoevenagel condensation according to the Scheme 1 below, wherein $R^1$, $R^2$, $R^3$, $R^x$, A, Q, a, b, n and * are as defined herein for Formula I.

In one preferred embodiment of the preparation of (E)-compounds of Formula I, the synthesis route illustrated in Scheme 1 serves to produce the compound of Formula 6, which is itself a compound of Formula I. In addition, the compound of Formula 6 serves as advanced intermediate which may be further derivatized to provide additional novel compounds of Formula I. A preferred embodiment for synthesis route illustrated in Scheme 1 is depicted in Example 1, infra.

In Scheme 1, substituted benzyl bromides, 1, wherein R is defined as in Table 1 infra, are reacted with thioglycollic acid 2, in the presence of mild or strong bases, to obtain compound 3. Suitable base agents include, e.g., NaOH, MeOH, sodium-, potassium-, lithium hexamethyldisilazide, lithium diisopropyl amide, and the like. The reaction is preferably performed at room temperature or higher, more preferably from 30° C. to 50° C. Complete oxidation of 3, with hydrogen peroxide in the presence of glacial acetic acid yields 4. The oxidation reaction is preferably performed at room temperature or higher, more preferably from 30° C. to 50° C. Knoevenagel condensation of 4, with aromatic aldehydes 5, wherein $R^1$ is defined as in Table 1 infra, in toluene in the presence of catalytic amounts of piperidine and benzoic acid yields styryl benzyl sulfones, 6, wherein R and $R^1$ as defined herein. The Knoevenagel condensation reaction is preferably performed at 120° C. or higher. Alternately, the condensation between 4 and 5 may be carried out in glacial acetic acid in the presence of a catalytic amount of benzylamine to obtain 6. The condensation reaction is preferably performed at 118° C. or higher. Preferably, the reaction temperatures for condensation are about 120° C. to about 140° C.

as in Table 1 infra, in absolute alcohol in the presence of a base to obtain 9. Suitable base agents include, e.g., NaOH, KOH, and LiOH. Other suitable solvents include, e.g., methanol, ethanol, n-propanol, isopropanol, butanol, acetic acid and triethylamine. The reaction is preferably performed at room temperature or higher, more preferably from 30° C. to 50° C. Oxidation of 9 with hydrogen peroxide in glacial acetic acid yields 10. The oxidation reaction is preferably performed at room temperature or higher, more preferably from 30° C. to 50° C. Reduction of the carbonyl group in 10 with sodium borohydride in methanol yields corresponding alcohol, 11. Suitable reducing agents include hydride reducing agents, e.g., $NaBH_4$ and $NaBH_3CN$. Other suitable solvents include, e.g., tetrahydrofuran (THF), methanol, ethanol, n-propanol, isopropanol, butanol or acetic acid. The reduction reaction is preferably performed at low temperature, preferably from −40° C. to 0° C. Elimination of water from 11 in refluxing solution of p-toluenesulfonic acid in benzene afforded 6. The reduction reaction is preferably performed at 80° C. or higher, more preferably from about 120° C. to about 140° C.

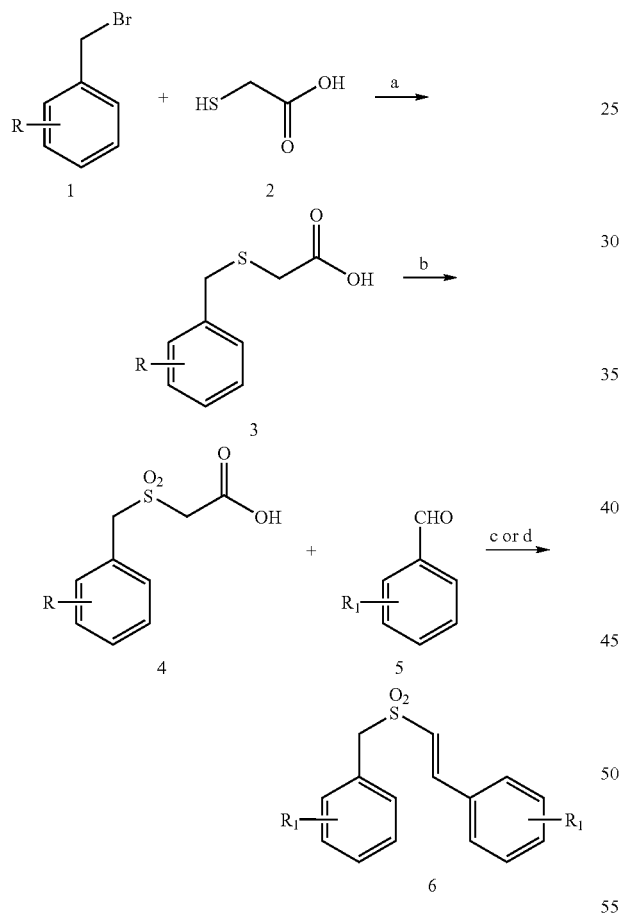

In another preferred embodiment of the preparation of (E)-compounds of Formula I, the synthesis route illustrated in Scheme 2 also serves to produce mono substituted styryl benzyl sulfones such as the compound of Formula 6, which as noted supra is itself a compound of Formula I and serves as an advanced intermediate which may be further derivatized to provide additional novel compounds of Formula I. A preferred embodiment for the synthesis route illustrated in Scheme 1 is depicted in Example 1, infra.

In scheme 2, benzyl mercaptans with desired substituents, 7, wherein R is defined as in Table 1 infra, are reacted with α-bromo substituted acetophenones, 8, wherein $R^1$ is defined In another preferred embodiment of the preparation of (E)-compounds of Formula I, the aldehyde condensation synthesis route illustrated in Scheme 3 serves to produce the compound of Formula 20, which is itself a compound of Formula I. In addition, the compound of Formula 20 serves as advanced intermediate which may be further derivatized to provide additional compounds of Formula I. A preferred embodiment for the aldehyde condensation synthesis route illustrated in Scheme 3 is depicted in Example 1, infra.

In Scheme 3, isovanillin 12 was reacted with TBDMS-THF to produce TBDMS protected isovanillin 13. Suitable solvents include, e.g., DMF, tetrahydrofuran (THF). The reaction is preferably performed at room temperature or higher, more preferably from 30° C. to 50° C. TBDMS protected isovanillin 13 was reduced to alcohol 14 with sodium borohydride. Suitable reducing agents include hydride reducing agents, e.g., $NaBH_4$ and $NaBH_3CN$. Suitable solvents include, e.g., MeOH ethanol, n-propanol, isopropanol, butanol and acetic acid. The reduction reaction is preferably performed at low temperature, preferably from −40° C. to 0° C. The benzyl alcohol 14 was converted to benzyl chloride 15 with $SOCl_2$. The reaction is preferably performed at low temperature, preferably from −40° C. to 0° C. Benzyl chloride 15 was subsequently converted to 16 by condensing with thioglycollic acid. Suitable base agents include, e.g. NaOH, KOH, and LiOH. Other suitable solvents include, e.g., MeOH, ethanol, n-propanol, isopropanol, butanol, triethylamine and tetrahydrofuran (THF). The condensation reaction is preferably performed at room temperature or higher, more preferably from 30° C. to 50° C. Deprotection of TBDMS with tetrabutyl ammonium fluoride and subsequent oxidation of 17 with hydrogen peroxide provided 18. The deprotection reaction is carried out in tetrahydrofuran. The deprotection reaction is carried out at room temperature or higher, more preferably from 30° C. to 50° C. Condensation of 18 with aldehyde 19 provided styryl benzyl sulfone 20. Other suitable solvents for the condensation reaction include, e.g., toluene, triethylamine and glacial acetic acid in the presence of bases like piperidine, triethylamine and benzylamine. The deprotection reaction is carried out at 120° C. or higher.

Scheme 3 Synthesis of (E)-2,4,6-(Trimethoxystyryl)-3-Hydroxy-4-Methoxybenzyl Sulfone

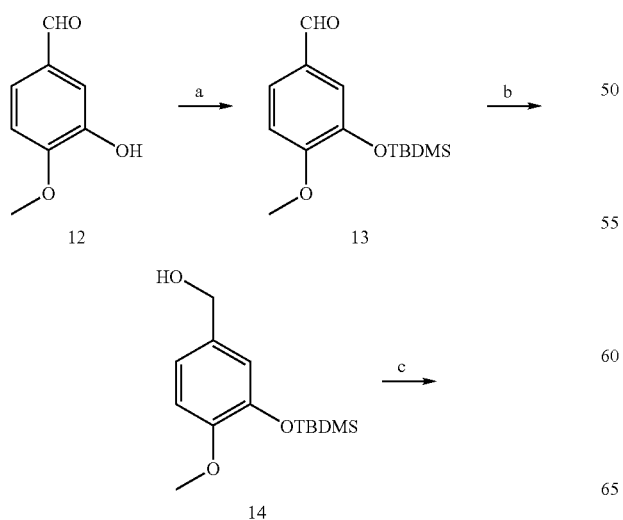

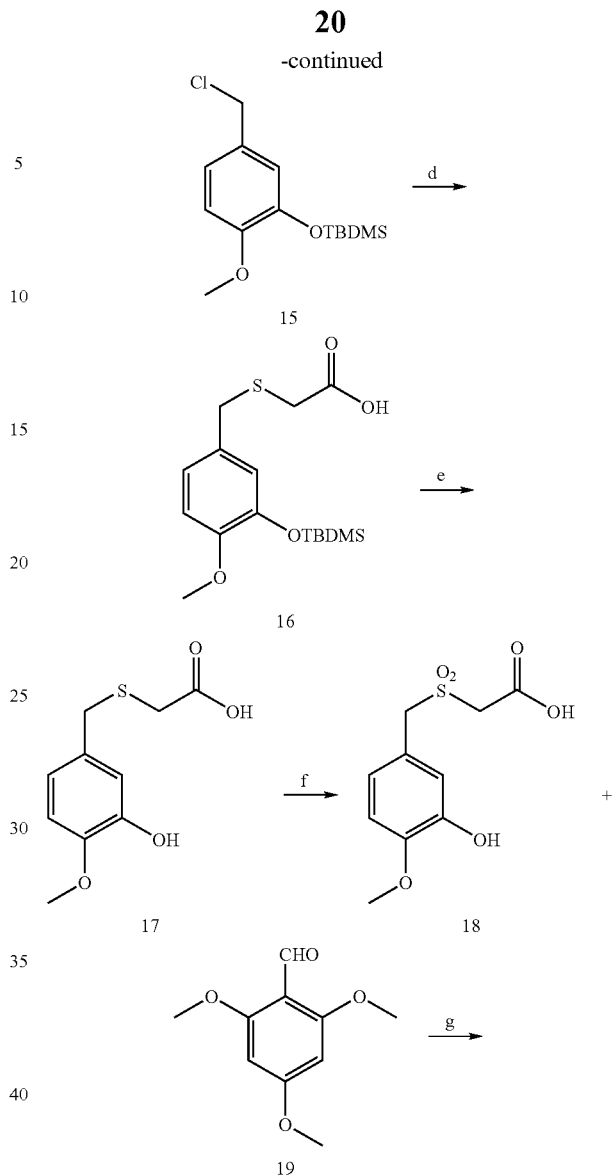

In another preferred embodiment of the preparation of (E)-compounds of Formula I, the Knoevenagel-type condensation synthesis reaction as shown in Scheme 4 serves to produce the compound of Formula 20, which is itself a compound of Formula I. In addition, the compound of Formula 20 serves as advanced intermediate which may be further derivatized to provide additional compounds of Formula I. A preferred embodiment for the Knoevenagel-type condensation synthesis reaction illustrated in Scheme 4 is depicted in Example 1, infra.

In Scheme 4, Isovanillin 12 was reacted with 4-toluene-sulfonyl chloride in the presence of pyridine to obtain compound 21. Other suitable solvents for the reaction include, e.g., substituted pyridines, trimethylamine, triethylamine and DIPEA. The reaction is preferably performed at 30° C. to 50° C. or higher. Reduction of 21 with sodium borohydride gave 22. Suitable reducing agents include hydride reducing agents, e.g., $NaBH_4$ and $NaBH_3CN$. Other suitable solvents include, e.g., MeOH ethanol, n-propanol, isopropanol, butanol and acetic acid. The reduction reaction is preferably performed at 20° C. Treatment of 22 with thionyl chloride in benzene resulted in 23. Other suitable solvents for the reaction include, e.g., pyridine, substituted pyridines, trimethylamine, triethylamine and DIPEA. The reaction is preferably performed at 15° C. to 20° C. or higher. On condensation with thioglycollic acid, 23 yielded benzylthioacetic acid 24. Suitable base reagents include, e.g., NaOH, KOH, and LiOH. Other suitable solvents include, e.g., MeOH ethanol, n-propanol, isopropanol, butanol, acetic acid, and triethylamine. The condensation reaction is performed at about 65° C. Preferably, the reaction temperatures for condensation are about 60° C. to about 85° C. Oxidation of 24 with hydrogen peroxide yields corresponding sulfonylacetic acid 25. Other suitable solvents for the oxidation include, e.g., acetic acid, MeOH ethanol, n-propanol, isopropanol and butanol. The oxidation reaction is preferably performed at room temperature or higher. Knoevenagel type condensation of 25 with 2,4,6-trimethoxy benzaldehyde 19 in the presence of a base produced unsaturated sulfone 26. The Knoevenagel condensation reaction is preferably performed at 80° C. or higher. Preferably, the reaction temperatures for condensation are about 80° C. to about 140° C. Suitable base reagents include, e.g., NaOH, KOH, LiOH, triethylamine and piperidine in benzoicacid. Suitable solvents include, e.g., xylene, toluene, $C_6H_6$ and MeOH. Removal of tosyl group by treating 26 with sodium hydroxide gave the styryl benzyl sulfone 20. Suitable base reagents include, e.g., NaOH, KOH, and LiOH. Other suitable solvents include, e.g., MeOH ethanol, n-propanol, isopropanol, butanol, triethylamine and acetic acid. The reaction is preferably performed at 80° C. or higher. Preferably, the reaction temperatures are about 80° C. to about 140° C.

Scheme 4. Alternate Method for the Synthesis of (E)-2,4,6-(Trimethoxystyryl)-3-Hydroxy-4-Methoxybenzyl Sulfone

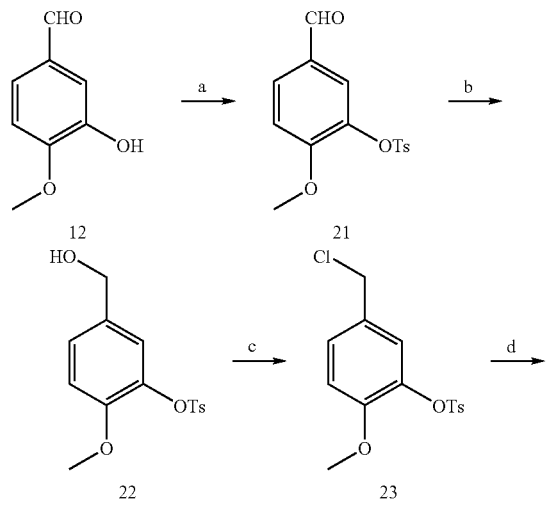

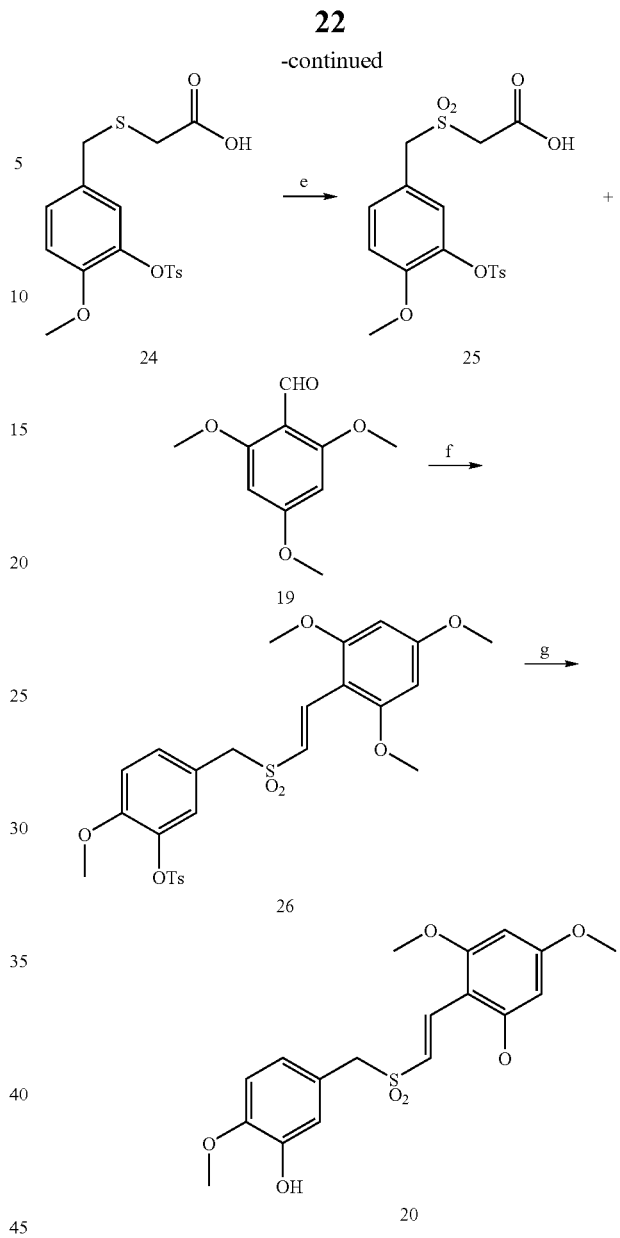

In yet another preferred embodiment of the preparation of (E)-compounds of Formula I, the synthesis reaction as shown in Scheme 5 is used for preparing the bioavailable water soluble sodium phosphate prodrug (E)-styrylbenzylsulfone compound of Formula 29, which is itself a compound of Formula I. In addition, the compound of Formula 29 serves as advanced intermediate which may be further derivatized to provide additional compounds of Formula I. A preferred embodiment for the synthesis reaction illustrated in Scheme 5 is depicted in Example 1, infra.

In Scheme 5, the prodrug was synthesized in three steps starting from styryl benzyl sulfone 20. Phosphorylation of phenolic group in 20 employing dibenzyl phosphite under basic conditions gave O-dibenzyl phosphate 27. Suitable base reagents include, e.g., $KH_2PO4$, NaOH, KOH, and LiOH. Other suitable solvents include, e.g., triethylamine, MeOH ethanol, n-propanol, isopropanol, and butanol. The reaction is preferably performed at room temperature or higher, more preferably from 30° C. to 50° C. Cleavage of benzyl groups with bromo trimethylsilane in acetonitrile produced 3-O-phosphate 28. Suitable solvents include, e.g., dichloromethane, MeOH ethanol, n-propanol, isopropanol, butanol, acetic acid and triethylamine. The reaction is preferably performed at room temperature or higher, more preferably from 30° C. to 50° C. Treatment of the phosphonate acid 28 with sodium hydroxide in anhydrous ethylene glycol dimethyl ether yielded disodium-O-phosphate 29. Suitable base reagents include, e.g., KH$_2$PO4, NaOH, KOH, and LiOH. Other suitable solvents include, e.g., ethyleneglycoldimethyl ether, dichloromethane, MeOH ethanol, n-propanol, isopropanol, butanol, acetic acid and triethylamine. The reaction is preferably performed at room temperature or higher, more preferably from 30° C. to 50° C.

Scheme 5. Method for the Synthesis of (E)-2,4,6-(Trimethoxystyryl)-3-O-Phosphate Disodium-4-Methoxybenzyl Sulfone

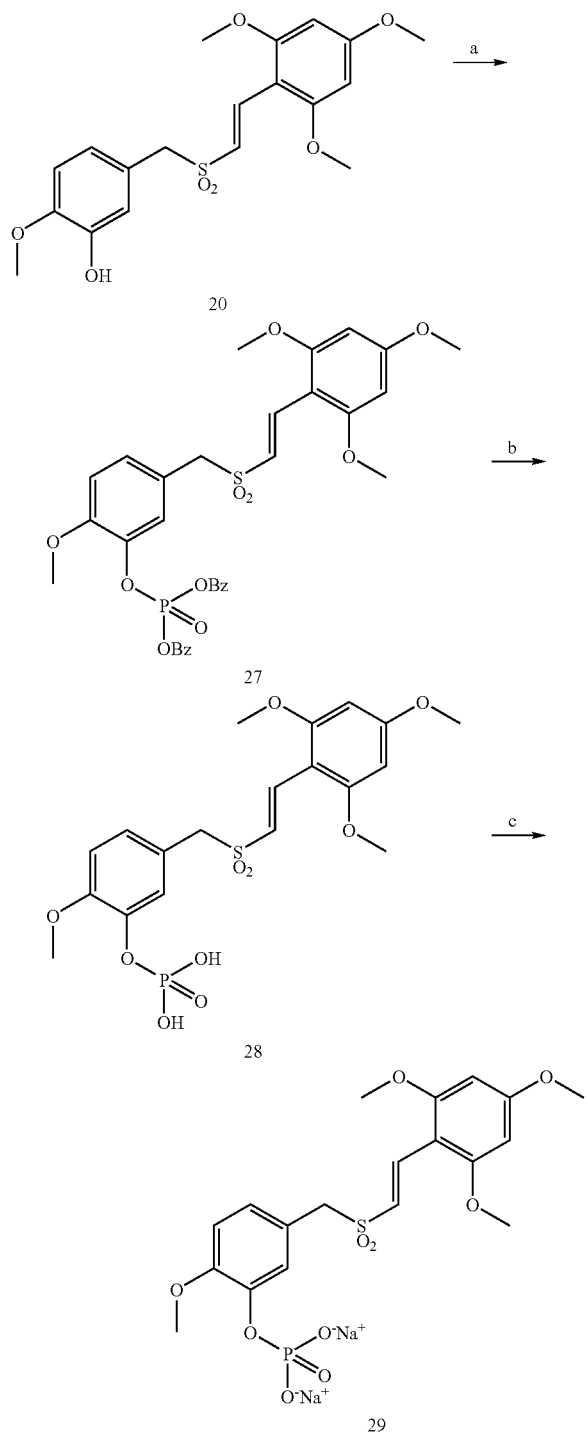

In yet a more preferred embodiment of the preparation of (E)-compounds of Formula I, the synthesis reaction as shown in Scheme 6 is used for preparing the bioavailable water soluble sodium phosphate prodrug (E)-styrylbenzylsulfone compound of Formula 29, which is itself a compound of Formula I. In addition, the compound of Formula 29 serves as advanced intermediate which may be further derivatized to provide additional compounds of Formula I. A preferred embodiment for the synthesis reaction illustrated in Scheme 6 is depicted in Example 2, infra.

In Scheme 6, Stage 1, isovanillin 12 is reacted with 4-toluenesulfonyl chloride in the presence of pyridine to obtain compound 21. The reaction is preferably performed at 70° C. to 80° C. In Stage 2, reduction of 21 with sodium borohydride as reducing agent in methanol yields 22. The reduction reaction is preferably performed at 15-20° C. In Stage 3, treatment of 22 with thionyl chloride in benzene with subsequent washing in hexane results in 23. The reaction is preferably performed at 15° C. to 20° C. In Stage 4, on condensation with thioglycollic acid, 23 yields benzylthioacetic acid 24. The condensation reaction is performed at 65° C. Preferably, the reaction temperatures for condensation are about 60° C. to about 80° C. In Stage 5, oxidation of 24 with hydrogen peroxide yields corresponding sulfonylacetic acid 25. The oxidation reaction is preferably performed at room temperature or higher, more preferably from 30° C. to 50° C. In Stage 6, Knoevenagel type condensation of 25 with 2,4,6-trimethoxy benzaldehyde 19 in the presence of a base produces unsaturated sulfone 26. Suitable base reagents include, e.g., NaOH, KOH, and LiOH. Suitable solvents include, e.g., MeOH, ethanol, n-propanol, isopropanol, butanol and acetic acid. The Knoevenagel condensation reaction is performed at about 80° C. Preferably, the reaction temperatures for condensation are about 80° C. to about 140° C. In Stage 7, removal of tosyl group by treating 26 with sodium hydroxide gave the styryl benzyl sulfone 20. The reaction is preferably performed at about 80° C. or higher. Preferably, the reaction temperatures are about 80° C. to about 140° C. Other suitable base reagents include, e.g., KOH, and LiOH. Suitable solvents include, e.g., MeOH ethanol, n-propanol, isopropanol and butanol. In Stage 8, phosphorylation of the phenolic group in 20 employing dibenzyl phosphite in KH$_2$PO4 with triethylamine as solvent yields O-dibenzyl phosphate 27. The reaction is preferably performed at room temperature. Suitable base reagents include, e.g., NaOH, KOH, and LiOH. Suitable solvents include, e.g., MeOH ethanol, n-propanol, isopropanol, butanol and acetic acid. In Stage 9, cleavage of the benzyl groups with bromo trimethylsilane in acetonitrile yields 3-O-phosphate 28. The reaction is preferably performed at room temperature. Other suitable solvents include, e.g., MeOH ethanol, n-propanol, isopropanol and butanol. In Stage 10, treatment of the phosphate 28 with sodium hydroxide in anhydrous ethylene glycol dimethyl ether yielded disodium-O-phosphate 29. The reaction is preferably performed at room temperature or higher. Other suitable base reagents include, e.g., KOH, and LiOH. Other suitable solvents include, e.g., MeOH, ethanol, n-propanol, isopropanol and butanol.

Scheme 6: Method for the Synthesis of (E)-2,4,6-(Trimethoxystyryl)-3-O-Phosphate Disodium-4-Methoxybenzyl Sulfone
STAGE-1
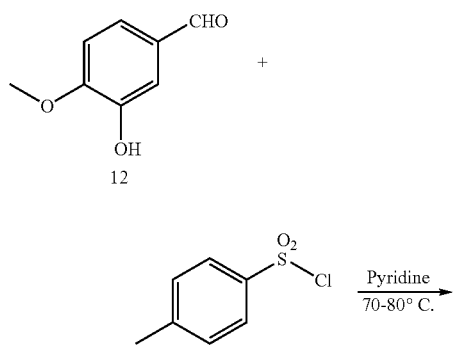
STAGE-2:
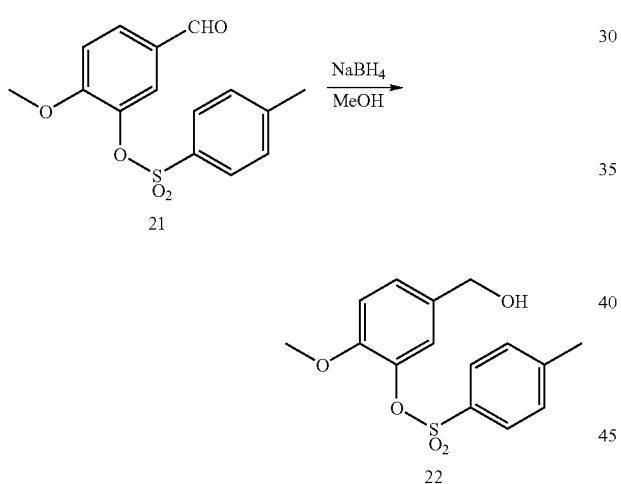
STAGE-3:
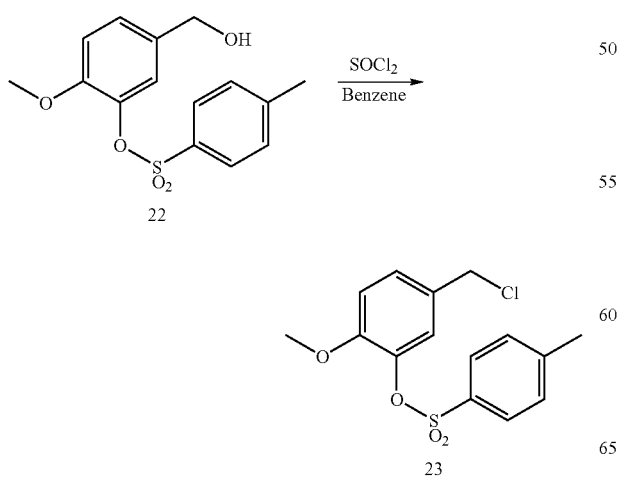
STAGE-4:
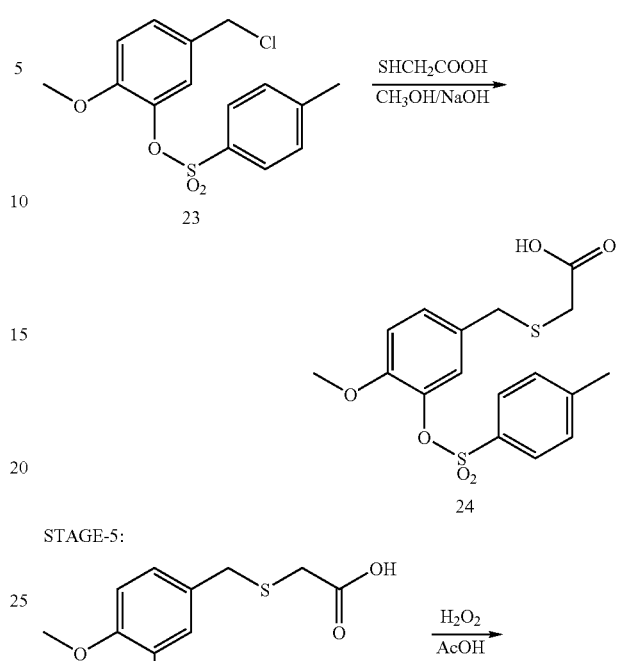
STAGE-5:
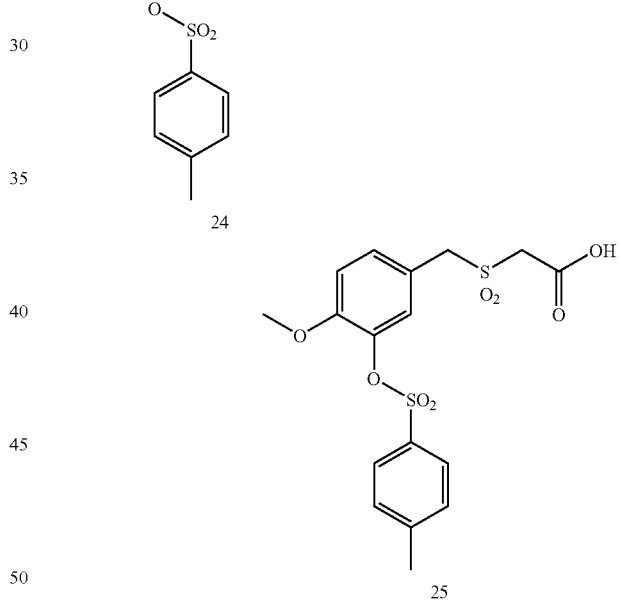
STAGE-6:
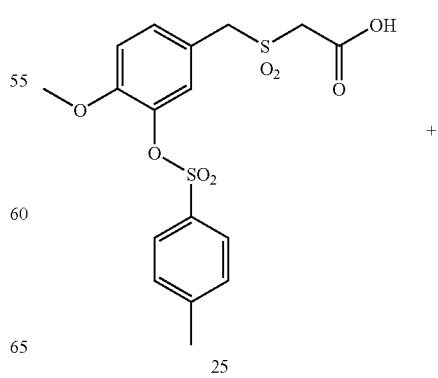

US 8,735,620 B2
27
-continued
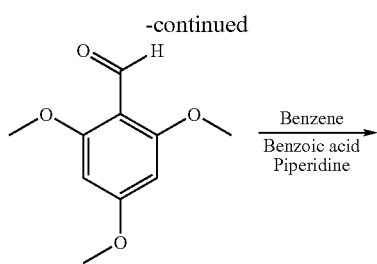
STAGE-7:
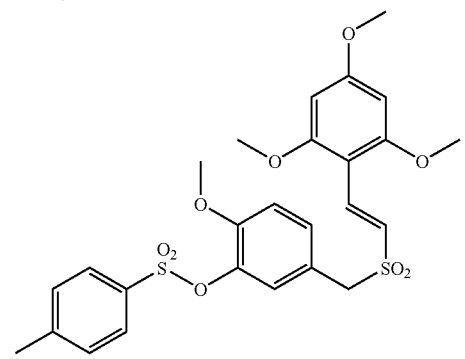
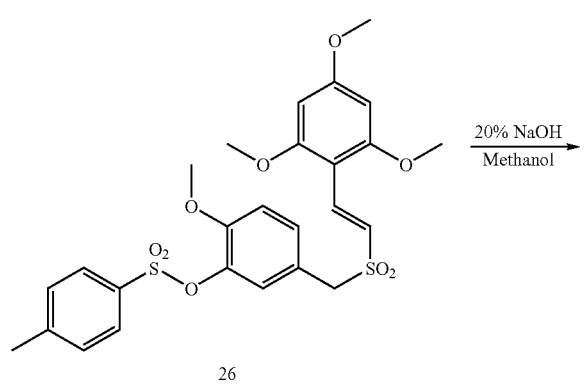
STAGE-8
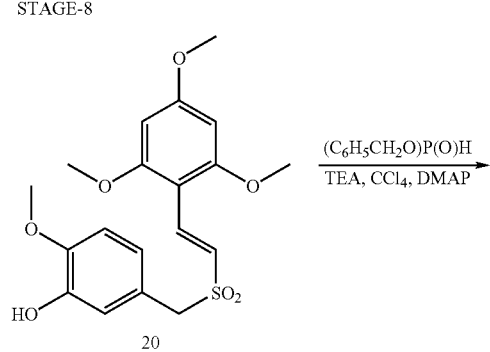
28
-continued
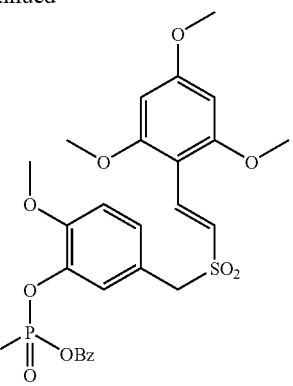
27
STAGE-9
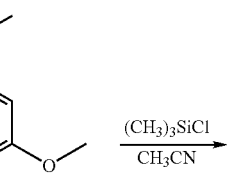
27
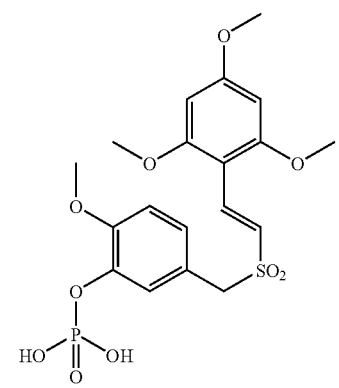
28
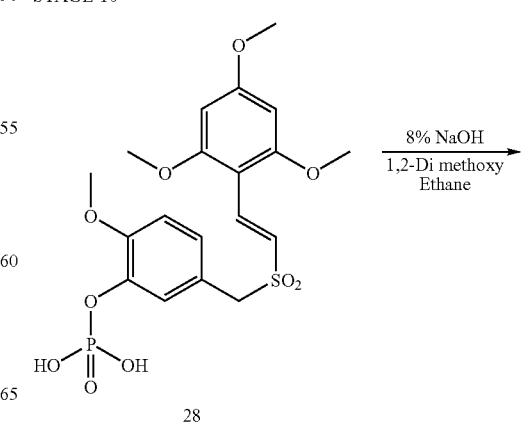
28
STAGE-10

-continued

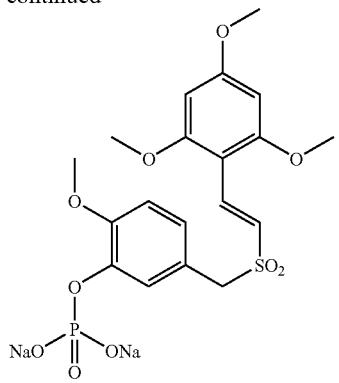

29

In yet a more preferred embodiment of the preparation of (E)-compounds of Formula I, the synthesis reaction as shown in Scheme 7 is used for preparing the bioavailable water soluble sodium phosphate prodrug (E)-styrylbenzylsulfone compound of Formula 29, which is itself a compound of Formula I. In addition, the compound of Formula 29 serves as advanced intermediate which may be further derivatized to provide additional compounds of Formula I. A preferred embodiment for the synthesis reaction illustrated in Scheme 7 is depicted in Example 3, infra.

In Scheme 7, phosphorylation of the phenolic group in styryl benzyl sulfone 20 employing phosphorous oxychloride with triethylamine and THF as solvent yields the 3-O-chloro phosphate compound 20. The reaction is preferably performed at about 0° C. or higher. Preferably, the reaction temperatures are about 0° C. to room temperature. The 3-O-chloro phosphate compound 20 is then treated with potassium hydroxide in THF, and then treated with dilute HCl to yield the phosphoric acid precipitate of compound 20. The reaction is preferably performed at about 0° C. Suitable base reagents include, e.g., NaOH, and LiOH. Suitable solvents include, e.g., MeOH ethanol, n-propanol, isopropanol, and butanol. Treatment of the phosphate compound 20 with sodium hydroxide in methanol yielded disodium-O-phosphate compound 29. The reaction is preferably performed at room temperature or higher. Other suitable base reagents include, e.g., KOH, and LiOH. Other suitable solvents include, e.g., MeOH, ethanol, n-propanol, isopropanol, butanol and triethylamine.

The phosphoric acid precipitate of compound 20 is then dissolved in methanol and treated with sodium hydroxide to yield the disodium-O-phosphate 29. The reaction is preferably performed at room temperature or higher. Other suitable base reagents include, e.g., KOH, and LiOH. Other suitable solvents include, e.g., MeOH ethanol, n-propanol, isopropanol and butanol.

In yet another aspect of the present invention, compounds of Formula I prepared by the methods disclosed herein are useful for the treatment of proliferative disorders, non-cancer proliferative disorders, as well as radioprotective treatment, and chemoprotective treatment.

I. Treatment of Proliferative Disorders

In yet another aspect of the present invention, compounds of Formula IE and salts thereof prepared by the methods disclosed herein are believed to selectively inhibit proliferation of cancer cells, and kill various tumor cell types without killing (or with reduced killing of) normal cells. It is believed that cells are killed at concentrations where normal cells may be temporarily growth-arrested but not killed.

A. Treatment of Cancer

The compounds of Formula IE of the invention may be administered to individuals (mammals, including animals and humans) afflicted with cancer.

The compounds of the invention are believed to inhibit the proliferation of tumor cells and, for some compounds, to induce cell death. Cell death is believed to result from the induction of apoptosis. The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Karposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers including, for example, malignant melanoma, basal cell carcinoma, squamous cell carcinoma, Karposi's sarcoma, moles dysplastic nevi, lipoma, angioma, dermatofibroma, keloids, psoriasis; and adrenal gland cancers including, for example, neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

B. Treatment of Non-Cancer Proliferative Disorders

The compounds of Formula IE prepared by the methods disclosed herein are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compounds of the invention include, for example: hemangiomatosis in newborn, secondary progressive multiple sclerosis, atherosclerosis, chronic progressive myelodegenerative disease, neurofibromatosis, ganglioneuromatosis, keloid formation, Pagets Disease of the bone, fibrocystic disease of the breast, uterine fibroids, Peronies and Duputren's fibrosis, restenosis, benign proliferative breast disease, benign prostatic hyperplasia, X-linked lymphoproliferative disorder (Duncan disease), post-transplantation lymphoproliferative disorder (PTLD), macular degeneration, and retinopathies, such as diabetic retinopathies and proliferative vitreoretinopathy (PVR)

Other non-cancer proliferative disorders believed treatable by compounds of the invention include the presence of pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time.

Treatment of tumor cells with the compounds of the invention is believed to lead to inhibition of cell proliferation and induction of apoptotic cell death.

II. Radioprotective Treatment

The compounds of the invention are also believed to protect normal cells and tissues from the effects of acute and chronic exposure to ionizing radiation.

Individuals may be exposed to ionizing radiation when undergoing therapeutic irradiation for the treatment of proliferative disorders. The compounds are believed effective in protecting normal cells during therapeutic irradiation of abnormal tissues. The compounds are also believed useful in protecting normal cells during radiation treatment for leukemia, especially in the purging of malignant cells from autologous bone marrow grafts with ionizing radiation.

According to the invention, therapeutic ionizing radiation may be administered to an individual on any schedule and in any dose consistent with the prescribed course of treatment, as long as the radioprotectant compound according to the invention is administered prior to the radiation. The course of treatment differs from individual to individual, and those of ordinary skill in the art can readily determine the appropriate dose and schedule of therapeutic radiation in a given clinical situation.

III. Chemoprotective Treatment

In addition, the compounds of Formula IE prepared by the methods disclosed herein are believed to protect normal cells and tissues from the effects of exposure to mitotic phase cell cycle inhibitors and topoisomerase inhibitors.

Mitotic phase cell cycle inhibitors include, by way of example and not limitation, taxanes, such as paclitaxel and its analogs; vinca alkaloids such as vincristine and vinblastine; colchicine; estramustine; and naturally occurring macrolides such as rhizoxin, maytansine, ansamitocin P-3, phomopsin A, dolastatin 10 and halichrondin B.

Paclitaxel is an anti-mitotic drug presently used as an initial treatment for ovarian, breast and lung cancer, with moderate success. Vincristine is a well-established anti-mitotic drug widely used for the treatment of breast cancer, Hodgkin's lymphoma and childhood cancers.

Topoisomerase inhibitors include compounds that inhibit topoisomerase I, compounds that inhibit topoisomerase II, and compounds that inhibit both topoisomerase I and II.

Inhibitors of topoisomerase I include, for example, adriamycin, etoposide, β-lapachone (Calbiochem No. 428022), AG-555 (Calbiochem No. 112270), 10-hydroxycamptothecin (Calbiochem No. 390238), AG-1387 (Calbiochem No. 658520), rebeccamycin (Calbiochem No. 553700), nogalamycin (Calbiochem No. 488200), and topotecan (Calbiochem No. 614800).

Inhibitors of topoisomerase II include, for example, camptothecin, irinotecan and topotecan, amsacrine (Calbiochem No. 171350), aurintricarboxylic acid (Calbiochem No. 189400), bruneomycin (Calbiochem No. 571120), ellipticine (Calbiochem No. 324688), epirubicin (Calbiochem No. 324905), etoposide (Calbiochem No. 341205), genistein (Calbiochem No. 345834), and merbarone (Calbiochem No. 445800).

Inhibitors of both topoisomerase I and II include, for example, aclarubicin (Calbiochem No. 112270), congocidine (Calbiochem No. 480676), daunomycin (Calbiochem No. 251800), ellagic acid (Calbiochem No. 324683), and suramin (Calbiochem No. 574625).

The compounds of the present invention are believed to not only protect normal cells, but are also to be operationally cytotoxic in tumor cells. In normal cells, the cytoprotective compounds of the invention are believed to induce a reversible resting state rendering the normal cells relatively refractory to the cytotoxic effect of mitotic phase cell cycle inhibitors and topoisomerase inhibitors.

VI. Conjugates of Formula I Compounds

Compounds according to Formula I may be reacted to form conjugates with a carrier molecule. The carrier may comprise any molecule sufficiently large to be capable of generating an immune response in an appropriate host animal. One such preferred carrier is keyhole limpet haemocyanin (KLH). Additionally, structural components of substituents on the phenyl or Q rings of compounds of the invention (e.g., as peptidyl substituents) can potentially provide antigenic activity sufficient to raise antibodies to the compounds of Formula I. Alternately, a Formula I compound may be conjugated to an antibody (Ab). Antibodies for conjugation to Formula I compounds preferably comprise monoclonal antibodies and monospecific polyclonal antibodies or fragments thereof, most preferably tumor-specific antibodies, or fragments thereof. The antibody (Ab) may be covalently linked to compounds of Formula I, via a covalent linker (L) to form a conjugate of the Formula I-L-Ab.

The compounds of Formula I can readily be covalently bonded to antibodies, preferably tumor-specific monoclonal antibodies (Mab) via a suitable bifunctional linker (-L-) to yield a conjugate of general Formula, I-L-Ab. A general synthetic route for preparing compounds of the present invention of general Formula I-L-Ab is shown in Scheme 14 of U.S. Patent Application No. 20080058290, incorporated by reference herein in its entirety.

The covalent linker (L) between a compound according to Formula I and an antibody (Ab) to form a conjugate of the Formula I-L-Ab may, in its simplest form, comprise a single covalent bond connecting the compound according to Formula I to the antibody. More commonly, the compound according to Formula I is attached to the antibody using a suitable bifunctional linking reagent. The term "bifunctional linking reagent" refers generally to a molecule that comprises two reactive moieties which are connected by a spacer element. The term "reactive moieties" in this context, refers to chemical functional groups capable of coupling with an antibody or a compound according to Formula I by reacting with functional groups on the antibody and the compound according to Formula I.

An example of a covalent bond formed as a linker between a compound according to Formula I and an antibody is a disulfide bond formed by the oxidation of an antibody and a compound according to Formula I, wherein a substituent on the phenyl ring or Q-ring of Formula I comprises a peptidyl moiety containing one or more cysteine amino acids. The cysteine residues can be oxidized to form disulfide links by dissolving 1 mg of the a suitable compound according to Formula I and 0.5 equivalents of the desired antibody in 1.5 mL of 0.1% (v/v) 17.5 mM acetic acid, pH 8.4, followed by flushing with nitrogen and then 0.01 M $K_2Fe(CN)_6$. After incubation for one hour at room temperature, the adduct peptide is purified, e.g., by HPLC.

Another example of a suitable covalent bond formed as a linker between a compound according to Formula I and an antibody is an amide bond formed by reacting an amino group on a compound of the invention with a carboxylic acid group which forms part of the primary structure of the antibody (Ab) (e.g., for example a glutamic or aspartic amino acid residue). Alternately, an amide bond could be formed if the reacting moieties were reversed, i.e., the compound according to Formula I contains a carboxylic acid functionality and reacts with an amino functionality within the Ab structure.

Alternatively, a compound according to Formula I and an antibody Ab may be covalently linked using a bifunctional linking reagent. In one such embodiment of the present invention, a compound according to Formula I, wherein a substituent on the phenyl ring or Q-ring of Formula I comprises a peptidyl moiety, is coupled to an antibody using a bifunctional linking reagent.

For example, adducts can be prepared by first preparing S—(—N-hexylsuccinimido)-modified derivatives of an antibody and of a compound according to Formula I, according to the method of Cheronis et al., *J Med. Chem.* 37: 348 (1994) (the entire disclosure of which is incorporated herein by reference). N-hexylmaleimide, a precursor for the modified antibody and compound according to Formula I, is prepared from N-(methoxycarbonyl)maleimide and N-hexylamine by mixing the two compounds in saturated $NaHCO_3$ at 0° C. according to the procedure of Bodanszky and Bodanszky, *The Practice of Peptide Synthesis*; Springer-Verlag, New York, pp. 29-31 (1984) (the entire disclosure of which is incorporated herein by reference). The product of the resulting reaction mixture is isolated by extraction into a suitable solvent, e.g., ethyl acetate, followed by washing with water, dried over $Na_2SO_4$. The extract is then concentrated in vacuo to produce N-hexylmaleimide. S—(N-hexylsuccinimido)-modified antibody and Formula I compound are then prepared from a cysteine-containing peptide and N-hexylmaleimide by mixing one part peptide with 1.5 parts N-hexylmaleimide in DMF (3.3 mL/mM peptide) followed by addition to 30 volumes of 0.1 M ammonium bicarbonate, pH 7.5. The S-alkylation reaction carried out in this manner is complete in 30 min. The resulting S—(N-hexylsuccinimido)-modified peptide monomer is purified by preparative reverse-phase HPLC, followed by lyophilization as a fluffy, white powder.

Bis-succinimidohexane peptide heterodimers (wherein one peptide is the antibody and the other peptide is a Formula I compound wherein a substituent on the phenyl or Q ring of Formula I comprises a peptidyl moiety), may be prepared according to the method of Cheronis et al., supra from cysteine-substituted peptides. A mixture of one part bis-maleimidohexane is made with two parts peptide monomer in DMF (3.3 mL/mM peptide) followed by addition to 0.1 ammonium bicarbonate, pH 7.5. The reaction mixture is stirred at room temperature and the reaction is usually complete within 30 min. The resulting bis-succinimidohexane peptide dimer is purified by preparative reverse-phase HPLC. After lyophilization the material is a fluffy, white powder.

Covalently linked adducts of the Formula I-L-Ab may be prepared by utilizing homo-bifunctional linking reagents (wherein the two reactive moieties are the same), such as, for example, disuccinimidyl tartrate, disuccinimidyl suberate, ethylene glycolbis-(succinimidyl succinate), 1,5-difluoro-2,4-dinitrobenzene ("DFNB"), 4,4'-diisothiocyano-2,2'-disulfonic acid stilbene ("DIDS"), and bis-maleimidohexane ("BMH"). The linking reaction occurs randomly between the Ab and a compound according to Formula I having a peptidyl moiety as part of at least on substituent on the phenyl ring or the Q ring of Formula I.

Alternatively, hetero-bifunctional linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimido-methyl)cyclohexane-1-carboxylate ("sulfo-SMCC"), sulfosuccinimidyl 4-(p-maleimidophenyl)- butyrate ("sulfo-SMPB"), bromoacetyl-p-aminobenzoyl-N-hydroxy-succinimidyl ester, iodoacetyl-N-hydroxysuccinimidyl ester, and the like.

For hetero-bifunctional linking, a compound according to Formula I is derivatized with, for example, the N-hydroxysuccinimidyl portion of the bifunctional reagent, and the resulting derivatized compound is purified by chromatography. Next, a suitable antibody is reacted with the second functional group of the bifunctional linking reagent, assuring a directed sequence of binding between components of the desired adduct Typical hetero-bifunctional linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of either the antibody or the Formula I compound are acylated with the NHS-ester group of the cross-linking agent. The remaining component, possessing free sulfhydryl groups, is reacted with the sulfhydryl reactive group of the cross-linking agent to form a covalently cross-linked dimer. Common thiol reactive groups include for example, maleimides, pyridyl disulfides, and active halogens. For example, MBS contains a NHS-ester as the amino reactive group, and a maleimide moiety as the sulfhydryl reactive group.

Photoactive hetero-bifunctional linking reagents, e.g., photoreactive phenyl azides, may also be employed. One such reagent, SASD, may be linked to either an antibody or to a Formula I compound wherein at least one substituent on Q or the phenyl ring of Formula I comprises a peptidyl moiety, via its NHS-ester group. The conjugation reaction is carried out at pH 7 at room temperature for about 10 minutes. Molar ratios between about 1 and about 20 of the cross-linking agent to the compounds to be linked may be used.

Numerous bifunctional linkers, useful as linkers (-L-), exist which have been used specifically for coupling small molecules to monoclonal antibodies, and many of these are commercially available. Examples include N-succinimidyl-3-(2-pyridyldithio)-propionate (SPDP), 2-iminothiolane (2-IT), 3-(4-carboxamidophenyldithio)propionthioimidate (CDPT), N-succinimidyl-acetylthioacetate (SATA), ethyl-S-acetyl-propionthioimidate (AMPT) and N-succinimidyl-3-(4-carboxamidophenyldithio)propionate (SCDP). Procedures for preparation of immunoconjugates using these linkers is detailed in Toxin-Targeted Design for Anticancer Therapy. II: Preparation and Biological Comparison of Different Chemically Linked Gelonin-Antibody Conjugates (Cattel, et al, *J. Pharm. Sci.*, 82:7, p 699-704, 1993), (the entire disclosure of which is incorporated herein by reference).

According to one embodiment of the invention the antibody comprises a tumor-specific antibody, more preferably a tumor-specific monoclonal antibody or a tumor-specific monospecific polyclonal antibody.

Monoclonal antibodies (Mabs) may be advantageously cleaved by proteolytic enzymes to generate fragments retaining the antigen-binding site. For example, proteolytic treatment of IgG antibodies with papain at neutral pH generates two identical so-called "Fab" fragments, each containing one intact light chain disulfide-bonded to a fragment of the heavy chain (Fd). Each Fab fragment contains one antigen-combining site. The remaining portion of the IgG molecule is a dimer known as "Fc". Similarly, pepsin cleavage at pH 4 results in the so-called F(ab')2 fragment.

Methods for preparation of such fragments are known to those skilled in the art. See, Goding, Monoclonal Antibodies Principles and Practice, Academic Press (1983), p. 119-123.

Fragments of the anti-DBF-MAF monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion.

The effects of sensitization in the therapeutic use of animal origin monoclonal antibodies in the treatment of human disease may be diminished by employing a hybrid molecule generated from the same Fab fragment, but a different Fc fragment, than contained in Mab's previously administered to the same subject. It is contemplated that such hybrid molecules formed from the monoclonal antibodies of the invention may be used in therapy. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species.

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, antibodies are produced which are largely human but contain antigen-binding specificities generated in mice. As demonstrated by Morrison et al., *Proc. Natl. Acad. Sci.* USA 81, 6851-6855, 1984, both chimeric heavy chain V region exon (VH)-human heavy chain C region genes and chimeric mouse light chain V region exon (V*)-human * light chain gene constructs may be expressed when transfected into mouse myeloma cell lines. When both chimeric heavy and light chain genes are transfected into the same myeloma cell, an intact $H_2L_2$ chimeric antibody is produced. The methodology for producing such chimeric antibodies by combining genomic clones of V and C region genes is described in the above-mentioned paper of Morrison et al., and by Boulianne et al., *Nature* 312, 642-646, 1984. Also see Tan et al., *J. Immunol.* 135, 3564-3567, 1985 for a description of high level expression from a human heavy chain promotor of a human-mouse chimeric chain after transfection of mouse myeloma cells. As an alternative to combining genomic DNA, cDNA clones of the relevant V and C regions may be combined for production of chimeric antibodies, as described by Whitte et al., *Protein Eng.* 1, 499-505, 1987 and Liu et al., *Proc. Natl. Acad. Sci.* USA 84, 3439-3443, 1987.

For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric anti-DBP-MAF monoclonal antibodies.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., *Nature* 321, 522-525, 1986; Verhoeyen et al., *Science* 239, 1534-1536, 1988; Reichmann et al., 322, 323-327, 1988; Hale et al., *Lancet* 2, 1394-1399, 1988; Queen et al., *Proc. Natl. Acad. Sci.* USA 86, 10029-10033, 1989). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human antibodies of reduced human immunogenicity.

Several such monoclonal antibodies, chimeric animal-human monoclonal antibodies, humanized antibodies and antigen-binding fragments thereof have been made available. Some examples include:

Satumomab Pendetide (by Cytogen, a murine Mab directed against TAG-72);

Igovomab (by CIS Bio, a murine Mab fragment Fab2 directed against tumor-associated antigen CA 125);

Arcitumomab (by Immunomedics, a murine Mab fragment Fab directed against human carcinoembryonic antigen CEA);

Capromab Pentetate (by Cytogen, a murine Mab directed against tumor surface antigen PSMA);

Tecnemab KI (by Sorin, murine Mab fragments (Fab/Fab2 mix) directed against HMW-MAA);

Nofetumomab (by Boehringer Ingelheim/NeoRx, murine Mab fragments (Fab) directed against carcinoma-associated antigen);

Rituximab (by Genentech/IDEC Pharmaceuticals, a chimeric Mab directed against CD20 antigen on the surface of B lymphocytes);

Trastuzumab (by Genintech, a humanized antibody directed against human epidermal growth factor receptor 2 (HER 2));

Votumumab (by Organon Teknika, a human Mab directed against cytokeratin tumor-associated antigen);

Ontak (by Seragen/Ligand Pharmaceuticals, an IL-2-diphtheria toxin fusion protein that targets cells displaying a surface IL-2 receptor);

IMC-C225 (by Imclone, a chimerized monoclonal antibody that binds to EGFR);

LCG-Mab (by Cytoclonal Pharmaceutics Monoclonal antibody directed against lung cancer gene LCG)

ABX-EGF (by Abgenix, a fully human monoclonal antibody against the epidermal growth factor receptor (EGFr)); and Epratuzumab (by Immunomedics, a humanized, anti-CD22 monoclonal antibody).

VII. Salts of Compounds of the Invention

The compounds of the present invention may take the form of salts. The term "salts", embraces salts commonly used to form alkali metal salts and to form addition salts of free acids or free bases. The term "pharmaceutically-acceptable salt" refers to salts which possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, B-hydroxybutyric, salicyclic, galactaric and galacturonic acid. Examples of pharmaceutically unacceptable acid addition salts include, for example, perchlorates and tetrafluoroborates.

Suitable pharmaceutically acceptable base addition salts of compounds of the invention include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. Examples of pharmaceutically unacceptable salts include lithium salts and cyanate salts. All of these salts may be prepared by conventional means from the corresponding compound according to Formula I by reacting, for example, the appropriate acid or base with the compound according to Formula I.

VIII. Administration of Compounds of the Invention

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

One or more compounds useful in the practice of the present inventions may be administered simultaneously, by the same or different routes, or at different times during treatment.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a proliferative disorder will, of course, be determined by the particular circumstances of the individual patient including, the size, weight, age and sex of the patient, the nature and stage of the proliferative disorder, the aggressiveness of the proliferative disorder, and the route of administration of the compound.

For example, a daily dosage of from about 0.05 to about 50 mg/kg/day may be utilized. Higher or lower doses are also contemplated.

A. Radioprotection

The compounds of the invention are further believed useful in the protection of normal cells from the cytotoxic and genetic effects of exposure to radiation, in individuals who have incurred, who will in the future incur and who are at risk for incurring exposure to ionizing radiation.

The specific dose of compound according to the invention to obtain therapeutic benefit for radioprotection will, be determined by the particular circumstances of the individual patient including, the size, weight, age and sex of the patient, the type, dose and timing of the ionizing radiation, and the route of administration of the compound of the invention.

For example, a daily dosage of from about 0.05 to about 50 mg/kg/day may be utilized. Higher or lower doses are also contemplated.

Exposure to radiation by an individual may comprise therapeutic radiation administered to the individual or in some indications, to bone marrow removed from the individual.

An individual may also be exposed to ionizing radiation from occupation or environmental sources, as discussed in the Background of the Invention, above. For purposes of the invention, the source of the radiation is not as important as the type (i.e., acute or chronic) and dose level absorbed by the individual. It is understood that the following discussion encompasses ionizing radiation exposures from both occupational and environmental sources.

Individuals suffering from effects of acute or chronic exposure to ionizing radiation that are not immediately fatal are said to have remediable radiation damage. Such remediable radiation damage can be reduced or eliminated by the compounds and methods of the present invention.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01 Gy) and about 5000 millirem (0.05 Gy) over a period greater than 24 hours, or a localized dose of 15,000 millirem (0.15 Gy) to 50,000 millirem (0.5 Gy) over a period greater than 24 hours.

(i) Radioprotection: Therapeutic Ionizing Radiation

For radioprotective administration to individuals receiving therapeutic ionizing radiation, the compounds of the invention should be administered far enough in advance of the therapeutic radiation such that the compound is able to reach the normal cells of the individual in sufficient concentration to exert a radioprotective effect on the normal cells. The pharmacokinetics of specific compounds may be determined by means known in the art and tissue levels of a compound in a particular individual may be determined by conventional analyses.

The compound may be administered as much as about 24 hours, preferably no more than about 18 hours, prior to administration of the radiation. In one embodiment, the therapy is administered at least about 1, 2, 3, 4, 5, 6, 7, 8, 9, 10, 11 or 12 hours before administration of the therapeutic radiation. Most preferably, the compound is administered once at about 18 hours and again at about 6 hours before the radiation exposure.

One or more compounds of Formula I may be administered simultaneously, or different compounds of Formula I may be administered at different times during the treatment.

Where the therapeutic radiation is administered in serial fashion, it is preferable to intercalate the administration of one or more radioprotective compounds within the schedule of radiation treatments. As above, different radioprotective compounds of the invention may be administered either simultaneously or at different times during the treatment. Preferably, an about 24-hour period separates administration of the radioprotective compound and the therapeutic radiation. More preferably, the administration of the radioprotective compound and the therapeutic radiation is separated by about 6 to 18 hours. This strategy will yield significant reduction of radiation-induced side effects without affecting the anticancer activity of the therapeutic radiation.

For example, therapeutic radiation at a dose of 0.1 Gy may be given daily for five consecutive days, with a two-day rest, for a total period of 6-8 weeks. One or more compounds of Formula I may be administered to the individual 18 hours previous to each round of radiation. It should be pointed out, however, that more aggressive treatment schedules, i.e., delivery of a higher dosage, is contemplated according to the present invention due to the protection of the normal cells afforded by the radioprotective compounds. Thus, the radioprotective effect of the compound increases the therapeutic index of the therapeutic radiation, and may permit the physician to safely increase the dosage of therapeutic radiation above presently recommended levels without risking increased damage to the surrounding normal cells and tissues.

(ii) Radioprotection: Radiation-Treated Bone Marrow

The radioprotective compounds of the invention are further useful in protecting normal bone marrow cells from radiologic treatments designed to destroy hematologic neoplastic cells or tumor cells which have metastasized into the bone marrow. Such cells include, for example, myeloid leukemia cells. The appearance of these cells in the bone marrow and elsewhere in the body is associated with various disease conditions, such as the French-American-British (FAB) subtypes of acute myelogenous leukemias (AML), chronic myeloid leukemia (CML), and acute lymphocytic leukemia (ALL).

CML, in particular, is characterized by abnormal proliferation of immature granulocytes (e.g., neutrophils, eosinophils, and basophils) in the blood, bone marrow, spleen, liver, and other tissues and accumulation of granulocytic precursors in these tissues. The individual who presents with such symptoms will typically have more than 20,000 white blood cells per microliter of blood, and the count may exceed 400,000. Virtually all CML patients will develop "blast crisis", the terminal stage of the disease during which immature blast cells rapidly proliferate, leading to death.

Other individuals suffer from metastatic tumors, and require treatment with total body irradiation (TBI). Because TBI will also kill the individual's hematopoietic cells, a portion of the individual's bone marrow is removed prior to irradiation for subsequent reimplantation. However, metastatic tumor cells are likely present in the bone marrow, and reimplantation often results in a relapse of the cancer within a short time.

Individuals presenting with neoplastic diseases of the bone marrow or metastatic tumors may be treated by removing a portion of the bone marrow (also called "harvesting"), purging the harvested bone marrow of malignant stem cells, and reimplanting the purged bone marrow. Preferably, the individual is treated with radiation or some other anti-cancer therapy before the autologous purged bone marrow is reimplanted.

Thus, the invention provides a method of reducing the number of malignant cells in bone marrow, comprising the steps of removing a portion of the individual's bone marrow, administering an effective amount of at least one radioprotective compound according to the present invention and irradiating the treated bone marrow with a sufficient dose of ionizing radiation such that malignant cells in the bone marrow are killed. As used herein, "malignant cell" means any uncontrollably proliferating cell, such a tumor cell or neoplastic cell. The radioprotective compounds protect the normal hematopoietic cells present in the bone marrow from the deleterious effects of the ionizing radiation. The compounds also exhibit a direct killing effect on the malignant cells. The number of malignant cells in the bone marrow is significantly reduced prior to reimplantation, thus minimizing the occurrence of a relapse.

Preferably, each compound according to Formula I is administered to the bone marrow in a concentration from about 0.25 to about 100 micromolar; more preferably, from about 1.0 to about 50 micromolar; in particular from about 2.0 to about 25 micromolar. Particularly preferred concentrations are 0.5, 1.0 and 2.5 micromolar and 5, 10 and 20 micromolar.

The radioprotective compounds may be added directly to the harvested bone marrow, but are preferably dissolved in an organic solvent such as DMSO. Pharmaceutical formulations of compounds of Formula I, such as are described in more detail below may also be used.

Preferably, the radioprotective compound is added to the harvested bone marrow about 20 hours prior to radiation exposure, preferably no more than about 24 hours prior to radiation exposure. In one embodiment, the radioprotective compound is administered to the harvested bone marrow at least about 6 hours before radiation exposure. One or more compounds may be administered simultaneously, or different compounds may be administered at different times. Other dosage regimens are also contemplated.

If the individual is to be treated with ionizing radiation prior to reimplantation of the purged bone marrow, the individual may be treated with one or more radioprotective compounds prior to receiving the ionizing radiation dose, as described above.

(iii) Radioprotection: Environmental or Occupational Radiation Exposure

The invention also provides a method for treating individuals who have incurred remediable radiation damage from acute or chronic exposure to ionizing radiation, comprising reducing or eliminating the cytotoxic effects of radiation exposure on normal cells and tissues by administering an effective amount of at least one radioprotective compound. The compound is preferably administered in as short a time as possible following radiation exposure, for example between 0-6 hours following exposure.

Remediable radiation damage may take the form of cytotoxic and genotoxic (i.e., adverse genetic) effects in the individual. In another embodiment, there is therefore provided a method of reducing or eliminating the cytotoxic and genotoxic effects of radiation exposure on normal cells and tissues, comprising administering an effective amount of at least one radioprotective compound prior to acute or chronic radiation exposure. The compound may be administered, for example about 24 hours prior to radiation exposure, preferably no more than about 18 hours prior to radiation exposure. In one embodiment, the compound is administered at least about 6 hours before radiation exposure. Most preferably, the compound is administered at about 18 and again at about 6 hours before the radiation exposure. One or more radioprotective compounds may be administered simultaneously, or different radioprotective compounds may be administered at different times.

When multiple acute exposures are anticipated, the radioprotective compounds of the invention may be administered multiple times. For example, if fire or rescue personnel must enter contaminated areas multiple times, radioprotective compounds of the invention may be administered prior to each exposure. Preferably, an about 24-hour period separates administration of the compound and the radiation exposure. More preferably, the administration of radioprotective compounds and the radiation exposure is separated by about 6 to 18 hours. It is also contemplated that a worker in a nuclear power plant may be administered an effective amount of a radioprotective compound of the invention prior to beginning each shift, to reduce or eliminate the effects of exposure to ionizing radiation.

If an individual is anticipating chronic exposure to ionizing radiation, the radioprotective compound may be administered periodically throughout the duration of anticipated exposure. For example, a nuclear power plant worker or a soldier operating in a forward area contaminated with radioactive fallout may be given the radioprotective compound every 24 hours, preferably every 6-18 hours, in order to mitigate the effects of radiation damage. Likewise, the radioprotective compound may be periodically administered to civilians living in areas contaminated by radioactive fallout until the area is decontaminated or the civilians are removed to a safer environment.

B. Chemoprotection

The compounds of the invention are believed useful in protecting individuals from the cytotoxic side effects of mitotic phase cell cycle inhibitors and topoisomerase inhibitors, used in the treatment of cancer and other proliferative disorders.

The specific dose of a compound according to the invention to obtain therapeutic benefit for chemoprotection will be determined by the particular circumstances of the individual patient including, the size, weight, age and sex of the patient, the type and dose of the administered chemotherapy, the nature and stage and cell damage, and the route of administration of the compound of the invention.

For example, a daily dosage of from about 0.05 to about 50 mg/kg/day may be utilized. Higher or lower doses are also contemplated.

For providing cytoprotection from cytotoxic effects of chemotherapeutic agents, the schedule of administration of the cytotoxic drug, i.e., mitotic phase cell cycle inhibitor or topoisomerase inhibitor, can be any schedule with the stipulation that the compound according to Formula I is administered prior to the cytotoxic drug. The cytoprotective compound should be administered far enough in advance of the cytotoxic drug such that the former is able to reach the normal cells of the patient in sufficient concentration to exert a cytoprotective effect on the normal cells. Again, individual drug pharmacokinetics and blood levels of a specific drug in a specific patient are factors that may be determined by methods known in the art.

The cytoprotective compound is administered at least about 1 hour, preferably, at least about 2 hours, and more preferably, at least about 4 hours, before administration of the cytotoxic drug. The compound may be administered as much as about 48 hours, preferably no more than about 36 hours, prior to administration of the cytotoxic drug. Most preferably, the compound is administered about 24 hours before the cytotoxic drug. The compound may be administered more or less than 24 hours before the cytotoxic effect, but the protective effect of the compounds is greatest when administered about 24 hours before the cytotoxic drug. One or more cytotoxic drugs may be administered. Similarly, one or more of the compounds of Formula I may be combined.

Where the cytotoxic drug or drugs is administered in serial fashion, it may prove practical to intercalate cytoprotective compounds of the invention within the schedule with the caveat that a 4-48 hour period, preferably a 12-36 hour period, most preferably a 24 hour period, separates administration of the two drug types. This strategy will yield partial to complete eradication of cytotoxic drug side effects without affecting anticancer activity.

For example, the mitotic inhibitor may be given daily, or every fourth day, or every twenty-first day. The compound according to Formula I may be given 24 hours previous to each round of inhibitor administration, both as a cytoprotective agent and as an antitumor agent.

The compounds of the invention may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical, subcutaneous or sublingual administration. Also contemplated within the scope of the invention is the instillation of drug in the body of the patient in a controlled formulation, with systemic or local release of the drug to occur at a later time. For anticancer use, the drug may be localized in a depot for controlled release to the circulation, or local site of tumor growth. When more than one compound according to Formula I is administered, or when one or more compounds of Formula I are administered in addition to one or more cytotoxic drugs, the different compounds may be administered by the same or different routes.

IX. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The practice of the invention is illustrated by the following non-limiting examples.

Example 1

Design, Synthesis and Biological Evaluation of (E)-Styryl Benzyl Sulfones as Novel Anticancer Agents.

Introduction:

In this Example, the synthesis and Structure Activity Relationship of a group of cytotoxic molecules that selectively induce growth arrest of normal cells in the G1 phase, while inducing a mitotic arrest of tumor cells resulting in selective killing of tumor cell populations with little or no effect on normal cell viability is described. The broad spectrum of anti-tumor activity in vitro and xenograft models, lack of in vivo toxicity and drug resistance suggests potential for use of these agents in cancer therapy.

Materials and Methods:

Chemistry. General methods. All reagents and solvents were obtained from commercial suppliers and used without further purification unless otherwise stated. Solvents were dried using standard procedures and reactions requiring anhydrous conditions were performed under $N_2$ atmosphere. Reactions were monitored by Thin Layer Chromatography (TLC) on precoated silica gel F254 plates (Sigma-Aldrich) with a UV indicator. Column chromatography was performed with Merck 70-230 mesh silica gel 60A°. Yields were of purified product and were not optimized. Melting points were determined using an Electrothermal Mel-Temp® 3.0 micro melting point apparatus and are uncorrected. $^1$H NMR and $^{13}$C NMR spectra were obtained with a Bruker AM 300 and 400 MHz spectrometer. The chemical shifts are reported in parts per million (δ) downfield using tetramethyl silane ($Me_4Si$) as internal standard and CDCl3 as the solvent except where indicated. Spin multiplicities are given as s (singlet), d (doublet), br s (broad singlet), m (multiplet), and q (quartet). Coupling constants (J values) were measured in hertz (Hz). Combustion analyses were performed with a Perkin-Elmer 2402 series II CHNS/O analyzer by Quantitative Technologies Inc. White House, N.J. All the compounds gave satisfactory combustion analysis results (C, H, N within 0.4% of calculated values). Benzylsulfonylacetic acids were prepared according to the procedure reported in the literature.[13]

General Procedure for the Preparation of (E)-Styryl Benzyl Sulfones (6):

Method A (Scheme 1):

A mixture of benzylsulfonyl acetic acid 4 (10 mmol), araldehyde 5 (10 mmol), acetic acid (10 mL), and a catalytic amount of benzylamine (150 μL) was refluxed for about 2-8 h. After completion of the reaction (TLC monitoring, CHCl$_3$ on silica gel plate), cooled the contents to room temperature, the precipitated product was filtered and washed with 2-propanol. If solid was not formed, the reaction mixture was diluted with ether, washed with saturated NaHCO$_3$, dilute hydrochloric acid and water. The organic layer was dried over sodium sulfate, filtered and concentrated under vacuum to obtain the desired crude product 6. The crude product was recrystallized in 2-propanol, to yield an analytically pure sample of 6. The following (E)-styryl benzyl sulfones 6 were prepared using the above procedure.

(E)-4-Methoxystyryl-4-Methoxybenzyl sulfone (6a). The title compound was obtained from 4-methoxybenzylsulfonylacetic acid and 4-methoxybenzaldehyde following the procedure as described in method A. Yield: 51%; white solid, mp 150-152° C. $^1$H NMR: δ 3.65 (s, 3H, OCH$_3$), 3.68 (s, 3H, OCH$_3$), 4.07 (s, 2H, CH$_2$), 6.36 (d, 1H, J=14.4 Hz, =CH), 6.71-6.76 (m, 4H, Ar—H), 7.09-7.22 (m, 5H, Ar—H+ vinylic). Anal. (C$_{17}$H$_{18}$O$_4$S): C, H.

(E)-4-Fluorostyryl-4-Methoxybenzyl sulfone (6b). The title compound was obtained from 4-methoxybenzylsulfonylacetic acid and 4-fluorobenzaldehyde following the procedure as described in method A. Yield: 60%; white solid, mp 148-149° C. $^1$H NMR: δ 3.81 (s, 3H, OCH$_3$), 4.25 (s, 2H, CH$_2$), 6.61 (d, 1H, J=14.0 Hz, =CH), 6.91-7.45 (m, 9H, Ar—H+ vinylic). Anal. (C$_{16}$H$_{15}$FO$_3$S): C, H.

(E)-4-Chlorostyryl-4-Methoxybenzyl sulfone (6c). The title compound was obtained from 4-methoxybenzylsulfonylacetic acid and 4-chlorobenzaldehyde following the procedure as described in method A. Yield: 66%; white solid, mp 176-177° C. $^1$H NMR: δ 3.56 (s, 3H, OCH$_3$), 4.00 (s, 2H, CH$_2$), 6.40 (d, 1H, J=16.0 Hz, =CH), 6.63-7.14 (m, 9H, Ar—H+ vinylic). Anal. (C$_{16}$H$_{15}$ClO$_3$S): C, H.

(E)-4-Nitrostyryl-4-Methoxybenzyl sulfone (6d). The title compound was obtained from 4-methoxybenzylsulfonylacetic acid and 4-nitrobenzaldehyde following the procedure as described in method A. Yield: 56%; light yellow solid, mp 179-181° C. $^1$H NMR: δ 3.76 (s, 3H, OCH$_3$), 4.24 (s, 2H, CH$_2$), 6.78 (d, 1H, J=15.6 Hz, =CH), 6.84 (m, 2H, Ar—H), 7.20-7.24 (m, 2H, Ar—H), 7.41 (d, 1H, J=15.6 Hz, CH=), 7.52 (d, 2H, J=13.3 Hz, Ar—H), 8.19 (d, 2H, J=11.1 Hz, Ar—H). Anal. (C$_{16}$H$_{15}$NO$_5$S): C, H, N.

(E)-4-Aminostyryl-4-Methoxybenzyl sulfone (6e). In a 100 mL round-bottomed flask fitted with condenser, 5% Pd/C (0.073 g) was taken and 20 mL ethanol was added slowly. Compound 6d (0.5 g, 1.4 mmol) and hydrazine hydrate (1.24 g, 38.7 mmol) were added to the content of the flask and refluxed for 6 h. Completion of the reaction was monitored by TLC (CHCl$_3$ on silica gel plate), filtered the reaction mixture through celite and concentrated the reaction mixture to 50% volume. The concentrated mixture was poured onto crushed ice, the solid formed was filtered, washed with cooled water, dried to get the desired product 6e. Yield: 52%; light yellow solid mp 164-168° C. $^1$H NMR: δ 3.80 (s, 3H, OCH$_3$), 4.22 (s, 2H, CH$_2$), 4.04 (br s, 2H, NH$_2$), 6.42 (d, 1H, J=15.6 Hz, =CH), 6.60-7.31 (m, 9H, Ar—H+ vinylic). Anal. (C$_{16}$H$_{17}$NO$_3$S): C, H, N.

(E)-2-Methoxystyryl-4-Methoxybenzyl sulfone (6f). The title compound was obtained from 4-methoxybenzylsulfonylacetic acid and 2-methoxybenzaldehyde following the procedure as described in method A. Yield: 53%; white solid mp 115-117° C. $^1$H NMR: δ 3.75 (s, 3H, OCH$_3$), 3.81 (s, 3H, OCH$_3$), 4.18 (s, 2H, CH$_2$), 6.82-7.27 (m, 9H, Ar—H+ vinylic) 7.56 (d, 1H, J=15.6 Hz, CH=). Anal. (C$_{17}$H$_{18}$O$_4$S): C, H.

(E)-2-Chloro-4-fluorostyryl-4-Methoxybenzyl sulfone (6g). The title compound was obtained from 4-methoxybenzylsulfonylacetic acid and 2-chloro-4-fluorobenzaldehyde following the procedure as described in method A. Yield: 56%; white solid mp 154-155° C. $^1$H NMR: δ 3.75 (s, 3H, OCH$_3$), 4.22 (s, 2H, CH$_2$), 6.62 (d, 1H, J=15.6 Hz, =CH), 6.83-7.41 (m, 7H, Ar—H), 7.68 (d, 1H, J=15.6 Hz). Anal. (C$_{16}$H$_{14}$ClFO$_3$S): C, H.

(E)-2,4-Dimethylstyryl-4-Methoxybenzyl sulfone (6h). The title compound was obtained from 4-methoxybenzylsulfonylacetic acid and 2,4-dimethylbenzaldehyde following the procedure as described in method A. Yield: 55%; white solid mp 126-128° C. $^1$H NMR: δ 2.21 (s, 3H, CH$_3$), 2.27 (s, 3H, CH$_3$), 3.74 (s, 3H, OCH$_3$), 4.19 (s, 2H, CH$_2$), 6.49 (d, 1H, J=15.4 Hz, =C), 6.83-7.24 (m, 7H, Ar—H), 7.55 (d, 1H, J=15.4 Hz). Anal. (C$_{18}$H$_{20}$O$_3$S): C, H.

(E)-4-Fluoro-3-methoxystyryl-4-Methoxybenzylsulfone (6i). The title compound was obtained from 4-methoxybenzylsulfonylacetic acid and 4-fluoro-3-methoxybenzaldehyde following the procedure as described in method A. Yield: 55%; white solid mp 105-107° C. $^1$H NMR: δ 3.69 (s, 3H, OCH$_3$), 3.75 (s, 3H, OCH$_3$), 4.20 (s, 2H, CH$_2$), 6.55 (d, 1H, J=15.5 Hz, =CH), 6.82-7.31 (m, 8H, Ar—H+ vinylic). Anal. (C$_{17}$H$_{17}$FO$_4$S): C, H.

(E)-3,4-Dimethoxystyryl-4-Methoxybenzyl sulfone (6j). The title compound was obtained from 4-methoxybenzylsulfonylacetic acid and 3,4-dimethoxybenzaldehyde following the procedure as described in method A. Yield: 54%; white solid mp 160-161° C. $^1$H NMR: δ 3.23 (s, 3H, OCH$_3$), 3.55 (s, 3H, OCH$_3$), 3.81 (s, 3H, OCH$_3$), 4.37 (s, 2H, CH$_2$), 6.71 (d, 1H, J=15.4 Hz, =CH), 6.64-7.05 (m, 7H, Ar—H), 7.55 (d, 1H, J=15.4 Hz). Anal. (C$_{18}$H$_{20}$O$_5$S): C, H.

(E)-3,5-Dimethylstyryl-4-Methoxybenzyl sulfone (6k). The title compound was obtained from 4-methoxybenzylsulfonylacetic acid and 3,5-dimethylbenzaldehyde following the procedure as described in method A. Yield: 58%; white solid mp 127-130° C. $^1$H NMR: δ 2.08 (s, 6H, 2×CH$_3$), 3.57 (s, 3H, OCH$_3$), 3.99 (s, 2H, CH$_2$), 6.40 (d, 1H, J=15.5 Hz, =CH), 6.83-7.24 (m, 7H, Ar—H), 7.11 (d, 1H, J=15.5 Hz). Anal. (C$_{18}$H$_{20}$O$_3$S): C, H.

(E)-2,6-Dimethylstyryl-4-Methoxybenzyl sulfone (6l). The title compound was obtained from 4-methoxybenzylsulfonylacetic acid and 2,6-dimethylbenzaldehyde following the procedure as described in method A. Yield: 53%; white solid mp 99-101° C. $^1$H NMR: δ 2.15 (s, 3H, CH$_3$), 2.27 (s, 3H, CH$_3$), 3.75 (s, 3H, OCH$_3$), 4.13 (s, 2H, CH$_2$), 6.41 (d, 1H, J=15.4 Hz, =CH), 6.83-7.35 (m, 7H, Ar—H), 7.55 (d, 1H, J=15.4 Hz). Anal. (C$_{18}$H$_{20}$O$_3$S): C, H.

(E)-2,6-Dimethoxystyryl-4-Methoxybenzyl sulfone (6m). The title compound was obtained from 4-methoxybenzylsulfonylacetic acid and 2,6-dimethoxybenzaldehyde following the procedure as described in method A. Yield: 51%; white solid mp 136-138° C. $^1$H NMR: δ 3.81 (s, 3H, OCH$_3$), 3.85 (s, 3H, OCH$_3$), 3.91 (s, 3H, OCH$_3$), 4.23 (s, 2H, CH$_2$), 7.19 (d, 1H, J=15.4 Hz, =CH), 6.64-7.05 (m, 7H, Ar—H), 7.90 (d, 1H, J=15.4 Hz). $^{13}$C NMR: δ 160.6, 160.3, 135.9, 132.9.9, 132.6, 126.4, 120.9, 114.5, 110.7, 104.0, 61.7, 56.2, 55.7. Anal. (C$_{18}$H$_{20}$O$_5$S): C, H.

(E)-2,4-Dimethoxystyryl-4-Methoxybenzyl sulfone (6n). The title compound was obtained from 4-methoxybenzylsulfonylacetic acid and 2,4-dimethoxybenzaldehyde following the procedure as described in method A. Yield: 59%; white solid mp 161-162° C. $^1$H NMR: δ 3.73 (s, 3H, OCH$_3$), 3.77 (s, 6H, 2×OCH₃), 4.14 (s, 2H, CH₂), 6.71 (d, 1H, J=15.5 Hz, =CH), 6.37-7.23 (m, 7H, Ar—H), 7.42 (d, 1H, J=15.5 Hz). Anal. (C$_{18}$H$_{20}$O$_5$S): C, H.

(E)-2,5-Dimethoxystyryl-4-Methoxybenzyl sulfone (6o). The title compound was obtained from 4-methoxybenzylsulfonylacetic acid and 2,5-dimethoxybenzaldehyde following the procedure as described in method A. Yield: 54%; white solid mp 105-107° C. ¹H NMR: δ 3.71 (s, 3H, OCH₃), 3.75 (s, 3H, OCH₃), 3.76 (s, 3H, OCH₃), 4.18 (s, 2H, CH₂), 6.78-7.26 (m, 8H, Ar—H+ vinylic), 7.52 (d, 1H, J=15.6 Hz). Anal. (C$_{18}$H$_{20}$O$_5$S): C, H.

(E)-3,5-Dimethoxystyryl-4-Methoxybenzyl sulfone (6p). The title compound was obtained from 4-methoxybenzylsulfonylacetic acid and 3,5-dimethoxybenzaldehyde following the procedure as described in method A. Yield: 62%; white solid mp 119-121° C. ¹H NMR: δ 3.70 (s, 6H, 2×OCH₃), 3.71 (s, 3H, OCH₃), 4.15 (s, 2H, CH₂), 6.55 (d, 1H, J=15.5 Hz, =CH), 6.42-7.20 (m, 7H, Ar—H), 7.23 (d, 1H, J=15.5 Hz). Anal. (C$_{18}$H$_{20}$O$_5$S): C, H.

(E)-2,4,5-Trimethoxystyryl-4-Methoxybenzyl sulfone (6q). The title compound was obtained from 4-methoxybenzylsulfonylacetic acid and 2,4,5-trimethoxy-benzaldehyde following the procedure as described in method A. Yield: 66%; white solid mp 146-148° C. ¹H NMR: δ 3.73 (s, 3H, OCH₃), 3.78 (s, 6H, 2×OCH₃), 3.81 (s, 3H, OCH₃), 4.20 (s, 2H, CH₂), 6.86 (m, 4H, Ar—H), 7.00 (d, 1H, J=15.6 Hz, =CH), 7.31 (d, 2H, J=8.9 Hz), 7.61 (d, 1H, J=15.6 Hz, CH=). Anal. (C$_{19}$H$_{22}$O$_6$S): C, H.

(E)-2,3,4-Trimethoxystyryl-4-Methoxybenzyl sulfone (6r). The title compound was obtained from 4-methoxybenzylsulfonylacetic acid and 2,3,4-trimethoxy-benzaldehyde following the procedure as described in method A. Yield: 54%; white solid mp 154-156° C. ¹H NMR: δ 3.75 (s, 3H, OCH₃), 3.79 (s, 6H, 2×OCH₃), 3.83 (s, 3H, OCH₃), 4.18 (s, 2H, CH₂), 6.76 (d, 2H, J=8.9 Hz, Ar—H), 6.86 (d, 2H, J=9.0 Hz, Ar—H), 6.99 (d, 1H, J=15.6 Hz, =CH), 7.31 (d, 2H, J=8.9 Hz), 7.61 (d, 1H, J=15.6 Hz, CH=). Anal. (C$_{19}$H$_{22}$O$_6$S): C, H.

(E)-2,4,6-Trimethoxystyryl-4-Methoxybenzyl sulfone (6s). The title compound was obtained from 4-methoxybenzylsulfonylacetic acid and 2,4,6-trimethoxy-benzaldehyde following the procedure as described in method A. Yield: 34%; white solid mp 143-145° C. ¹H NMR: δ 3.80 (s, 3H, OCH₃), 3.82 (s, 6H, 2×OCH₃), 3.85 (s, 3H, OCH₃), 4.20 (s, 2H, CH₂), 6.08 (s, 2H, Ar—H), 6.88 (d, 2H, J=9.2 Hz, Ar—H), 7.00 (d, 1H, J=15.6 Hz, =CH), 7.31 (d, 2H, J=8.8 Hz), 7.81 (d, 1H, J=15.6 Hz, CH=). ¹³C NMR: δ 164.2, 161.8, 160.2, 135.9, 132.6, 123.0, 121.1, 114.4, 104.2, 90.9, 61.8, 56.1, 55.8, 55.6. Anal. (C$_{19}$H$_{22}$O$_6$S): C, H.

(E)-3,4,5-Trimethoxystyryl-4-Methoxybenzyl sulfone (6t). The title compound was obtained from 4-methoxybenzylsulfonylacetic acid and 3,4,5-trimethoxy-benzaldehyde following the procedure as described in method A. Yield: 54%; white solid mp 138-141° C. ¹H NMR: δ 3.76 (s, 3H, OCH₃), 3.80 (s, 6H, 2×OCH₃), 3.83 (s, 3H, OCH₃), 4.16 (s, 2H, CH₂), 6.78 (d, 2H, J=9.1 Hz, Ar—H), 6.91 (d, 2H, J=8.9 Hz, Ar—H), 7.04 (d, 1H, J=15.6 Hz, =CH), 7.37 (d, 2H, J=8.8 Hz), 7.79 (d, 1H, J=15.6 Hz, CH=). Anal. (C$_{19}$H$_{22}$O$_6$S): C, H.

(E)-2,6-Dimethoxy-4-hydroxystyryl-4-Methoxybenzyl sulfone (6u). The title compound was obtained from 4-methoxybenzylsulfonylacetic acid and 2,6-dimethoxy-4-hydroxybenzaldehyde following the procedure as described in method A. Yield: 58%; white solid mp 134-136° C. ¹H NMR: δ 3.47 (s, 6H, 2×OCH₃), 3.55 (s, 3H, OCH₃), 3.98 (s, 2H, CH₂), 5.77 (s, 2H, Ar—H), 6.63 (d, 2H, J=8.5 Hz, Ar—H), 6.73 (d, 1H, J=15.6 Hz, =CH), 7.05 (d, 2H, J=8.5 Hz), 7.55 (d, 1H, J=15.6 Hz, CH=). Anal. (C$_{18}$H$_{20}$O$_6$S): C, H.

Preparation of 4-Fluoro-2,6-dimethoxybenzaldehyde: Phosphorous oxychloride (1.8 mL, 19.3 mmol) was added slowly to a well-stirred mixture of 1-fluoro-3,5-dimethoxy benzene (2.6 mL, 19.25 mmol) and N,N-dimethylformamide (2.5 mL, 20 mmol) while temperature was kept below −5° C. Stirring was continued at room temperature for 1.5 h and at 60° C. for another 2 h. Reaction completion was monitored by TLC. The reaction mixture was cooled and hydrolyzed with ice-water (60 mL). The resulting suspension was neutralized by addition of 5N NaOH, extracted with ethyl acetate (2×30 mL), the aqueous phase was adjusted to pH 10 by 5N NaOH and re-extracted with ethyl acetate (2×30 mL). The combined organic phases were washed with saturated aqueous NaHCO₃ solution (30 mL) and brine (30 mL) and dried over anhydrous sodium sulfate. The dried solution was concentrated to get the crude product which on purification by column chromatography afforded a colorless pure product. Yield: 75%; white solid mp 79-81° C. ¹H NMR: δ 3.85 (s, 3H, OCH₃), 3.89 (s, 3H, OCH₃), 6.25 (S, 2H, Ar—H), 10.24 (s, 1H, CHO). Anal. Calcd for C$_{18}$H$_{19}$FO$_5$S: C, 58.70, H, 4.92. Found: C, 58.64, H, 4.91.

(E)-2,6-Dimethoxy-4-fluorostyryl-4-Methoxybenzyl sulfone (6v). The title compound was obtained from 4-methoxybenzylsulfonylacetic acid and 2,6-dimethoxy-4-fluorobenzaldehyde following the procedure as described in method A. Yield: 55%; white solid mp 146-148° C. ¹H NMR: δ 3.47 (s, 6H, 2×OCH₃), 3.55 (s, 3H, OCH₃), 3.98 (s, 2H, CH₂), 5.77 (s, 2H, Ar—H), 6.63 (d, 2H, J=8.5 Hz, Ar—H), 6.73 (d, 1H, J=15.6 Hz, =CH), 7.05 (d, 2H, J=8.5 Hz), 7.55 (d, 1H, J=15.6 Hz, CH=). Anal. (C$_{18}$H$_{19}$FO$_5$S): C, H.

(E)-2,4,6-Trimethylstyryl-4-Methoxybenzyl sulfone (6w). The title compound was obtained from 4-methoxybenzylsulfonylacetic acid and 2,4,6-trimethylbenzaldehyde following the procedure as described in method A. Yield: 51%; white solid mp 97-99° C. ¹H NMR: δ 2.16 (s, 3H, CH₃), 2.28 (s, 6H, 2×CH₃), 3.76 (s, 3H, OCH₃), 4.13 (s, 2H, CH₂), 6.08 (s, 2H, Ar—H), 6.42 (d, 1H, J=15.4 Hz, =CH), 6.82 (m, 4H, Ar—H), 7.56 (d, 1H, J=15.4 Hz, CH=). Anal. (C$_{19}$H$_{22}$O$_3$S): C, H.

(E)-2,4,6-Trimethoxystyryl-4-Trifluoromethoxybenzyl sulfone (6x). The title compound was obtained from 4-trifluoromethoxybenzylsulfonylacetic acid and 2,4,6-trimethoxybenzaldehyde following the procedure as described in method A. Yield: 52%; white solid mp 133-135° C. ¹H NMR: δ 3.82 (s, 6H, 2×OCH₃), 3.87 (s, 3H, OCH₃), 4.26 (s, 2H, CH₂), 6.10 (s, 2H, Ar—H), 6.99 (d, 1H, J=15.6 Hz, =CH), 7.20-7.48 (m, 4H, Ar—H), 7.78 (d, 1H, J=15.6 Hz, CH=). Anal. (C$_{19}$H$_{19}$F$_3$O$_6$S): C, H.

(E)-3,4,5-Trimethoxystyryl-3-Hydroxy-4-Methoxybenzyl Sulfone (6y). The title compound was obtained from 3-hydroxy-4-methoxybenzylsulfonylacetic acid and 3,4,5-trimethoxybenzaldehyde following the procedure as described in method A. Yield: 60%; white solid mp 118-120° C. ¹H NMR: δ 3.83 (s, 6H, 2×OCH₃), 3.85 (s, 3H. OCH₃), 3.89 (s, 3H. OCH₃), 4.16 (s, 2H, CH₂), 5.60 (s, 1H, OH), 6.09 (s, 2H, Ar—H), 6.82-6.96 (m, 3H, Ar—H), 7.05 (d, 1H, J=15.6 Hz, =CH), 7.85 (d, 1H, J=15.6 Hz, CH=). Anal. (C$_{19}$H$_{22}$O$_7$S): C, H.

(E)-2,6-Dimethoxy-4-hydroxystyryl-3-Hydroxy-4-Methoxybenzyl Sulfone (6z). The title compound was obtained from 3-hydroxy-4-methoxybenzylsulfonylacetic acid and 2,6-dimethoxy-4-hydroxybenzaldehyde following the procedure as described in method A. Yield: 54%; white solid mp 123-125° C. ¹H NMR: δ 3.77 (s, 6H, 2×OCH₃), 3.81 (s, 3H, OCH₃), 4.28 (s, 2H, CH₂), 6.10 (s, 2H, Ar—H), 6.71-6.92 (m, 3H, Ar—H), 7.00 (d, 1H, J=15.5 Hz, =CH), 7.59 (d, 1H, J=15.5 Hz, CH=). Anal. ($C_{18}H_{20}O_7S$): C, H.

(E)-2,4,6-Trimethoxystyryl-3-Hydroxy-4-Methoxybenzyl Sulfone (6aa). The synthesis of the title compound was described in the preparation of 20 (Scheme 3). Yield: 63%; white solid mp 125-127° C. $^1$H NMR: δ 3.83 (s, 6H, 2×OCH$_3$), 3.85 (s, 3H. OCH$_3$), 3.89 (s, 3H. OCH$_3$), 4.16 (s, 2H, CH$_2$), 5.60 (s, 1H, OH), 6.09 (s, 2H, Ar—H), 6.82-6.96 (m, 3H, Ar—H), 7.05 (d, 1H, J=15.6 Hz, =CH), 7.85 (d, 1H, J=15.6 Hz, CH=). $^{13}$C NMR: δ 164.1, 161.9, 147.3, 145.9, 135.7, 123.4, 123.1, 122.2, 117.5, 111.1, 105.5, 104.4, 90.9, 62.0, 56.3, 56.1, 55.8. Anal. ($C_{19}H_{22}O_7S$): C, H.

(E)-2,4,6-Trimethoxystyryl-3$^1$-O-phosphate disodium-4-methoxybenzyl Sulfone (6ab). The synthesis of the title compounds was described in the preparation of 29 (Scheme 5). Yield: 98%; white solid mp 152-154° C. $^1$H NMR (D$_2$O): δ 3.68 (s, 6H, 2×OCH$_3$), 3.71 (s, 3H. OCH$_3$), 3.78 (s, 3H. OCH$_3$), 4.35 (s, 2H, CH$_2$), 5.92 (s, 2H, Ar—H), 6.91 (s, 2H, Ar—H), 6.97 (d, 1H, J=15.6 Hz, =CH), 7.39 (s, 1H, Ar—H), 7.43 (d, 1H, J=15.6 Hz, CH=). $^{13}$C NMR (D$_2$O): δ 164.4, 161.7, 151.1, 143.8, 136.8, 125.9, 123.4, 120.6, 120.2, 113.1, 103.4, 91.1, 61.0, 56.4, 56.2, 55.9. Anal. ($C_{19}H_{21}O_{10}Na_2PS$): C, H.

(E)-2,4,6-trimethoxystyryl-3,4,5-Trimethoxybenzyl sulfone (6ac). The title compound was obtained from 3,4,5-trimethoxybenzylsulfonylacetic acid and 2,4,6-trimethoxybenzaldehyde following the procedure as described in method A. Yield: 53%; white solid mp 151-153° C. $^1$H NMR: δ 3.81 (s, 6H, 2×OCH$_3$), 3.83 (s, 6H, 2×OCH$_3$), 3.84 (s, 3H, OCH$_3$), 3.85 (s, 3H, OCH$_3$), 4.19 (s, 2H, CH$_2$), 6.10 (s, 2H, ArH), 6.60 (s, 2H, ArH), 7.03 (d, 1H, J=15.6 Hz, =CH), 7.83 (d, 1H, J=15.6 Hz, CH=). Anal. ($C_{21}H_{26}O_8S$): C, H.

(E)-2,4,6-Trimethoxystyryl-2,3,4-Trimethoxybenzyl sulfone (6ad). The title compound was obtained from 2,3,4-trimethoxybenzylsulfonylacetic acid and 2,4,6-trimethoxybenzaldehyde following the procedure as described in method A. Yield: 52%; white solid mp 94-96° C. $^1$H NMR: δ 3.77, 3.83, 3.84, 3.86, 3.90 (s, 6×3H, OCH$_3$), 4.32 (s, 2H, CH$_2$), 6.08 (s, 2H, aromatic), 6.67 (d, J=8.4 Hz, 1H, aromatic), 7.11 (d, J=15.6 Hz, 1H, =CH), 7.16 (d, J=8.4 Hz, 1H, aromatic), 7.79 (d, J=15.6 Hz, 1H, CH=). Anal. ($C_{21}H_{26}O_8S$): C, H.

(E)-2,4,6-trimethoxystyryl-4-chlorobenzyl sulfone (6ae). The title compound was obtained from 4-chlorobenzylsulfonylacetic acid and 2,4,6-trimethoxybenzaldehyde following the procedure as described in method A. Yield: 60%; white solid mp 181-184° C. $^1$H NMR: δ 3.83 (s, 2×3H, OCH$_3$), 3.85 (s, 3H, OCH$_3$), 4.22 (s, 2H, CH$_2$), 6.09 (s, 2H, Ar—H), 6.99 (d, 1H, J=15.5 Hz, =CH), 7.29 (s, 4H, Ar—H), 7.76 (d, 1H, J=15.5 Hz, CH=). Anal. ($C_{18}H_{19}ClO_5S$): C, H.

(E)-2,4,6-trimethoxystyryl-4-Nitrobenzyl sulfone (6af). The title compound was obtained from 4-nitrobenzylsulfonylacetic acid and 2,4,6-trimethoxybenzaldehyde following the procedure as described in method A. Yield: 60%; light yellow solid mp 179-184° C. $^1$H NMR: δ 3.83 (s, 2×3H, OCH$_3$), 3.86 (s, 3H, OCH$_3$), 4.35 (s, 2H, CH$_2$), 6.09 (s, 2H, Ar—H), 7.01 (d, 1H, J=15.5 Hz, =CH), 7.57 (d, 2H, J=9.0 Hz, Ar—H), 7.76 (d, J=15.5 Hz, 1H, CH=), 8.21 (d, 2H, J=9.0 Hz, Ar—H). Anal. ($C_{18}H_{19}NO_7S$): C, H, N.

(E)-2,4,6-trimethoxystyryl-4-Cyanobenzyl sulfone (6ag). The title compound was obtained from 4-cyanobenzylsulfonylacetic acid and 2,4,6-trimethoxybenzaldehyde following the procedure as described in method A. Yield: 58%; white solid mp 140-142° C. $^1$H NMR: δ 3.81 (s, 3H, 2×OCH$_3$), 3.87 (s, 3H, OCH$_3$), 4.21 (s, 2H, CH$_2$), 6.00 (s, 2H, Ar—H), 6.78 (d, 2H, J=8.5 Hz, Ar—H), 7.07 (d, 1H, J=15.6 Hz, =CH), 7.29 (d, 2H, J=8.5 Hz, Ar—H), 7.86 (d, 1H, J=15.6 Hz, CH=). Anal. ($C_{19}H_{19}NO_5S$): C, H, N.

(E)-2,4,6-trimethoxystyryl-4-Carboxybenzyl sulfone (6ah). The title compound was obtained from 4-carboxybenzylsulfonylacetic acid and 2,4,6-trimethoxy-benzaldehyde following the procedure as described in method A. Yield: 60%; white solid mp 143-145° C. $^1$H NMR: δ 3.83 (s, 2×OCH$_3$), 3.88 (s, 3H, OCH$_3$), 4.11 (s, 2H, CH$_2$), 6.01 (s, 2H, Ar—H), 6.68 (d, 2H, J=8.5 Hz, Ar—H), 6.97 (d, 1H, J=15.6 Hz, =CH), 7.13 (d, 2H, J=8.5 Hz, Ar—H), 7.76 (d, 1H, J=15.6 Hz, CH=). Anal. ($C_{19}H_{20}O_7S$): C, H.

(E)-2,4,6-trimethoxystyryl-4-Hydroxybenzyl sulfone (6ai). The title compound was obtained from 4-tert-Butoxybenzylsulfonylacetic acid and 2,4,6-trimethoxy-benzaldehyde following the method A procedure. During the condensation the protective tert-butoxy group cleaved to hydroxy group. Yield: 52%; white solid mp 141-143° C. $^1$H NMR: δ 3.73 (s, 6H, 2×OCH$_3$), 3.77 (s, 3H, OCH$_3$), 4.11 (s, 2H, CH$_2$), 4.36 (s, 1H, OH), 6.01 (s, 2H, Ar—H), 6.68 (d, 2H, J=8.5 Hz, Ar—H), 6.97 (d, 1H, J=15.6 Hz, =CH), 7.13 (d, 2H, J=8.5 Hz, Ar—H), 7.76 (d, 1H, J=15.6 Hz, CH=). Anal. ($C_{15}H_{20}O_6S$): C, H.

Method B (Scheme 2):

Preparation of Phenacyl Benzyl Sulfones (10). General Procedure

To a cooled solution of sodium hydroxide (100 mmol) in absolute methanol (50 mL), taken in a 250 mL round-bottomed flask, benzyl thiol 7 (100 mmol) was added slowly through a dropping funnel and the reaction mixture was stirred for 5 min. An appropriate phenacyl bromide 8 (100 mmol) was added in portions to the contents of the flask and stirred for 3-4 h. After completion of the reaction, the contents of the flask were poured into crushed ice and the compound formed was washed with ice-cold water and dried to get phenacyl benzyl sulfide 9.

The above crude phenacyl benzyl sulfide 9 (50 mmol) in glacial acetic acid (100 ml) was taken in a 250 mL round-bottomed flask and 30% hydrogen peroxide (60 mL) was added in portions at frequent intervals. Then the reaction mixture was stirred at room temperature for 24 h. The solid, if any formed was separated by filtration and the filtrate was poured onto crushed ice. The compound separated was filtered, washed with water, dried and added to the first crop, if any. The total product on recrystallization from methanol afforded pure phenacyl benzyl sulfone (10).

4-Methoxyphenacyl-4-methoxybenzyl sulfone (10a). The title compound was obtained from 4-methoxybenzyl thiol and 4-methoxyphenacyl bromide followed by oxidation of the resultant compound. Yield: 80%; white solid mp 128-130° C. $^1$H NMR: δ 3.78 (s, 3H, OCH$_3$), 3.88 (s, 3H, OCH$_3$), 4.60 (s, 2H, CH$_2$), 4.89 (s, 2H, CH$_2$), 6.98 (d, 2H, J=8.7 Hz, Ar—H), 7.09 (d, 2H, J=8.9 Hz, Ar—H), 7.36 (d, 2H, J=8.7 Hz, Ar—H), 8.04 (d, 2H, J=8.9 Hz, Ar—H). Anal. Calcd for $C_{17}H_{18}O_5S$: C, 61.06, H, 5.42. Found: C, 61.09, H, 5.40.

4-Chlorophenacyl-4-methoxybenzyl sulfone (10b). The title compound was obtained from 4-methoxybenzyl thiol and 4-chlorophenacyl bromide followed by oxidation of the resultant compound. Yield: 82%; white solid mp 141-143° C. $^1$H NMR: δ 3.89 (s, 3H, OCH$_3$), 4.50 (s, 2H, CH$_2$), 4.79 (s, 2H, CH$_2$), 7.06 (d, 2H, J=8.3 Hz, Ar—H), 7.47 (d, 2H, J=8.4 Hz, Ar—H), 7.60 (dd, 4H, J=8.2, 9.4 Hz, Ar—H). Anal. Calcd for $C_{16}H_{15}ClO_4S$: C, 56.72, H, 4.46. Found: C, 56.69, H, 4.42.

Preparation of β-Hydroxy Benzyl Sulfones (11). General Procedure

To an ethanolic solution (20 mL) of phenacyl benzyl sulfone 10 (10 mmol) maintained at 0° C., was added NaBH$_4$ (10 mmol) slowly under N$_2$ atmosphere. The reaction mixture was maintained at 0° C. for 0.5 h. After completion of the reaction, monitored by TLC, the contents were poured on to crushed ice. The solid separated out was filtered, washed with water and dried under vacuum to yield 11.

2-(4-Methoxybenzylsulfonyl)-1-(4-methoxyphenyl)ethanol (11a). The title compound was obtained by the reduction of 10a with sodium borohydride. Yield: 70%; white solid mp 112-114° C. $^1$H NMR: δ 3.43 (dd, 2H, J=9.9 and 4.6 Hz), 3.76 (s, 3H, OCH$_3$), 3.78 (s, 3H, OCH$_3$), 4.47 (dd, 2H, J=15.7 and 13.6 Hz), 5.09 (m, 1H, CHOH), 6.00 (d, 1H, J=4.2 Hz, OH), 6.93 (d, 2H, J=8.6 Hz, Ar—H), 6.99 (d, 2H, J=8.6 Hz, Ar—H), 7.35 (t, 4H, J=8.8 Hz, Ar—H). Anal. Calcd for C$_{17}$H$_{20}$O$_5$S: C, 60.69, H, 5.99. Found: C, 60.73, H, 5.97.

1-(4-Chlorophenyl)-2-(4-methoxybenzylsulfonyl)ethanol (11b). The title compound was obtained by the reduction of 10b with sodium borohydride. Yield: 78%; white solid mp 130-132° C. $^1$H NMR: δ 3.63 (dd, 2H, J=10.1 and 4.4 Hz),), 3.93 (s, 3H, OCH$_3$), 4.75 (dd, 2H, J=13.5 and 10.6 Hz), 5.26 (d, 1H, J=8.3 Hz, CHOH), 6.17 (br s, 1H, OH), 7.10 (d, 2H, J=8.3 Hz, Ar—H), 7.51 (d, 2H, J=8.3 Hz, Ar—H), 7.64 (dd, 4H, J=9.4 and 8.2 Hz, Ar—H). Anal. Calcd for C$_{16}$H$_{17}$ClO$_4$S: C, 56.39, H, 5.03. Found: C, 56.34, H, 4.99.

Preparation of (E)-Styryl Benzyl Sulfones (6).

p-Toluenesulfonic acid (1 mmol) was added in one portion to a mixture of β-hydroxy benzyl sulfone 11 (5 mmol) in anhydrous benzene (25 mL) at room temperature under N$_2$ atmosphere. The temperature was raised to 80° C., and the mixture was refluxed for 3 h using Dean-Stark water separator. After completion of the reaction monitored by TLC, the reaction mixture was concentrated under reduced pressure and then quenched by the addition of water (25 mL). The aqueous layer was neutralized with a saturated aqueous solution of sodium hydrogen carbonate and extracted with dichloromethane (3×25 mL). The combined organic extracts were washed with brine (2×25 mL) dried over Na$_2$SO$_4$, filtered and the solvent was evaporated under reduced pressure to afford crude product, which on recrystallization in 2-propanol afforded the desired product 6 in excellent yield.

(E)-4-Methoxystyryl-4-Methoxybenzyl sulfone (6a). The title compound was obtained by dehydration of 11a as described in the above procedure. Yield: 65%; white solid, mp 151-153° C. Analytical data is same as 6a obtained by method A.

(E)-4-Chlorostyryl-4-Methoxybenzyl sulfone (6c). The title compound was obtained by dehydration of 11b as described in the above procedure. Yield: 69%; white solid, mp 175-177° C. Analytical data is same as 6c obtained by method A.

Synthesis of (E)-2,4,6-Trimethoxystyryl-3-Hydroxy-4-Methoxybenzyl Sulfone, 6aa: (Scheme 3)

Preparation of 3-[(tert-Butyldimethylsilyl)oxy]-4-methoxybenzaldehyde (13)

To a cooled solution of 3-hydroxy-4-methoxybenzaldehyde 12 (10.0 g, 65.7 mmol) in dry N,N-dimethyl formamide (75 mL) was added diisopropylethylamine (16.99 g, 131.4 mmol). Before the addition of 1.0 M solution of tert-butyldimethylsilyl chloride in tetrahydrofuran (11.89 g or 78.9 mL, 78.85 mmol) the mixture was stirred under nitrogen for 10 min. After complete addition over 30 min, the reaction mixture was left overnight (12-16 h). Reaction completion was checked by TLC (chloroform on silica gel plate). Water was added to the reaction mixture, extracted with dichloromethane and the organic layer was washed with a saturated sodium bicarbonate solution, water and dried. Removal of solvent in vacuo yielded as an oil which was subjected to column chromatography (eluant: chloroform) to afford as an yellow viscous oil 13 (100%). $^1$H NMR: δ 0.21 (s, 6H, 2×CH$_3$), 1.01 (s, 9H, 3×CH$_3$), 3.91 (s, 3H, OCH$_3$), 6.94 (d, 1H, J=8.5 Hz, 5H), 7.36 (d, 1H, J=2 Hz, 2H), 7.47 (dd, 1H, J=8.5, 2 Hz, 6H), 9.89 (s, 1H, CHO). Anal. Calcd for C$_{14}$H$_{22}$O$_3$Si: C, 63.12, H, 8.32. Found: C, 63.09, H, 8.30.

Preparation of 3-[(tert-Butyldimethylsilyl)oxy]-4-methoxybenzyl Alcohol (14)

To a cooled solution of 3-[(tert-Butyldimethylsilyl)oxy]-4-methoxybenzaldehyde 13 (17.5 g, 65.7 mmol) in methanol (100 mL) under nitrogen, sodium borohydride (2.98 g, 78.8 mmol) was added and stirred at room temperature for 30 min. After the reaction was complete as indicated by TLC (chloroform on silica gel plate), ice was added to the reaction mixture and extracted with ethyl acetate. The organic layer was separated, washed with water and dried. Removal of solvent in vacuo yielded on yellow oil 14 (73.5%). $^1$H NMR: δ 0.18 (s, 6H, 2×CH$_3$), 1.00 (s, 9H, 3×CH$_3$), 1.90 (br s, 1H, OH), 3.82 (s, 3H, OCH$_3$), 4.56 (s, 2H, CH$_2$OH), 6.94 (br s, 3H, Ar—H). Anal. Calcd for C$_{14}$H$_{24}$O$_3$Si: C, 62.64, H, 9.01. Found: C, 62.59, H, 9.03.

Preparation of 3-[(tert-Butyldimethylsilyl)oxy]-4-methoxybenzyl Chloride (15)

To a cooled solution of 3-[(tert-Butyldimethylsilyl)oxy]-4-methoxybenzyl alcohol 14 (9.5 g, 35.4 mmol) in benzene (50 mL) under nitrogen, thionyl chloride (6.32 g or 3.87 mL, 53.1 mmol) dissolved in benzene (5 mL) was added over 10 min and maintained the temperature at 0° C. for 2 h. The completion of reaction was checked by TLC (chloroform on silica gel plate). Ice was added to the reaction mixture and the solution was extracted with ethylacetate. The organic layer was washed with saturated bicarbonate solution and water and dried over anhydrous sodium sulfate. Removal of the solvent in vacuo afforded 15. Yield: 98.5%; yellow oil. $^1$H NMR: δ 0.16 (s, 6H, 2×CH$_3$), 1.00 (s, 9H, 3×CH$_3$), 3.80 (s, 3H, OCH$_3$), 4.44 (s, 2H, CH$_2$), 6.70-7.01 (m, 3H, Ar—H). Anal. Calcd for C$_{14}$H$_{23}$ClO$_2$Si: C, 58.62, H, 8.08. Found: C, 58.69, H, 8.03.

Preparation of 3-[(tert-Butyldimethylsilyl)oxy]-4-methoxybenzylthio acetic acid (16)

To a solution of sodium hydroxide (2.79 g, 69.7 mmol) in methanol (30 mL) was added mercaptoacetic acid (3.21 g or 2.42 mL, 34.9 mmol) slowly and stirred under nitrogen for 10 minutes. 3-[(tert-Butyldimethylsilyl)oxy]-4-methoxybenzyl chloride 15 (10.0 g, 34.9 mmol) was added slowly to the reaction mixture and stirred at room temperature for 3 h. Reaction completion was checked by TLC (chloroform on silica gel plate). The reaction mixture was then poured into ice and neutralized with concentrated HCl. The resulting material was extracted with ethyl acetate. The ethyl acetate solution was washed with water and dried over anhydrous sodium sulfate. Removal of the solvent in vacuo afforded 16. Yield: 75%; white solid mp 57-59° C. $^1$H NMR: δ 0.18 (s, 6H, 2×CH$_3$), 1.02 (s, 9H, 3×CH$_3$), 3.34 (s, 2H, CH$_2$), 3.84 (s, 3H, OCH$_3$), 4.04 (s, 2H, CH$_2$), 6.80-7.01 (m, 3H, Ar—H). Anal. Calcd for C$_{16}$H$_{26}$O$_4$SiS: C, 56.10, H, 7.65. Found: C, 56.08, H, 7.61.

Preparation of 3-Hydroxy-4-methoxybenzylthio acetic acid (17)

To a cooled solution of 3-[(tert-Butyldimethylsilyl)oxy]-4-methoxybenzylthio acetic acid 16 (8.75 g, 25.5 mmol) in tetrahydrofuran (40 mL) was added 1.0 M solution of tetra-n-butyl ammonium fluoride in tetrahydrofuran (6.68 g or 25.54 mL, 25.5 mmol) slowly and stirred under nitrogen for 2 h at room temperature. The progress of the reaction was monitored by TLC (9:1—chloroform:methanol on silica gel plate). Water was added to the reaction mixture and extracted with ethyl acetate. The organic layer was washed with water and dried. Removal of the solvent in vacuo yielded a semi solid that was subjected to column chromatography (initial with chloroform and finally with ethyl acetate) afforded the pure product 17. Yield: 50%; white solid mp 128-130° C. $^1$H NMR: δ 3.34 (s, 2H, $CH_2$), 3.84 (s, 3H, $OCH_3$), 4.04 (s, 2H, $CH_2$), 6.80-7.01 (m, 3H, Ar—H). Anal. Calcd for $C_{10}H_{12}O_4S$: C, 52.62, H, 5.30. Found: C, 52.58, H, 5.35.

Preparation of 3-Hydroxy-4-methoxybenzylsulfonyl acetic acid (18)

To a solution of 3-Hydroxy-4-methoxybenzylthio acetic acid 17 (2.9 g, 12.7 mmol) in glacial acetic acid (15 mL) was added 6 mL 30% hydrogen peroxide and stirred over night (18 h). The completion of the reaction was determined by TLC. The mixture was then poured into ice water and extracted with ethyl acetate. The organic layer was washed with water and dried. Removal of the solvent in vacuo afforded pure product 18. Yield: 60%; white solid mp 164-165° C. $^1$H NMR: δ 3.84 (s, 3H, $OCH_3$), 4.04 (s, 2H, $CH_2$), 4.29 (s, 2H, $CH_2$), 6.85-7.11 (m, 3H, Ar—H). Anal. Calcd for $C_{10}H_{12}O_6S$: C, 46.15, H, 4.65. Found: C, 46.21, H, 4.69.

Preparation of (E)-2,4,6-Trimethoxystyryl-3-Hydroxy-4-Methoxybenzyl Sulfones (20, 6aa)

A mixture of 3-hydroxy-4-methoxy benzyl sulfonyl acetic acid 18 (1.9 g, 7.3 mmol), 2,4,6-trimethoxybenzaldehyde 19 (1.58 g, 8.0 mmol), benzoic acid (0.134 g, 1.1 mmol) and piperidine (0.081 g, 0.95 mmol) in toluene (50 mL) was refluxed for 2-3 h with continuous removal of water using a Dean-Stark water separator. Reaction completion was determined by TLC (9:1 chloroform:methanol on silica gel plate). The reaction mixture was then cooled to room temperature, water was added and extracted with ethyl acetate. The organic layer was washed with saturated sodium bicarbonate solution, dilute hydrochloric acid, water and dried. Removal of the solvent in vacuo yielded a crude product which on recrystallization from 2-propanol resulted pure product 20/6aa.

Alternate Method for the Synthesis of (E)-2,4,6-Trimethoxystyryl-3-Hydroxy-4-Methoxybenzyl Sulfone 6aa (Scheme 4)

Preparation of 3-[(p-Toluenesulfonyl)oxy]-4-methoxybenzaldehyde (21)

A mixture of 3-hydroxy-4-methoxybenzaldehyde 12 (5.0 g, 32 mmol) and p-toluenesulfonyl chloride (10.0 g, 52.5 mmol) was dissolved in pyridine (12.5 mL, 154 mmol). The reaction mixture stirred for 5 min and maintained at 70-80° C. The clear reaction mixture becomes turbid and becomes slurry. The stirring was continued for a period of 2 h at 70-80° C. The reaction completion was determined by TLC and the contents of the flask were cooled to room temperature and poured in to cold water. The white crystalline solid formed was filtered, washed successively with 5 mL 1:1 $HCl:H_2O$, 5 mL of 5% NaOH solution and water till the filtrate is free from pyridine, dried to constant weight to get the desired product 21. Yield: 98%; white solid mp 148-151° C. $^1$H NMR: δ 2.40 (s, 3H, $CH_3$), 3.71 (S, 3H, $OCH_3$), 6.91-7.83 (m, 7H, Ar—H), 9.83 (s, 1H, CHO). Anal. Calcd for $C_{15}H_{14}O_5S$: C, 58.81, H, 4.61. Found: C, 58.79, H, 4.59.

Preparation of 3-[(p-Toluenesulfonyl)oxy]-4-methoxybenzyl Alcohol (22)

To a cooled solution of 3-[(p-Toluenesulfonyl)oxy]-4-methoxybenzaldehyde 21 (9.0 g, 29 mmol) in methanol (25 mL) was added sodium borohydride (0.55 g, 14.5 mmol) in methanol (2.5 mL) over a period of 5-10 min maintaining the temperature around 15-20° C. The reaction mixture was maintained at that temperature for further 30 min and checked TLC for completion of the reaction. Water was added to the reaction mixture and the solid formed was filtered, washed with water and dried to afford 22. Yield: 97%; white solid mp 88-90° C. $^1$H NMR: δ 2.41 (s, 3H, $CH_3$), 3.59 (s, 3H, $OCH_3$), 4.57 (s, 2H, $CH_2$), 6.80-7.79 (m, 7H, Ar—H). Anal. Calcd for $C_{15}H_{16}O_5S$: C, 58.43, H, 5.23. Found: C, 58.49, H, 5.19.

Preparation of 3-[(p-Toluenesulfonyl)oxy]-4-methoxybenzyl Chloride (23)

To a cooled solution of 3-[(p-Toluenesulfonyl)oxy]-4-methoxybenzyl alcohol 22 (8.0 g, 26 mmol) in benzene (25 mL) was added thionyl chloride (1.9 mL, 26 mmol) slowly over a period of 5-10 min maintaining the temperature around 15-20° C. The reaction was maintained at those conditions for 2 h and checked TLC for the completion. The flask is connected to a high vacuum through a trap containing formic acid under mild heating to remove excess thionyl chloride. The slurry formed after complete removal of thionyl chloride and benzene, filtered, washed with hexane and dried to afford 23. Yield: 90%; white solid mp 102-105° C. $^1$H NMR: δ 2.43 (s, 3H, $CH_3$), 3.61 (s, 3H, $OCH_3$), 4.50 (s, 2H, $CH_2$), 6.80-7.79 (m, 7H, Ar—H). Anal. Calcd for $C_{15}H_{15}ClO_4S$: C, 55.13, H, 4.63. Found: C, 53.20, H, 4.59.

Preparation of 3-[(p-Toluenesulfonyl)oxy]-4-methoxybenzylthio acetic acid (24)

To a solution of sodium hydroxide (1.72 g, 42.9 mmol) in methanol (30 mL) was added mercaptoacetic acid (1.5 mL, 21.5 mmol) in portions and stirred under nitrogen atmosphere for 10 min. 3-[(p-Toluenesulfonyl)oxy]-4-methoxybenzyl chloride 23 (7.0 g, 21.5 mmol) was then added slowly to the reaction mixture and stirred at reflux temperature for 5 h. The reaction mixture was then poured into ice containing concentrated HCl. The white crystalline solid separated was filtered, washed with water and dried to get the desired product 24. Yield: 93%; white solid mp 116-120° C. $^1$H NMR: δ 2.41 (s, 3H, $CH_3$), 3.03 (s, 2H, $SCH_2$), 3.61 (s, 3H, $OCH_3$), 3.79 (s, 2H, $CH_2S$), 6.80-7.81 (m, 7H, Ar—H). Anal. Calcd for $C_{17}H_{18}O_6S_2$: C, 53.39, H, 4.74. Found: C, 53.33, H, 4.71.

Preparation of 3-[(p-Toluenesulfonyl)oxy]-4-methoxybenzylsulfonyl acetic acid (25)

To a solution of 3-[(p-Toluenesulfonyl)oxy]-4-methoxybenzylthio acetic acid 24 (7.0 g, 18.4 mmol) in glacial acetic acid (35 mL) was added 21 mL 30% hydrogen peroxide and stirred over night (18 h). The reaction mixture was poured into ice water and the solid separated was filtered, washed with cold water and dried to get pure 25. Yield: 80%; white solid mp 142-146° C. $^1$H NMR: δ 2.50 (s, 3H, CH$_3$), 3.61 (s, 3H, OCH$_3$), 4.03 (s, 2H, SCH$_2$), 4.60 (s, 2H, CH$_2$S), 7.09-7.74 (m, 7H, Ar—H), 13.4 (br s, 1H, OH). Anal. Calcd for C$_{17}$H$_{18}$O$_8$S$_2$: C, 49.27, H, 4.38. Found: C, 49.22, H, 4.34.

Preparation of (E)-2,4,6-Trimethoxystyryl-3-[(p-Toluenesulfonyl)oxy]-4-Methoxy-benzyl Sulfone (26)

A mixture of 3-[(p-Toluenesulfonyl)oxy]-4-methoxybenzylsulfonyl acetic acid 25 (6.0 g, 14.5 mmol), 2,4,6-trimethoxybenzaldehyde 19 (2.85 g, 14.5 mmol), benzoic acid (0.27 g, 2.2 mmol) and piperidine (0.19 mL, 1.9 mmol) in benzene (50 mL) was refluxed for 4-5 h with continuous removal of water using a Dean-Stark water separator. The reaction completion was checked by TLC (9:1 chloroform:methanol on silica gel plate). The reaction mixture was then cooled to room temperature and the crystalline solid formed was filtered, washed with cold benzene and dried to get the desired product 26. Yield: 65%; white solid mp 159-166° C. $^1$H NMR: δ 2.42 (s, 3H, CH$_3$), 3.61 (s, 3H. OCH$_3$), 3.81 (s, 3H, 3×OCH$_3$), 4.21 (s, 2H, CH$_2$), 6.06 (s, 2H, Ar—H), 6.80-7.74 (m, 7H, Ar—H), 7.01 (d, 1H, J=15.5 Hz, =CH), 7.83 (d, 1H, J=15.5 Hz, CH=). Anal. Calcd for C$_{26}$H$_{28}$O$_9$S$_2$: C, 56.90, H, 5.14. Found: C, 56.83, H, 5.11.

Preparation of (E)-2,4,6-Trimethoxystyryl-3-Hydroxy-4-Methoxybenzyl Sulfone (6aa)

A mixture of (E)-2,4,6-Trimethoxystyryl-3-[(p-Toluenesulfonyl)oxy]-4-methoxy-benzyl sulfones 26, (5.0 g, 9.1 mmol), 50 mL (20%) sodium hydroxide solution and methanol (50 mL) were taken in a round bottomed flask and refluxed until the reaction mixture is clear without any turbidity (3-4 h). The progress of the reaction was monitored by TLC. The reaction mixture was cooled to room temperature and neutralized with cold dilute HCl solution. The precipitate separated after neutralization was filtered, washed with water and dried to get the crude product which on recrystallization from 2-propanol resulted analytically pure sample 6aa. Yield: 95%; white solid mp 124-127° C.

Synthesis of (E)-2,4,6-Trimethoxystyryl-3-O-phosphate disodium-4-methoxybenzyl Sulfone (6ab): (Scheme 5)

Preparation of (E)-2,4,6-Trimethoxystyryl-3-O-Bis (benzyl)phosphoryl-4-methoxybenzyl Sulfone (27)

To a stirred solution of (E)-2,4,6-Trimethoxystyryl-3-Hydroxy-4-methoxybenzyl Sulfone 6aa (3.8 g, 9.6 mmol) in acetonitrile (48 mL) under nitrogen atmosphere was added carbon tetrabromide (3.88 g, 11.72 mmol) and triethylamine (1.46 g, 14.4 mmol) and stirring was continued for 10 min. Dibenzyl phosphite (3.20 g, 11.6 mmol) dissolved in acetonitrile (32 mL) was added to the reaction mixture slowly. After the addition, the reaction mixture was stirred for 2 h, checked the TLC for completion of the reaction. The phosphorylation was terminated by drop wise addition of potassium dihydrogen phosphate (20 mL, 0.5 M) to the reaction mixture over a period of 10 min. The solution was then extracted with ethyl acetate (3×60 mL). The organic extracts were combined and washed with water, dried and concentrated in vacuo. The thick liquid obtained after concentration was purified on silica column using chloroform:methanol with increasing polarity. The purified product was concentrated in vacuo to afford pure dibenzyl ester 27. Yield: 73%; semi solid. $^1$H NMR: δ 3.68 (s, 6H, 2×OCH$_3$), 3.71 (s, 3H, OCH$_3$), 3.74 (s, 3H, OCH$_3$), 4.07 (s, 2H, CH$_2$), 4.96-5.04 (m, 4H, OCH$_2$), 5.98 (s, 2H, Ar—H), 6.60-7.42 (m, 14H, Ar—H+vinylic), 7.71 (d, 1H, J=15.6 Hz, CH=). Anal. Calcd for C$_{33}$H$_{35}$O$_{10}$PS: C, 60.54, H, 5.39. Found: C, 60.48, H, 5.44.

Preparation of (E)-2,4,6-Trimethoxystyryl-3-O-phosphoryl-4-methoxybenzyl Sulfone (28)

To a stirred solution of the above dibenzyl ester 27 (4.36 g, 6.7 mmol) in anhydrous dichloromethane (40 mL) under nitrogen at 0° C., was added bromotrimethylsilane (2.14 g, 14.1 mmol). The stirring was continued for 45 min at the same temperature and checked the TLC for completion of the reaction. Sodium thiosulfate (1%, 50 mL) was added to the reaction mixture and stirring was continued for an additional 5 min. The separated aqueous phase was extracted with ethyl acetate (3×25 mL). The organic extracts were concentrated in vacuo to afford the crude phosphoric acid 28, which was purified on a silica column using chloroform:methanol with increasing polarity. The purified product was concentrated in vacuo to afford pure acid 28. Yield: 44.3%; White solid mp 202-205° C. $^1$H NMR (DMSO-d$_6$): δ 3.78 (s, 6H, 2×OCH$_3$), 3.85 (s, 3H, OCH$_3$), 3.86 (s, 3H, OCH$_3$), 4.34 (s, 2H, CH$_2$), 6.30 (s, 2H, Ar—H), 7.02 (m, 2H, Ar—H), 7.12 (d, 1H, J=15.6 Hz, =CH), 7.32 (s, 2H, OH), 7.52 (s, 1H, Ar—H), 7.61 (d, 1H, J=15.6 Hz, CH=). Anal. Calcd for C$_{19}$H$_{23}$O$_{10}$PS: C, 48.10, H, 4.89. Found: C, 48.14, H, 4.92.

Preparation of (E)-2,4,6-Trimethoxystyryl-3$^1$-o-phosphate disodium-4-methoxy-benzyl Sulfone (6ab)

To a stirred solution of the above phosphoric acid 28 (1.35 g, 2.85 mmol) in ethylene glycol dimethyl ether (125 mL) was added 2N sodium hydroxide (0.27 g dissolved in 13.66 mL H$_2$O, 6.8 mmol) and stirred for 3 h. The solid formed was filtered, washed with acetone (2×25 mL) and dried under vacuum to get the product 6ab. Yield: 98%; white solid mp 152-154° C. $^1$H NMR (D$_2$O): δ 3.68 (s, 6H, 2×OCH$_3$), 3.71 (s, 3H. OCH$_3$), 3.78 (s, 3H. OCH$_3$), 4.35 (s, 2H, CH$_2$), 5.92 (s, 2H, Ar—H), 6.91 (s, 2H, Ar—H), 6.97 (d, 1H, J=15.6 Hz, =CH), 7.39 (s, 1H, Ar—H), 7.43 (d, 1H, J=15.6 Hz, CH=). $^{13}$C NMR (D$_2$O): δ 164.4, 161.7, 151.1, 143.8, 136.8, 125.9, 123.4, 120.6, 120.2, 113.1, 103.4, 91.1, 61.0, 56.4, 56.2, 55.9. Anal. (C$_{19}$H$_{21}$O$_{10}$Na$_2$PS): C, H.

Biology

Tissue Culture and Reagents: Paclitaxel was purchased from Sigma. Cell lines were purchased from ATCC. Cell lines were routinely grown in DMEM or RPM1 (CellGro) supplemented with 10% fetal bovine serum (Atlas) and 1 unit/mL penicillin-streptomycin (Gibco).

Cytotoxicity Assay

A number of tumor cell lines were tested using a dose response end point assay system. The cells were grown in either DMEM or RPMI supplemented with 10% fetal bovine serum and 1 unit/mL Penicillin-Streptomycin solution. The tumor cells were plated into 6 well dishes at a cell density of 1.0×10$^5$ cells/mL/well and compounds were added 24 h later at various concentrations. Cell counts were determined from duplicate wells after 96 h of treatment. The total number of viable cells was determined by trypan blue exclusion.

Soft Agar Assay

The soft agar plates were prepared as described by Cosenza, et al (Cosenza, S. C. et al. In Cell Growth, Differentiation and Senescence, Studzinski, G. P., Ed.; Oxford University Press: 1999, 161-176.). Briefly, Noble bottom agar (0.8%) was plated onto 60 mm tissue culture plates. Exponentially growing MIA-PaCa-2 cells ($1.0 \times 10^5$) were mixed with growth medium with various concentrations of each compound and mixed with Noble agar to a final concentration of 0.4%. Each concentration was plated in triplicate. The top agar was allowed to solidify and the plates were then incubated at 5% $CO_2$ at 37° C. for 3 weeks. The plates were then stained with 0.05% nitroblue tetrazolium (NBT) solution and representative plates were photographed using an Olympus stereoscope mounted with a Sony digital camera system (DKC5000, Sony Inc).

Flow Cytometry

Human prostate tumor cells, DU145 cells, and normal diploid human lung fibroblasts, HFL-1 cells, were grown in DMEM (Cellgro) supplemented with 10% fetal bovine serum and 1 unit/mL penicillin-streptomycin. The cells were plated onto 100 $mm^2$ dishes at a cell density of $1.0 \times 10^6$ cells/dish, and 24 h later, they were treated with 2.5 µM of the compound. The cells were harvested 24, 48 and 72 h after treatment. The cells were removed from the plate by trypsin digestion and combined with the non-attached cells found in the medium. The cell pellets were washed in phosphate buffered saline (PBS), and fixed in ice cold 70% ethanol for at least 24 h. The fixed cells were then washed with room temperature PBS and stained with propidium iodide (50 µg/mL) and RNase A (0.5 mg) for 30 min at 37° C. The stained cells were then analyzed on a Becton-Dickinson (BD) (FACScan) flow cytometer and the data analyzed by cell cycle analysis software (Modfit, BD).

PARP Western

BT20 cells were plated at a density of $3.0 \times 10^6$ cells per 150 $mm^2$ plate and treated 24 h later with either DMSO or 6aa. The cells were collected at the indicated time points and cell pellets were frozen. The frozen cell pellets were lysed in 1% NP40/PBS lysis buffer containing protease inhibitors. Equal amounts of total cellular protein was then resolved on a 10%-SDS-polyacrylamide gel. The gels were transferred onto nitrocellulose paper (S/S), hybridized with anti-PARP antibodies (BD) and developed using ECL (Perkin-Elmer, MA) solution.

Nude Mouse Assay

Female athymic (NCR-nu/nu, Taconic) nude mice were injected with $0.5-1.0 \times 10^7$ BT20 cells subcutaneously in the hind leg using a 1 mL tuberculin syringe equipped with a 27 1/2 gauge needle. Approximately 14 days later, mice were paired (N=8) and injected with 6ab or Phosphate buffered saline as the vehicle control. The intravenous injections were performed in the mouse tail vein using a 1 mL tuberculin syringe equipped with a 30 gauge needle. The animals were injected following a $Q_2D \times 3$ schedule. Tumor measurements (two dimensions) were done three times per week using traceable digital vernier calipers (Fisher). Tumor volume was calculated using the following equation: $V=(L \times (S^2) \pi/6$, where L is the longer and S is the shorter of the two dimensions. Body weight was determined during each measurement. The animals were observed for signs of toxicity. The time of tumor volume doubling was calculated and the T-C value (difference in the average times post treatment for tumors of the treated groups to attain a doubling in volume compared to the average of the control group) was determined. Body weight loss of more than 10% was not observed in any group nor were there any animal deaths. All studies were performed under the guidelines of Temple University IACUC.

Bone Marrow Harvest and Colony Formation Assay

Bone marrow was harvested from femur and tibia of CD-1 mice injected with 200 µL of PBS or 6ab [10 mg/mL:100 mg/kg dose] at 12, 24, or 48 h before the sacrifice. The bone marrow cells were cultured in Methylcellulose medium supplemented with 50 ng/mL rmStem Cell Factor, 10 ng/mL rmIL-3, 10 ng/mL rh IL-6, 200 µg/mL human Transfeffin, and 3 units/mL rhErythropoietin (Stem Cell Technologies, Vancouver, BC, Canada). Cultures were seeded in duplicates using 35 mm plastic petri dishes and colony forming units were determined after one week.

Results

Structure-Activity Relationships (SAR)

Following the synthesis of this group of compounds, their in vitro cytotoxicity was assessed using four different human tumor cell lines derived from human breast (BT20), prostate (DU145), lung (H157) and colorectal (DLD1) cancers. The results of this study are presented in Table 1. These studies show that the cytotoxic activity of the styryl benzyl sulfones is completely dependent on the nature and position of the substituents on the two aromatic rings. In a majority of the compounds described here, a methoxy group was kept constant at the $4^{th}$ position on the aromatic ring of the benzyl moiety. A moderate cytotoxic activity was seen when a fluorine atom was present at 4-position (6b) on the styryl aromatic ring. Changing the

TABLE 1

In Vitro Cytotoxicity of Styryl Benzyl Sulfones

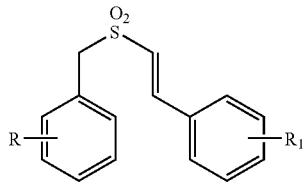

| compd | R | R1 | BT20 $IC_{50}$ (µM) | DU145 $IC_{50}$ (µM) | H157 $IC_{50}$ (µM) | DLD1 $IC_{50}$ (µM) |
|---|---|---|---|---|---|---|
| 6a | 4-OMe | 4-OMe | >20 | >20 | >20 | >20 |
| 6b | 4-OMe | 4-F | 1.5 | 1.25 | 2.5 | 2.0 |
| 6c | 4-OMe | 4-Cl | 2.0 | 2.5 | 3.5 | 3.0 |
| 6d | 4-OMe | 4-$NO_2$ | 5.0 | 7.5 | 7.5 | 5.0 |

TABLE 1-continued

In Vitro Cytotoxicity of Styryl Benzyl Sulfones

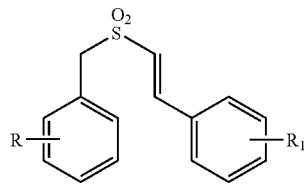

| compd | R | R1 | BT20 IC$_{50}$ (μM) | DU145 IC$_{50}$ (μM) | H157 IC$_{50}$ (μM) | DLD1 IC$_{50}$ (μM) |
|---|---|---|---|---|---|---|
| 6e | 4-OMe | 4-NH$_2$ | >20 | >20 | >20 | >20 |
| 6f | 4-OMe | 2-OMe | 5.0 | 3.5 | 5.0 | 7.5 |
| 6g | 4-OMe | 2-Cl,4-F | 2.5 | 2.0 | 2.5 | 4 |
| 6h | 4-OMe | 2,4-(CH$_3$)$_2$ | 15 | 12 | 15 | 15 |
| 6i | 4-OMe | 2-OMe,4-F | 15 | 10 | 20 | 15 |
| 6j | 4-OMe | 3,4-(OMe)$_2$ | >20 | >20 | >20 | >20 |
| 6k | 4-OMe | 3,5-(CH$_3$)$_2$ | >20 | >20 | >20 | >20 |
| 6l | 4-OMe | 2,6-(CH$_3$)$_2$ | >20 | >20 | >20 | >20 |
| 6m | 4-OMe | 2,6-(OMe)$_2$ | 0.40 | 0.25 | 0.70 | 0.70 |
| 6n | 4-OMe | 2,4-(OMe)$_2$ | >20 | >20 | >20 | >20 |
| 6o | 4-OMe | 2,5-(OMe)$_2$ | >20 | >20 | >20 | >20 |
| 6p | 4-OMe | 3,5-(OMe)$_2$ | >20 | >20 | >20 | >20 |
| 6q | 4-OMe | 2,4,5-(OMe)$_3$ | >20 | >20 | >20 | >20 |
| 6r | 4-OMe | 2,3,4-(OMe)$_3$ | >20 | >20 | >20 | >20 |
| 6s | 4-OMe | 2,4,6-(OMe)$_3$ | 0.020 | 0.025 | 0.030 | 0.040 |
| 6t | 4-OMe | 3,4,5-(OMe)$_3$ | >20 | >20 | >20 | >20 |
| 6u | 4-OMe | 2,6-(OMe)$_2$,4-OH | >20 | >20 | >20 | >20 |
| 6v | 4-OMe | 2,6-(OMe)$_2$,4-F | 0.75 | 0.5 | 0.5 | 0.75 |
| 6w | 4-OMe | 2,4,6-(CH$_3$)$_3$ | >20 | >20 | >20 | >20 |
| 6x | 4-OCF$_3$ | 2,4,6-(OMe)$_3$ | 3 | 4 | 6 | 4 |
| 6y | 4-OMe,3-OH | 3,4,5-(OMe)$_3$ | 7.5 | 5 | 10 | 10 |
| 6z | 4-OMe,3-OH | 2,6-(OMe)$_2$,4-OH | 0.25 | 0.5 | 0.5 | 0.5 |
| 6aa | 4-OMe,3-OH | 2,4,6-(OMe)$_3$ | 0.010 | 0.003 | 0.004 | 0.003 |
| 6ab | 4-OMe,3-OPO$_3$Na$_2$ | 2,4,6-(OMe)$_3$ | 0.005 | 0.0025 | 0.007 | 0.007 |
| 6ac | 3,4,5-(OMe)$_3$ | 2,4,6-(OMe)$_3$ | >20 | >20 | >20 | >20 |
| 6ad | 2,3,4,-(OMe)$_3$ | 2,4,6-(OMe)$_3$ | 15 | 12.5 | 15 | 15 |
| 6ae | 4-Cl | 2,4,6-(OMe)$_3$ | 10 | 7.5 | 15 | 15 |
| 6af | 4-NO$_2$ | 2,4,6-(OMe)$_3$ | 15 | 15 | 20 | 15 |
| 6ag | 4-CN | 2,4,6-(OMe)$_3$ | 12.5 | 7.5 | 15 | 20 |
| 6ah | 4-COOH | 2,4,6-(OMe)$_3$ | 15 | 10 | 17.5 | 15 |
| 6ai | 4-OH | 2,4,6-(OMe)$_3$ | 15 | 7.5 | 20 | 20 | fluorine atom at the 4-position with a chlorine (6c), a nitro (6d), a methoxy (6a) or an amino (6e) group gradually decreased the activity of the molecules. By changing the position of the methoxy group from the 4 to 2-position (6f) on the styryl aromatic ring, the molecule partially recovered the lost activity. The introduction of a chlorine atom in the 2-position (6g) in 6b retained cytotoxic activity, whereas a methoxy group in the same position (6i) resulted in the loss of activity. Dimethyl substitutions on the styryl aromatic ring with a methoxy group at 4-position on benzyl aromatic ring (6h, 6k and 6l) resulted in the molecules possessing a low level of cytotoxicity. Whereas the results are quite surprising for the molecules that are disubstituted with methoxy groups (6j, 6m, 6n, 6o and 6p) on the styryl aromatic ring, the results obtained in cytotoxicity assays using these compounds (6j, 6m, 6n, 6o and 6p) clearly show that the methoxy group, when present at the 2,6-positions (6m), enhances the activity of the molecule by greater than 40 fold when compared to other disubstituted methoxy sulfones (6j, 6n, 6o and 6p). Because the introduction of two methoxy groups on the styryl aromatic ring enhanced the biological activity, some trimethoxy styryl analogs were synthesized to determine if this further enhances their cytotoxic properties. Analysis of these compounds (6q, 6r, 6s and 6t) in the cell-killing assays showed that 4-methoxybenzyl-2,4,6-trimethoxystyryl sulfone (6s) is 20-fold more active than 6m, where as the other trisubstituted styryl sulfones (6q, 6r and 6t) were totally inactive at the highest concentration (20 μM) tested. These results show that when the 2,4 and 6-positions on the styryl aromatic ring are occupied by methoxy groups, the molecules attain optimum biological activity. To validate whether methyl groups at those positions can replace the methoxy groups and retain the activity, 2,4,6-trimethyl styryl sulfone (6w) was prepared, which was found to be inactive in cell killing assays. To further assess the significance of the methoxy group on the 4-position of styryl ring in 6m, the methoxy group at that site was replaced with a hydroxy (6u) or a fluoro (6v) substituent. Both of these replacements resulted in either a reduced level or total loss of activity. Once the methoxy substituents are fixed at the 2, 4 and 6 positions of the styryl ring, to further enhance the activity of the molecule, the effect of other substituents on the benzyl aromatic ring was then determined. Replacing the methoxy group at the 4-position on the benzylic aromatic ring of 6s by chloro (6ae), nitro (6af), cyano (6ag), carboxy (6ah) and hydroxy (6ai) resulted in molecules that substantially lost activity. These results show that the methoxy group is indispensable at the 4-position of the benzyl aromatic ring of 6s with respect to its biological activity. To analyze the effect of the additional substituents on the benzyl aromatic ring, a number of analogs were synthesized containing 4-methoxy-3-halo, nitro, cyano, carboxy, methoxy (data not shown), hydroxy (6aa), 3,4,5-trimethoxy (6ac), 2,3,4-trimethoxy (6ad) benzyl sulfones. Cytotoxicity analyses of these analogs on four cancer cell lines showed that the compound with the hydroxy substituent at position-3 (6aa) exhibited the best activity in the entire series. This compound, 6aa, is almost 8 to 10 fold more active than 6s in all four cell lines. Further, the introduction of a hydroxy group at the third position not only enhanced the potency of the molecule, but also created a method to generate a water-soluble analog (6ab), which is critical for intravenous administration of the compound. The conversion of the hydroxyl group in 6aa to a disodium phosphate 6ab derivative did not alter the potency of the molecule.

TABLE 2

Tumor cell killing ($IC_{50}$) concentrations (μM) of 6s and 6aa

| Cell Line | Tumor Type | 6s | 6aa |
|---|---|---|---|
| T47D | BREAST (ER+) | 0.025 | 0.006 |
| MCF-7 | BREAST (ER+) | 0.003 | 0.004 |
| DU145 | PROSTATE (AR−) | 0.025 | 0.007 |
| PC-3 | PROSTATE (AR+) | 0.03 | 0.008 |
| OV-CAR-3 | OVARIAN | 0.008 | 0.006 |
| Sk-OV-3 | OVARIAN | ND | 0.006 |
| MIA-PaCa2 | PANCREATIC | 0.008 | 0.004 |
| U87 | GLIOBLASTOMA | 0.04 | 0.007 |
| H157 | NSCLC | 0.03 | 0.007 |
| A549 | NSCLC | 0.02 | 0.01 |
| H187 | SCLC | 0.015 | 0.007 |
| N417 | SCLC | 0.008 | 0.005 |
| AGS | GASTRIC | 0.02 | 0.007 |
| RF1 | GASTRIC | 0.008 | 0.006 |
| RF48 | GASTRIC | 0.01 | 0.005 |
| COLO-205 | COLO-RECTAL | 0.015 | 0.009 |
| DLD-1 | COLO-RECTAL | 0.04 | 0.008 |
| HCT-116 | COLO-RECTAL | ND | 0.009 |
| HCT-15 | COLO-RECTAL | 0.02 | 0.008 |
| SW480 | COLO-RECTAL | ND | 0.007 |
| SK-MEL-28 | MELANOMA | 0.04 | 0.007 |
| CEM | LEUKEMIC | 0.03 | 0.009 |
| K562 | CML | ND | 0.004 |
| MOLT-4 | T-lymphoblastic: ALL | 0.009 | 0.005 |
| Namalwa | Burkitt's Lymphoma (B-cell) | 0.015 | 0.006 |
| Daudi | Burkitt's Lymphoma (B-cell) | 0.008 | 0.007 |
| Raji | Burkitt's Lymphoma (B-cell) | 0.009 | 0.004 |
| MES-SA | SARCOMA | 0.01 | 0.006 |
| *MESSA/DX5 | RESISTANT SARCOMA | 0.01 | 0.005 |
| CEM | LEUKEMIC | 0.03 | 0.01 |
| *CEM/C2 | RESISTANT LEUKEMIC | 0.01 | 0.01 |
| 2008 | Ovarian | ND | 0.005 |
| *2008/17/4 | Resistant Ovarian | ND | 0.004 |

*These cell lines constitute multi-drug resistant cell lines and show up-regulation of MDR and in the case of CEM/C2, additional mutations in the Topo-2 gene (Harker, W. G.; et al. Cancer Res. 1985, 45, 4091-4096; Fujimori, A. et al Cancer Res. 1995, 55, 1339-1346).

Biological Results and Discussion

In Vitro Anti-Tumor Effects of 6s and 6aa Compounds

The activity of two of the most active compounds listed in Table 1 was then tested against 94 different human tumor cell lines and surprisingly, they were found to induce apoptosis of all of these cell lines with very similar $GI_{50}$ values (selected data shown in Table 2). Some of these compounds (such as 6s, 6aa) were also tested by the National Cancer Institute, USA, through its Developmental Therapeutics Program (DTP) against their panel of 60 human cancer cell-lines (Grever, M. R et al. Seminars in Oncology 1992, 19, 622-663). The results showed that these compounds exhibited broad-spectrum activity and inhibited the growth of all of the tested cell lines, including drug-resistant cell-lines, at nanomolar concentrations. Notably, the $GI_{50}$ and $LC_{50}$ values for many of these cell lines were similar, indicating that they induced apoptosis in these cells. Statistical comparison (using the NCI algorithm COMPARE) revealed that these drugs are mitotic blockers of tumor cells.

6s and 6aa Compounds are Highly Active Against Drug Resistant Tumor Cell Lines

Development of resistance to classical chemotherapeutic agents is widely observed in patients who have not responded or have relapsed after first round therapy and is the primary cause of treatment failure. In the initial screening experiments, it was observed that both the Onconova cell panel and the NCI panel included several cell lines which are multi-drug resistant but were highly sensitive to the pro-apoptotic effects of this series of compounds (Harker, W. G. et al. Cancer Res. 1985, 45, 4091-4096; Fujimori, A. et al. Cancer Res. 1995, 55, 1339-1346). To further investigate the activity of these compounds against MDR positive tumor types, the $IC_{50}$ values of 6s and 6aa were determined using two classical MDR positive cell lines. The results shown in FIG. 1a show a 96 h dose response of the uterine sarcoma cell line MES-SA and the multidrug resistant subline MES-SA/DX5 treated with 6aa (Harker, W. G. et al. Cancer Res. 1985, 45, 4091-4096). This cell line has been shown to express high levels of P-glycoprotein and is resistant to a number of drugs including doxorubicin, paclitaxel, vincristine, vinblastine, etoposide, mitoxantrone, dactinomycin, and daunorubucin. The activity of our compounds was then compared to the activity of paclitaxel (MDR sensitive drug). The results show that the parental cell line was very sensitive to Paclitaxel ($IC_{50}$ 4 nM) but the MDR positive subline was greater than 100 fold resistant ($IC_{50}$ 750 nM). When the two cell lines were treated with 6aa, both the parental and the MDR positive cell lines were equally sensitive to the cell killing activity of the compound. It was also investigated as to whether atypical multidrug resistant cell are sensitive to 6aa. For these studies, the parental leukemic cell line CEM and its MDR subline CEM/C2 were employed (Fujimori, A. et al. Cancer Res. 1995, 55, 1339-1346). CEM/C2 was selected and subcloned for resistance to camptothecin and has cross resistance to etoposide, dactinimycin, bleomycin, mitoxantrone, doxorubicin, and daunorubicin. The results show that the campothecin-resistant subline, CEM/C2, was highly sensitive to the styryl benzyl sulfone series of compounds suggesting that these compounds do not share any cross resistance to classical MDR and atypical MDR cell lines (Table 2).

Effect of 6aa and 6ab on Soft Agar Colony Formation

The anti-tumorigenic activity of 6aa and 6ab was then tested in soft agar. For soft agar assays, three different cell lines, BT20, DU145 and MIA-PaCa-2, representing breast, prostate and pancreatic cancers, respectively, were used. In all cases complete inhibition of the growth of tumor cells in a dose dependent manner was observed for the individual compounds (FIG. 1b shows data for MIA-PaCa-2). In these assays, paclitaxel was used as a positive control, which showed a slightly lower potency than that of 6aa and 6ab (FIG. 1b).

Effects of 6s and 6aa on Cell Cycle Progression of Normal and Tumor Cells

Figure 2:
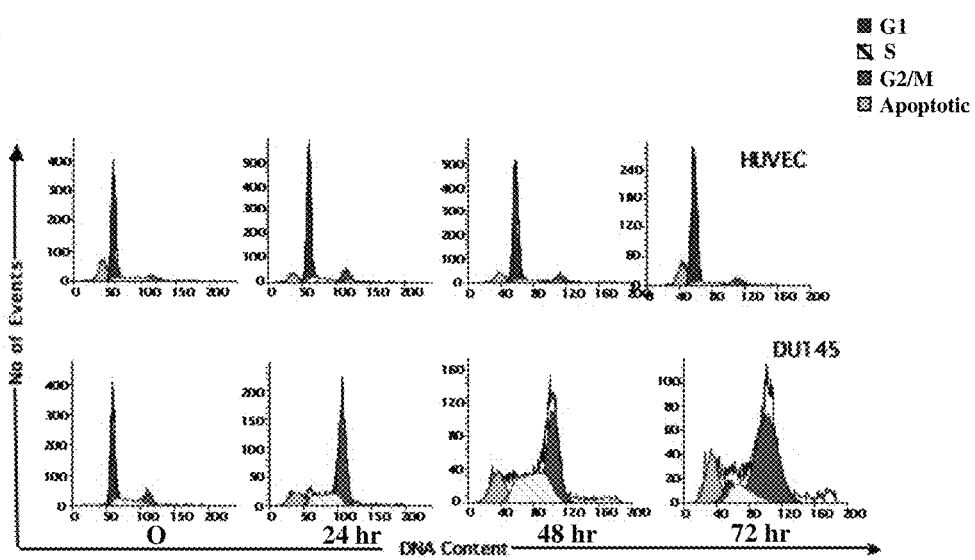
FIG. 2 Preferential tumor cell killing activity of 6aa. A. Cell Cycle analyses. Normal (HUVEC) and tumor cells (DU145) were treated with 20 nM concentration of 6aa and incubated in medium containing 10% fetal bovine serum. At 24 hr intervals, the cells were fixed, stained with propidium iodide and analyzed for their DNA content by flow Cytometry. B. Induction of apoptosis in normal (HUVEC) and tumor cells (DU145) was assessed by western blot analysis of cell lysates treated with 6aa for 24, 48 and 72 h. The Western blots were probed with anti-PARP antibodies to assess the cleavage of the protein.
Figure 2:
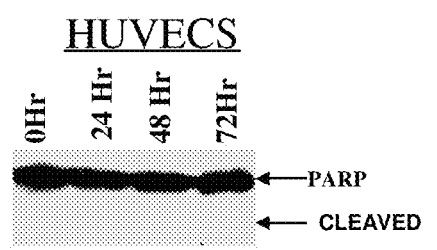
Figure 2:
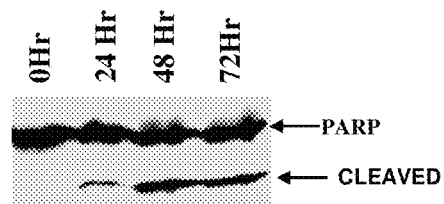

The effect of these compounds on normal and tumor cell cycle progression was then examined using FACS analysis. FIG. 2a show the effect of 6aa on the cell cycle progression of human vascular endothelial cells (HUVEC) and DU145 (prostate cancer) cells. The results of this study show that the addition of the 6aa to HUVEC cells resulted in a block of their cell cycle progression in the $G_1$ phase, causing growth arrest without a loss of viability. On the other hand, tumor cells treated with this compound gradually accumulated in the G2/M phase of the cell cycle and appeared to be unable to exit from this phase, leading to the activation of apoptotic pathways as judged by PARP [Poly(ADP-ribose) polymerase-1] cleavage which is a marker for caspase activation (FIG. 2b) (Soldani, C. et al. Apoptosis 2002, 7, 321-328). No PARP cleavage was observed in HUVEC cells following similar treatment with 6aa compounds (FIG. 2b).

In Vivo Anti-Tumor Effects of 6s and 6aa of Compounds

Figure 3:
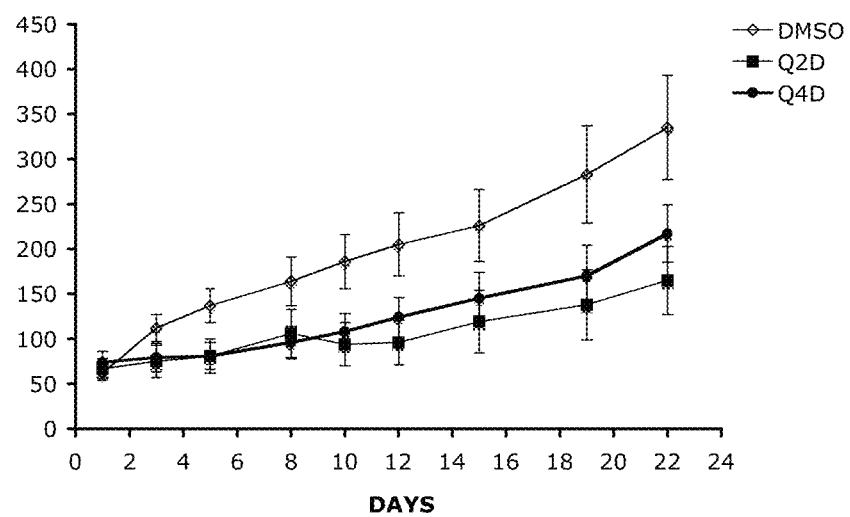
FIG. 3 In vivo Anti-tumor effects of (E)-2,4,6-Trimethoxystyryl-4-Methoxybenzyl sulfone (6s) and (E)-2,4,6-Trimethoxystyryl-$3^1$-O-phosphate disodium-4-methoxybenzyl Sulfone (6ab). Female athymic (NCr-nu/nu) mice were injected subcutaneously with 0.5-1×$10^7$ ER-negative human breast tumor cells (BT-20) in 0.2 mL of PBS and the tumors allowed to grow to a size of 100-150 $mm^3$ in size in about 14 days. The mice were then paired such that the pairs harbored equal sized tumors, which were then used to test the therapeutic effects of 6s and 6ab. A Of the pairs, the animals were treated with either 50 mg/kg 6s following a $Q_4D$ schedule or 25 mg/kg using a $Q_2D$ schedule or vehicle (DMSO) control. The tumor size was then measured on alternate days in two dimensions and the volume determined using either of the following equations: 1: $V=(L\times(S^2))\pi/6$; where L is the longer and S is the shorter of the two measurements. B. 6ab was dissolved in PBS and was administered intravenously (50 mg/kg) through the tail vein on every alternate day. Tumor measurements were done as in materials and methods.
Figure 3:
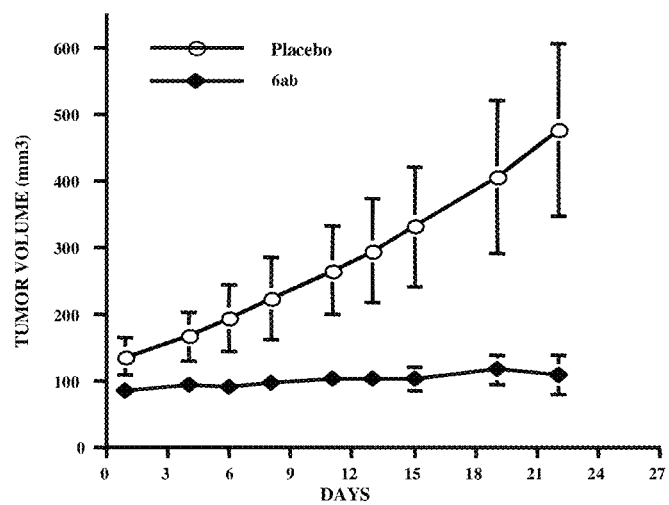

In order to determine in vivo efficacy, the nude mouse model system was utilized. A highly aggressive human estrogen negative breast carcinoma cell line (BT20) was xenografted into athymic nude mice. The animals were treated with either 50 mg/kg of 6s using a Q4D schedule or 25 mg/kg using a Q2D schedule. The animals were treated when the tumors were approximately 70 mm$^3$ in size. FIG. 3a shows that intraperitonial (IP) injections of 6s using either of the two schedules were able to inhibit the growth of the tumors. The vehicle control treated tumors, on average, increased in volume over the 22 day period by 5 fold (62 mm$^3$-335.5 mm$^3$), while the Q2D 6s treated tumors increased in volume by only 2.5 fold (67.5 mm$^3$-165 mm$^3$). The Q4D 6s treated tumors also had significant but slightly less tumor growth inhibition, whereby these tumors increased in average volume by only 2.9 fold (74 mm$^3$-217 mm$^3$). 6s was well tolerated at these doses as determined by body weights and physical observations. These studies show that 6s is efficacious against human tumor xenografts while showing no signs of toxicity at the schedules tested under this study.

Because 6s is poorly water-soluble, 6ab was synthesized which was highly water-soluble and allowed intravenous administration (Pettit, G. R. et al Anti-Cancer drug. Des. 2000, 15, 203-216; Pettit, G. R. et al Anti-Cancer Drug. Des. 2001, 16, 185-193; Pettit, G. R. et al. J. Med. Chem. 2002, 45, 2534-2542). To test the effects of 6ab in vivo, two groups of mice were used. One group received the vehicle alone, while the second group received the compound by intravenous (IV) injection into the tail vein (3b). The tumor size was then measured on alternate days and the total length of the experiment was 21 days. The results presented in FIG. 3b show that 6ab readily inhibited tumor growth in this xenograft model system. Of the 8 mice included in each group, 100% of the control mice (placebo administered) showed a doubling or tripling of the total tumor volume. On the other hand, the majority of the mice administered with 6s or the phosphate salt of 6aa showed growth arrest or a gradual reduction in their tumor volume, suggesting that these compounds, with proper formulation can be valuable anti-cancer therapeutics.

In Vivo Toxicity Studies in Mice

Figure 4:
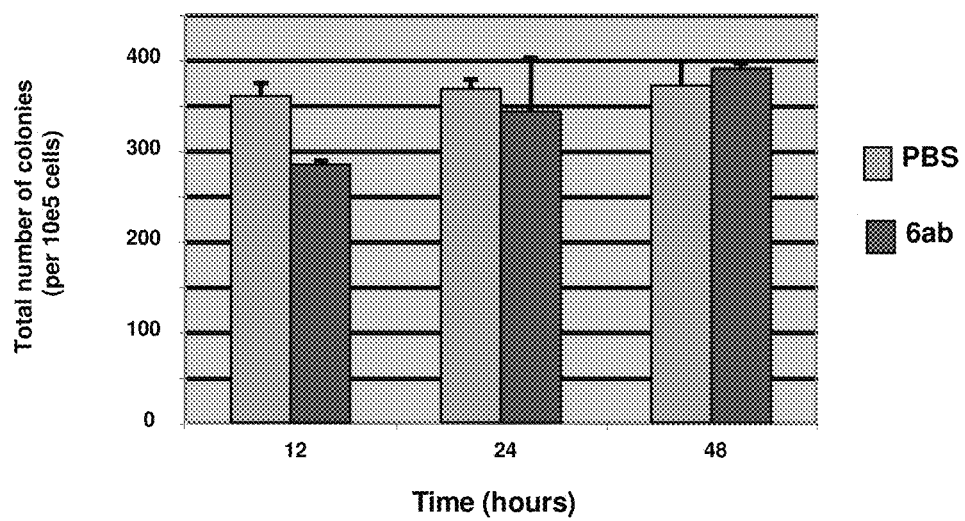
FIG. 4 Bone marrow toxicity profile of 6ab. To assess the toxicity of 6ab, the phosphate salt of the drug was injected into mice (100 mg/Kg) and bone marrow harvested from femur and tibia after 12, 24 and 36 h following the injection of the drug. The bone marrow cells were cultured in methylcellulose medium supplemented with a mixture of stem cell factor, GM-CSF, IL-3 and erythropoietin for one week and colony forming units were determined.

To assess the in vivo toxicity profile, 100 mg/kg of 6aa was intravenously administered into mice and its effect on the in vitro hematopoietic colony formation of bone marrow cells was determined at 12, 24 and 48 h intervals following the injection of the drug. These studies (FIG. 4) show that there was no reduction in total, myeloid or lymphoid colony formation. Single dose and repeat-dose (28 daily injections) toxicology studies and detailed biochemical and cellular analysis of one of the water-soluble analogs (6ab) revealed that unlike most other cytotoxic agents, this drug did not cause hematotoxicity (no myleosuppression), liver damage or detectable neurotoxicity in these animals. High, dose dependent, drug levels were sustained in circulation suggesting that therapeutic levels could be achieved without overt toxicity.

Acute and Repeat Toxicity Studies in Rats

Single dose and repeat-dose (28 daily injections) toxicology studies were carried out with one water-soluble form of this series (6ab) to assess the safety of intravenously administered drug in rats. Detailed biochemical and cellular analysis revealed that this drug did not cause hematotoxicity (no myleosuppression), liver damage or any detectable neurotoxicity in these animal studies. High dose dependent drug levels were sustained in circulation suggesting that therapeutic levels could be achieved without overt toxicity.

Conclusion

In this communication, the synthesis of a group of styryl benzyl sulfones was described which induce apoptotic death of a wide variety of human tumor cell lines at sub nanomolar concentrations while exhibiting relatively low toxicity to normal human cells. The studies show that the cytoxic activity of the styryl benzyl sulfones is completely dependent on the nature and position of the substituents on the two aromatic rings. In a majority of the compounds described here, a methoxy group constant at the 4$^{th}$ position was retained on the aromatic ring of the benzyl moiety. These structure function studies show that when the 2, 4 and 6-positions on the styryl aromatic ring are occupied by the methoxy groups, the molecules attain optimum biological activity (6s). This activity could be further enhanced by the introduction of a hydroxyl group at the third position of the benzylic ring (6aa and 6ab). Biological evaluation of the activity of these compounds show that these compounds are highly active against a wide variety of human tumor cell lines including those that are resistant to the activity of many of the currently used chemotherapeutic agents.

The low toxicity profile, both in vitro and in vivo and their potent tumor inhibitory activity as seen in soft agar and nude mouse xenograft assays point to the potential value of these compounds as safe therapies for cancer, lacking many of the side effects normally associated with current chemotherapeutic agents. Recent studies with 6s, 6aa and 6ab show that these compounds altered the growth and cell cycle status of mantle cell lymphoma cell lines and potently inhibited the expression of several important proteins, including cyclin-dependent kinase 4, p53, mouse double minute 2 (MDM2), and cyclin D (Park, I. W. et al Oncogene 2007, 26, 5635-5642). Since 6s, 6aa and 6ab are highly effective in various combinations with conventional chemotherapy; the lack of overt hematotoxicity of these compounds may be beneficial for testing novel combinations for advanced cancers, including tumors resistant to conventional chemotherapy. In addition, their safety profile seen with normal hematopoietic cells suggest that these compounds have a potential use in in vitro purging of tumor cells from patient bone marrow for use in autologous bone marrow transplantation. Clinical and preclinical studies currently underway will reveal the best way to utilize these compounds in cancer therapy.

REFERENCES (1) Malumbres, M.; Barbacid, M. To cycle or not to cycle: A critical decision in cancer. *Nat. Rev. Cancer* 2001, 1, 222-231.
(2) Sherr, C. J.; McCormick, F. The Rb and p53 pathways in cancer. *Cancer Cell* 2002, 2, 103-112.
(3) Grana, X.; Reddy, E. P. Cell cycle control in mammalian cells: role of cyclins, cyclin dependent kinases (CDKs), growth suppressor genes and cyclin dependent kinase inhibitors (CKIs). *Oncogene* 1995, 11, 211-219.
(4) Blagosklonny, M. V.; Pardee, A. B. The Restriction Point of the Cell Cycle. *Cell Cycle* 2002, 1, 103-105.
(5) Hunter, T. Oncoprotein Networks. *Cell* 1997, 88, 333-346.
(6) Morgan, D. O. Cyclin-dependent kinases: Engines, Clocks, and Microprocessors. *Annu Rev Cell Dev Biol.* 1997, 13, 261-291.

(7) Donjerkovic, D.; Scott, D. W. Regulation of the G1 phase of the mammalian cell cycle. *Cell Res.* 2000, 10, 1-16.

(8) O'Connor, P. M. Mammalian G1 and G2 phase checkpoints. *Cancer Surv.* 1997, 29, 151-182.

(9) Millard, S. S.; Kof, A. Cyclin-dependent kinase inhibitors in restriction point control, genomic stability and tumorigenesis. *J. Cell Biochem.* 1998, suppl. 30-31, 37-42.

(10) Mc Donald, E. R.; El-Diery, W. S. Check point genes in cancer. *Ann. Med.* 2001, 33, 113-122.

(11) Ewen, M. E. Relationship between Ras pathways and cell cycle control. *Prog. Cell Cycle Res.* 2000, 4, 1-17.

(12) Wang, T.; Wang, H.; Soong, Y. Paclitaxel-induced cell death. *Cancer* 2000, 88, 2619-2628.

(13) (a) Reddy, M. V. R.; Reddy, S. Synthesis of α,β-Unsaturated Sulfones. *Acta Chim. Hung.* 1984, 115, 269-271. (b) Reddy, D. B.; Reddy, N. S.; Reddy, S.; Reddy, M. V. R.; Balasubramanyam, S. Preparation of styryl benzyl sulfones and 1,2-bis-(styrylsulfonyl-methyl)-4,5-dimethylbenzenes. *Org. Prep. Proc. Int.* 1988, 20. 205-212.

(14) Reddy, A. K.; Lohray, B. B.; Bhushan, V.; Reddy, A. S.; Mamidi, N. V. S. R.; Reddy, P. P.; Saibaba, V.; Reddy, N. J.; Suryaprakash, A.; Misra, P.; Vikramadithan, R. K; Rajagopalan, R. Novel Antidiabetic and Hypolipidemic Agents.5. Hydroxyl versus Benzyloxy Containing Chroman Derivatives. *J. Med. Chem.* 1999, 42, 3265-3278.

(15) (a) Reddy, M. V. R.; Reddy, S.; Reddy, D. B. Facile method for the synthesis of 2-(arylsulfonyl)-1-phenyl-3-aryl-2-propen-1-ones. *Sulfur Lett.* 1987, 7, 43-48. (b) Russell Llyod, B.; Anthony, D.; Chantal Renee, F.; Richard Francis, L. Novel Knoevenagel condensation of a β-keto sulfone and a β-carboalkoxy sulfone. *Sulfur Lett.* 1999, 23, 11-31. (c) Reddy, M. M.; Venkat, R. P.; Reddy, E. P.; Reddy, M. V. R. Sequential Reduction and Dehydration of Phenacyl-(E)-Styryl Sulfones to Unsymmetrical (E,E)-Bis (styryl) Sulfones. *Synthesis* 2005, 3639-3643. (d) Touati, A.; Cazaux, L. Synthesis of sulfonamides, sulfonates and thiosulfonates which are inhibitors of coniferyl alcohol dehydrogenase. *J. Soc. Alger. Chim.* 1996, 6, 39-52.

(16) (a) Kendall, P. M.; Johnson, J. V.; Cook, C. E. Synthetic route to an aromatic analog of strigol. *J. Org. Chem.* 1979. 44, 1421-1424. (b) Ronald, R. C.; Lansinger, T. S.; Lillie, T. S.; Wheeler, C. J. Total synthesis of frustulosin and aurocitrin. *J. Org. Chem.* 1982, 47, 2541-2549. (c) Corey, E. J.; Venkateswarulu, A. Protection of hydroxyl groups as tert-butyldimethylsilyl derivatives. *J. Am. Chem. Soc.* 1972, 94, 6190-6191.

(17) Wolfrom, M. L.; Koos, E. W.; Bhat, H. B. Osage orange pigment. XV111. Synthesis of osajaxanthone. *J. Org. Chem.* 1967, 32, 1058-1060.

(18) (a) Pettit, G. R.; Lippert, J. W. Antineoplastic Agents. 429. Synthesis of the combretastatin A-1 and combretastatin B-1 prodrugs. *Anti-Cancer drug. Des.* 2000, 15, 203-216. (b) Pettit, G. R.; Moser, B. R.; Boyd1, M. R.; Schmidt, J. M.; Pettit, R. K.; Chapuis, J-C. Antineoplastic Agents. 460. Synthesis of combretastatin A-2 prodrugs. *Anti-Cancer drug. Des.* 2001, 16, 185-193. (c) Pettit, G. R.; Grealish, M. P.; Jung, K.; Hamel, E.; Pettit, R. K.; Chapuis, J-C.; Schmidt, J. M. Antineoplastic Agents. 465. Structural Modification of Resveratrol: Sodium Resverastatin Phosphate1. *J. Med. Chem.* 2002, 45, 2534-2542.

(19) Harker, W. G.; Sikic, B. I. Multidrug (pleiotropic) resistance in doxorubicin selected variants of the human sarcoma cell line MES-SA. *Cancer Res.* 1985, 45, 4091-4096.

(20) Fujimori, A.; Arker, W. G.; Kohlhagen, G.; Hoki, Y.; Pommier, Y. Mutation at the catalytic site of topoisomerase 1 in CEM/C2, a human leukemia cell line resistant to camptothecin. *Cancer Res.* 1995, 55, 1339-1346.

(21) Grever, M. R.; Schepartz, S. A.; Chabner, B. A. The National Cancer Institute:Cancer Drug Discovery and Development Program. *Seminars in Oncology* 1992, 19, 622-663.

(22) Soldani, C.; Scovassi, A. I. Poly (ADP-ribose) polymerase-1 clevage during apoptosis: an update. *Apoptosis* 2002, 7, 321-328.

(23) Park, I. W.; Reddy, M. V. R.; Reddy, E. P.; Groopman, J. E. Evaluation of novel cell cycle inhibitors in mantle cell lymphoma. *Oncogene* 2007, 26, 5635-5642.

(24) Cosenza, S. C.; Baker, S. J.; Reddy, E. P. *Methods for oncogenic detection. In Cell Growth, Differentiation and Senescence*, Studzinski, G. P., Ed.; Oxford University Press: 1999, 161-176.

Example 2

Preparation of ON 013105

STAGE-1: Protection of Phenolic-OH group (a) 500 g of Isovanilin and 1000 g of p-Toluenesulfonyl chloride are dissolved in 1250 ml of Pyridine in a 20 L glass reactor kept in a water bath. The reaction mixture is stirred well for about 15 minutes. The clear solution gradually becomes turbid and becomes slurry. Stirring is continued for a period of 2 hrs. The water bath is maintained at 70-80 degrees throughout the reaction.

(b) After two hours, the reaction mixture is allowed to attain room temp and cold water is added to the reactor to get a white crystalline solid. The solid is filtered and washed successively with 500 ml 1:1 HCl, 500 ml of 5% NaOH solution and water till the filtrate is free from Pyridine. The precipitate is dried and weighed.

(c) The weight of the compound is 985 grams, i.e. 98%. The melting point range 148-151° C.

(d) TLC shows the absence of isovanillin and the presence of a spot moving faster than isovanillin spot.

Remarks: 1. Yield depends upon the purity of p-Toluene sulfonyl chloride.

2. Color of the compound varies from off-white to white.

3. Washing and treatment are the key procedures to decide the quality of the compound.

4. Reaction completes within 15 min. But to get the pure compound stirring and heating should be continued up to 1.5 to 2 hrs.

All the chemicals used in this process are commercial samples.

| Ratio of Reactants: | IV:PTSC:Pyr. 1:2:2.5 |
|---|---|

Abbreviations:
IV: Isovanilin,
PTSC: P-Toluenesulfonyl Chloride,
Pyr: Pyridine

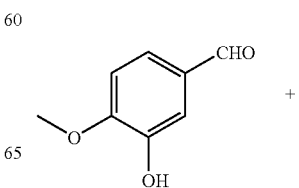

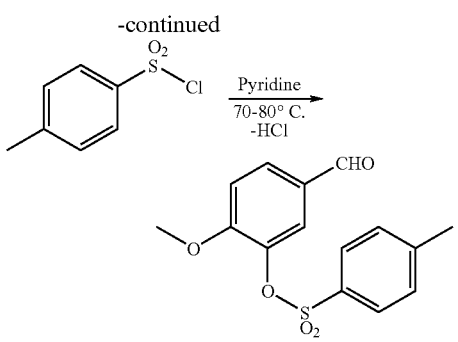

STAGE-2: Stage 1 compound→Mol wt: 306
MP range: 148-151° C.

The Stage-1 compound 985 g (3.2189 moles) is taken in 2.5 L of methanol in a 20 L glass reactor maintained in a cold water bath (20° C.). The reducing agent sodium borohydride 60 g (0.58 moles) in methanol is added slowly over a period of 20 to 30 minutes. Reaction is over by the time the addition is completed. During the addition of sodium borohydride, the solution in the reaction becomes clear without any solid. The stirring is continued. During the stirring process white crystalline solid separates in methanol. After two hours, water is added to the reaction mixture to ensure complete precipitation in the reactor. After 2 hours the precipitate formed is filtered off and washed thoroughly with water. A white crystalline solid that weighs 965 g (after drying) 97% is obtained. The melting range of the compound is 88-90° C. Mol wt: 308

Remarks: 1. Sodium borohydride should be quickly made as fine powder (if crystalline) and to dissolve in cool methanol so that the vigorous and exothermic nature of the reaction can be controlled.
2. During addition, small portions of $NaBH_4$ methanol solution is preferable, but quick enough.
3. Addition must be continuous and the heat developed in the addition flask can be avoided by taking chilled methanol.
4. Proper outlet (condenser) is required for the reactor to avoid the development of the pressure inside.
5. Temperature should be controlled throughout the reaction between 15 and 20 degrees Centigrade The solvent and the $NaBH_4$ are commercial samples.
Key words: Sodiumborohydride (SBH) MR: Melting range
RM: Reaction mixture

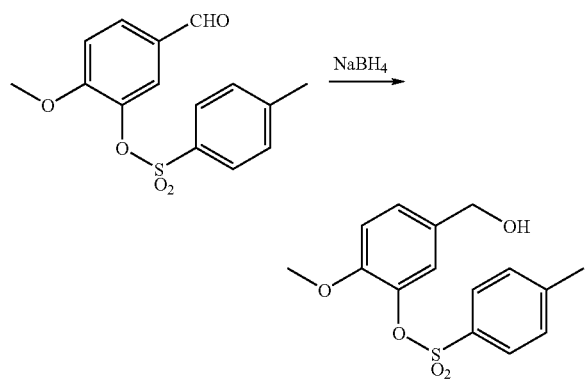

STAGE-3: Stage 2 compound→Mol wt: 308
MP range: 148-151 degrees C.

Stage-2 compound 965 g (3.13 moles) is taken in 2 L of benzene in a 10 L reactor which is maintained at 15 and 20° C. in a water bath. Thionyl Chloride 227 ml (3.13 moles) in 500 ml of benzene is added dropwise to the reaction mixture under vigorous stirring. The product starts separating from the clear reaction mixture within 30 min. After completion of the addition the reaction mixture is allowed under stirring for about 2 hrs. The reactor is connected to vacuum through a trap containing formic acid. Under mild heating and high vacuum thionyl chloride and some portion of benzene is collected in the trap. The process is continued till all the unreacted thionyl chloride is distilled off. The slurry left over is filtered and washed with hexane (hexane is added to the reaction mixture in the reactor and allowed under stirring 15 minutes). The filtrate is concentrated under vacuum and the resulting precipitate is washed with hexane. Both the precipitates are combined and dried under vacuum. The dried compound weighed 925 g (approx. 90%). The melting range is 102-105° C. Completion of the reaction is monitored by T.L.C.

Remarks: 1. Thionyl chloride should be handled in an effective Fume hood. It should be handled with gloves, goggles, and nose mask.
2. Benzene volume can be minimized and the addition can be made fast.
3. Stirring with hexane will give pure product.

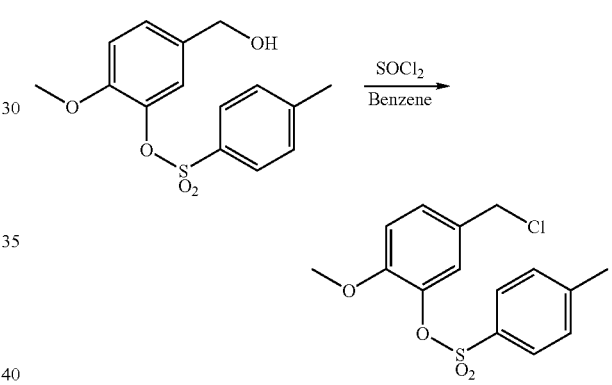

STAGE-4: Stage 3 compound→Mol wt: 326
MP range: 102-105° C.

Sodium hydroxide 226 g (2.83×2 moles) is added to 4 lit of Methanol taken in a 20 lit glass reactor. To the clear solution of sodium methoxide, 197 ml (2.83 moles) of 100% Thioglycollic acid is added portion wise so that the methanollic solution reflux gently. Then the Stage-3 compound 925 g (2.38 moles) is added to the methanolic solution in portions and the reaction mixture is subjected to refluxion for about 5 hrs. The reaction is monitored by TLC. The reaction mixture is cooled to room temperature under stirring. The cold water is added to the reactor to destroy methanol. This solution is neutralized with cold dilute hydrochloric acid. A white crystalline solid separated is filtered and washed with water till no smell of thioglycollic acid is observed. The dry thioacetic acid weighed 993 g (93%). The melting range is 116-120° C.

Remarks: 1. $NaOH/CH_3OH$ and $NaSCH_2COOH$. This reaction is exothermic. Hence, care should be taken to arrest the evaporation of $CH_3OH$.
2. Plenty of cold water should be used to eliminate impurities which interfere at this stage.
3. During neutralization the reactor should not develop temperature.
4. Washing with water under vacuum is a must to remove the unreacted thioglycollic acetic acid.

5. Work up should end without any smell of thioacetic acid.

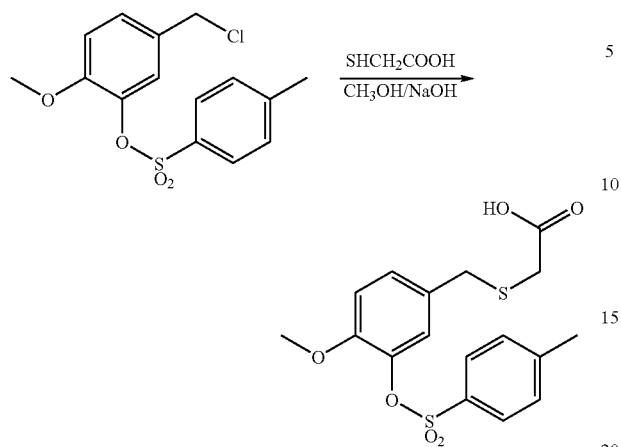

STAGE-5: Stage 4 compound→Mol wt: 381

MR: 116-120 degrees C.

Stage 4 compound 993 g (2.6062 moles) is taken in 4 L of acetic acid contained in a 20 L glass reactor. Hydrogen peroxide (30%) 3 L is added to the contents of the reactor. The reactor is warmed just enough to dissolve Stage-4 compound in acetic acid. The reactor is allowed at RT under stirring for 24 hrs. The precipitate formed in the reactor is separated, filtered, washed with water, and dried. The filtrate is diluted with cold water and the precipitate formed is filtered, washed with cold water, and dried. The two dried solids are added and weighed. The weight of the solid is 937 g (87%). This crude is further washed with benzene to give the pure product, which weighed 861 g (80%). MP range 142-146° C.

Remarks: 1. Acetic acid and Hydrogen peroxide are in the ratio of 5:3 to the compound.

2. Reaction on heating is vigorous. Hence, dissolution of stage 4 compound should be done carefully under mild warming.

3. On completion of reaction the white crystalline solid separates under stirring. For better quality, the precipitate and the filtrate should be treated with cold water separately.

4. All the impurities carried over through all stages can be totally removed by washing the precipitate with benzene. Hence the yield of the pure compound varies from 80% to 90%.

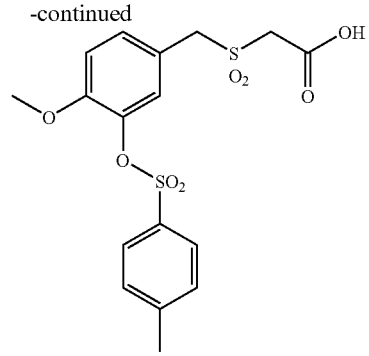

STAGE-6: Stage 5 compound→Mol wt: 414

MP range: 142-146 degrees C.

In a twenty liter glass reactor which is maintained in an oil bath is taken 8 lit of benzene. To the contents of the flask 409 g (2.0797 moles) of 2,4,6-trimethoxy benzaldehyde is added and the reaction mixture is stirred to dissolve the aldehyde. To the aldehyde solution, 75 g (0.6 moles) of benzoic acid and 60 ml of piperidine are added. Later Stage-5 compound 861 g is added to the reaction mixture and the solution is refluxed. The Dean-Stark apparatus is fixed to the reactor to remove the water, which forms during the reaction from time to time. Reaction is completed in 5 hrs. The reaction mixture is brought to the room temperature under stirring. Crystalline substance starts forming and the reaction mixture is allowed to stand overnight to have good quality of the product. The precipitate is filtered off and washed with benzene. The washings are concentrated and the resulting precipitate is further washed with benzene. The first and second crops were collected.

The melting range is 159-166 degrees C.

Remarks: 1. Stage 5 compound is soluble completely only after the addition of piperidine and at refluxing temperature.

2. Temperature more than 105° C. may cause decarboxylation prior to dehydration resulting in the formation of methyl benzyl sulfone more in percentage. This will decrease the percentage of benzyl stylyl sulfone.

3. Second crop should be washed with either ethylacetate or Methanol to remove methylated compound.

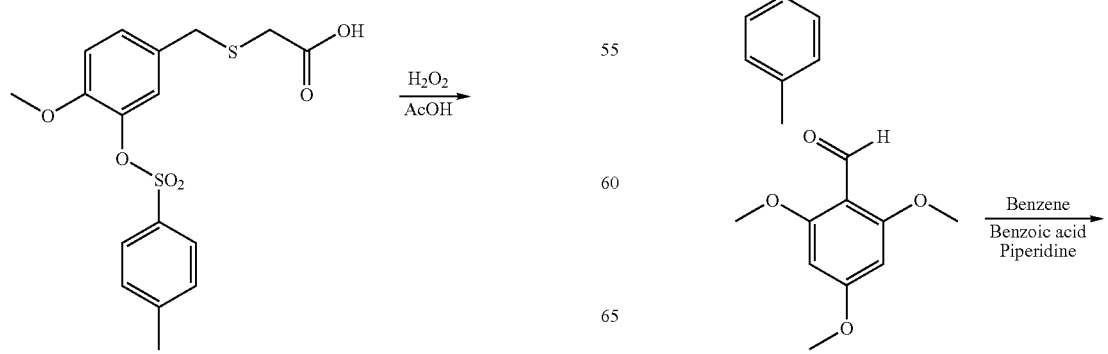

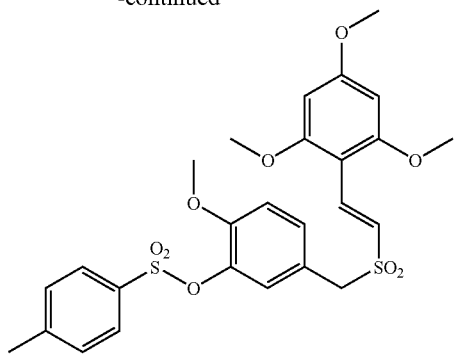

STAGE-7: Stage 6 compound→Mol wt: 548

MP range: 159-166° C.

Stage-6 compound 740 g (1.3503 moles) is taken in 7.4 lit of 20% sodium hydroxide solution. To this 7.4 lit of methanol is added. The reactor is heated to reflux the solution under stirring. The compound is not completely soluble. As time goes on the clear solution is obtained. TLC shows the completion of reaction when the solution becomes very clear. The time taken for the completion of the reaction is 2 hrs. But to ensure complete conversion, stirring is continued further for a period of one to one and one half hours. The reaction mixture is cooled to room temperature and the solution is neutralized with cool dilute hydrochloric acid solution. The white (or light green) precipitate starts separating. The precipitate is filtered, washed with water, and dried. The crude dry precipitate weighed 505 g (95%) which, has melting point range 124-127° C.

Remarks: 1. During work up ice and cold water should be used plenty to get neat crystalline compound. Otherwise a paste like compound which sticks to the walls of the container will be obtained.

2. After completion of the reaction the reaction mixture should be allowed to settle unreacted sulfone at the bottom. The solution should be either decanted or allowed to pass through a filter paper. The precipitate can be used along with the other batch of sulfone.

STAGE 8

Stage 7 compound→Mol wt: 394

MP range: 124-127° C.

Stage-7 compound 500 g (1.2690 moles) is taken for a 20 L glass reactor. Acetonitrile 5 L is taken into the reactor. Stage-7 compound is not soluble completely in acetomitrile. Carbon tetrachloride (AR) 790 ml (6 equivalents), Triethylamine (AR) 921 ml (6 equivalents) and dimethylamino pyridine (0.1 equivalent) are added successively to the reactor under stirring. Stirring is continued for about 10 minutes. Dibenzylphosphite, 421 ml (1.5 equivalent) is added to the contents of the reactor at room temperature for a period of 30 minutes. During the addition, the reaction mixture becomes clear solution, and proceeds exothermically. By TLC analysis, the reaction is completed in an hour after the addition. The reaction is allowed two more hours under stirring and allowed overnight.

To the contents of the reactor, 2.5 L of 0.5M $KH_2PO_4$ solution is added and stirred 5 minutes. The reaction mixture is allowed to settle. The organic layer is separated and the aqueous layer is extracted with methylene chloride twice. The organic layers are combined and concentrated under vacuum. The viscous dense organic layer is taken in the separating funnel. The heavy thick layer from the bottom is separated from the upper layer. The upper layer is again treated with DCM and the DCM layer is collected. The other layer mainly contains impurities. Hence discarded. The thick organic layer and the DCM layer are combined and concentrated once again. The yield is 829 gr assumed as 100%.

Remarks: 1. Addition of DBP within 30 minutes generates heat in the reactor. This heat energy is sufficient to move the reaction towards right. Hence quick addition is needed.

2. All the impurities which are noticed at the base in TLC are separated in the treatment of upper layer with DCM.

3. The viscous liquid can be used as it is for the next step. The yield can be assumed as 100%.

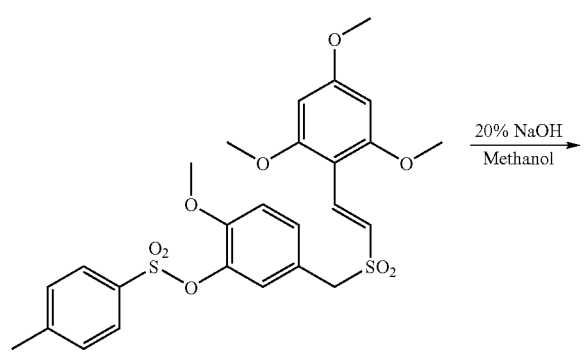

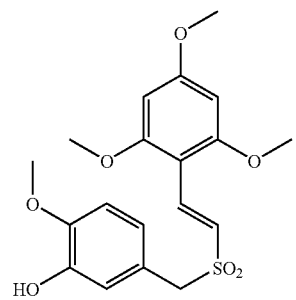

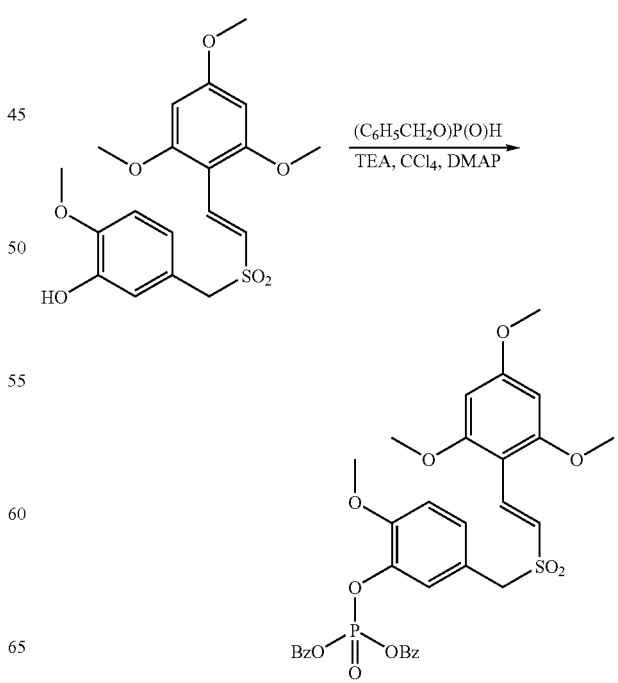

STAGE 9 Stage 8 compound→Mol wt: 626

MP range: dense liquid

Assuming 100% reaction in Stage-8, the syrupy compound is dissolved in 4 L of acetonitrile. To this solution 399 grams (2.1 equivalent) of sodium iodide is added under stirring. The reactor is maintained in Nitrogen atmosphere and 344 ml of bromo/chloro trimethylsilane (2.1 equivalent) is added drop wise in 45 minutes. The reaction mixture is stirred at room temperature. The reaction mixture develops color (pink/red) during the addition of bromo/chlorotrimethylsilane. Reaction completes in an hour after the addition of bromo/chlorotrimethylsilane. The reaction is further continued for about 2 hours.

To the reaction mixture, 4 L of 1% hypo solution is added and the stirring is maintained for 10 minutes. The organic layer is separated from the aqueous layer. The aqueous layer is washed twice with DCM. The combined organic layers are concentrated under vacuum. The thick syrup that is left after concentration is washed thoroughly with hexane and ethyl acetate successively. All the impurities are removed in washings. The compound is now left as pure and is subjected to vacuum drying. Highly gummy semisolid is obtained. The isolated and pure compound decomposes above 200° C. Assuming 100% reaction in Stage 9, the compound is subjected to Stage 10.

Remarks: 1. Bromotrimethylsilane/chlorotrimethylsilane is highly hygroscopic and irritant. It should be drawn and injected into the reactor with much caution.

2. Important—During washing with hexane and ethyl acetate, the fume hood should be closed for effective withdrawal of lachrymatory vapors.

3. If stirring is not continuous, the reaction becomes stalemate.

STAGE 10 Stage compound→Mol wt: 474

MP range: >200° C.

Assuming 100% reaction in Stage-9, 601 gr. of the compound is dissolved in 7.5 L of 1,2-dimethoxyethane (Ethyleneglycol dimethylether). Sodium hydroxide solution 1262 ml (8% solution) is added in portions with vigorous stirring. The clear solution turns turbid and finally the precipitate comes out of the reaction mixture. At this stage, the pH is maintained between 7.0-7.5. The contents are stirred for four more hours. The reaction mixture is allowed to settle the precipitate. The precipitate is filtered and washed with acetone and dried under vacuum. The dried compound weighs 510 grams (77%).

REMARKS: 1. The compound of Stage 9 is soluble in ether only with vigorous shaking.

2. Addition of NaOH should be slow. For every addition, the RM should be shaken thoroughly and each time PH should be checked 3. Before addition, the reaction mixture is acidic and is slowly brought to 7.5 with NaOH solution.

4. Drying should be carried out under vacuum with temperature not more than 30° C.

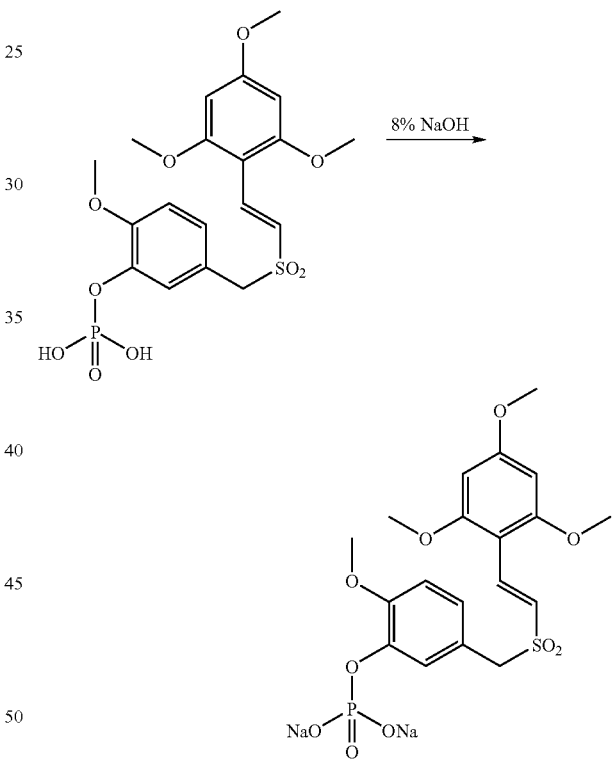

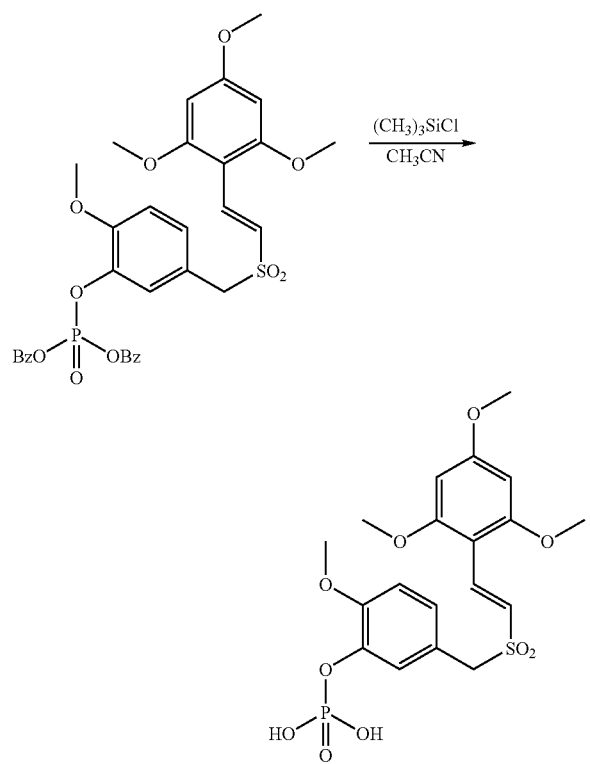

Example 3

Phosphorylation of Compound 013100 Using $POCl_3$

The following Example is directed to the preparation of Compound 013105 by phosphorylation of Compound 013100 using $POCl_3$.

Scheme 7 below depicts the method for the synthesis of (E)-2,4,6-(trimethoxystyryl)-3-O-phosphate disodium-4-methoxybenzyl sulfone (Compound 013105).

50 grams of compound 20 is dissolved in 500 ml of THF. To the solution 125 ml of Triethylamine is added. The solution is filtered to get the clear solution. This is taken into a pressure equalizing dropping funnel.

Into a 2 lit three necked flask 50 ml of Phosphorous oxychloride in 150 ml of THF is taken. The reactor is fitted with a mechanical stirrer and a reflux condenser and kept in an ice bath to attain 0 C degree. To this cooled solution, the solution in the pressure equalizing funnel (Compound 013100+Et3N+ THF) is added drop-wise for a period of 90 minutes (TLC shows the completion of reaction).

The ice bath is allowed to attain room temperature and the stirring is continued for 2½ hrs. At this stage the reaction mixture develops light yellow color with the formation of water soluble precipitate.

The reaction mixture is again taken into the pressure equalizing dropping funnel. Into the 2 lit flask 500 ml of ice cubes are taken. The flask is cooled in an ice bath. The reaction mixture is added to the ice cubes over a period of 45 minutes. After completion of the addition, stirring is continued for 5 to 7 hrs. To the contents of the flask 200 ml of 50% potassium hydroxide solution (85%) is added slowly. During the addition the flask is maintained in an ice bath. After the addition of KOH solution stirring is continued for a period of 40 minutes.

The reaction mixture is allowed to settle for the separation of organic layer. The organic layer is separated and tested for the presence of Compound 013100 and the other impurity that appeared above the Compound 013100 in TLC The aqueous layer is washed twice with THF (2×400 ml portions) and each time the organic layer is tested for the impurities and discarded. At this stage the aqueous layer is totally free from the impurities. Finally the aqueous layer is washed with 500 ml of ethyl acetate.

The aqueous layer is taken in a two liter RB which is maintained in an ice bath. To this dilute HCl solution (1:1, 135 ml) is added drop-wise under moderate stirring. During the addition the phosphoric acid of Compound 20 starts separation as light yellow gummy solid. Stirring is continued for 3½ hrs to get light yellow granulated solid. The solid compound is filtered dried and weighed (50 grams)

The solid compound is dissolved in 400 ml of methanol and the solution is filtered to remove the insoluble and suspended impurities. The clear solution is taken in a conical flask equipped with a magnetic stirrer. The assembly is kept in a water bath. To the solution, 32 ml of 25% sodium hydroxide solution is added drop-wise under stirring. During the addition a white phosphate salt formation is observed. After completion of the addition of NaOH solution, the PH of the solution is found to be 8. Stirring is continued for 6 hrs for the completion of phosphate salt formation.

The phosphate salt is filtered and the conical flask is washed with 100 ml of acetone to transfer on to the filter funnel. The precipitate is washed with 2×100 ml portions of acetone. Finally the salt is dried under vacuum. The dried salt weighed 50 grams. The Compound 013105 is found to be matching with the standard sample.

Scheme 7: Method for the Synthesis of (E)-2,4,6-(Trimethoxystyryl)-3-O-Phosphate Disodium-4-Methoxybenzyl Sulfone

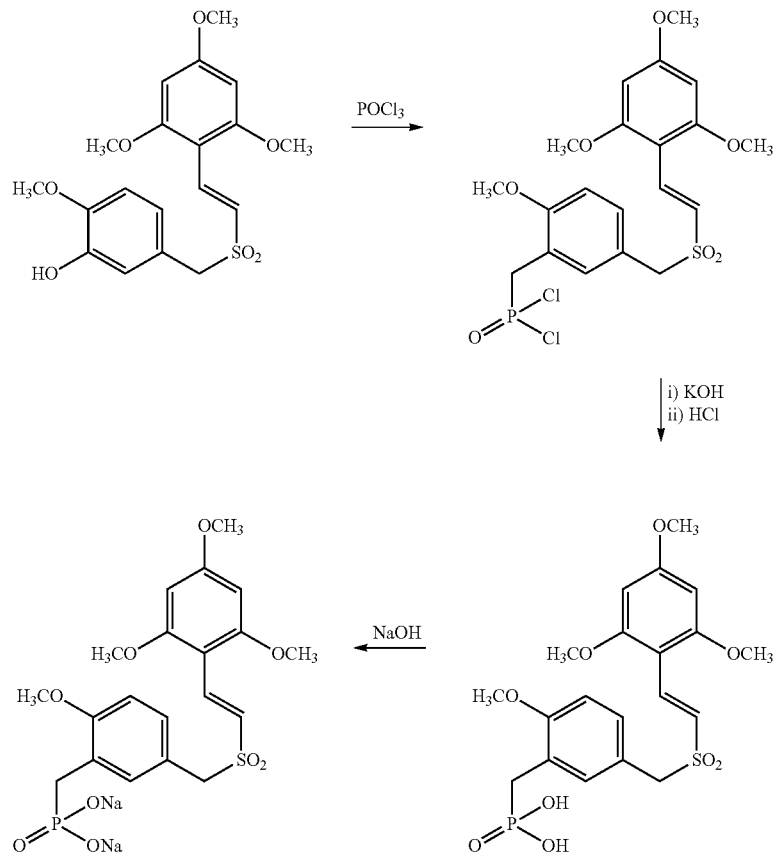

All references cited herein are incorporated by reference. The present invention may be embodied in other specific forms without departing from the sprit or essential attributes thereof and, accordingly, reference should be made to the appended claims, rather than to the foregoing specification, as indication the scope of the invention.

What is claimed is:

1. A process for preparing a compound of the Formula 29

Compound 29

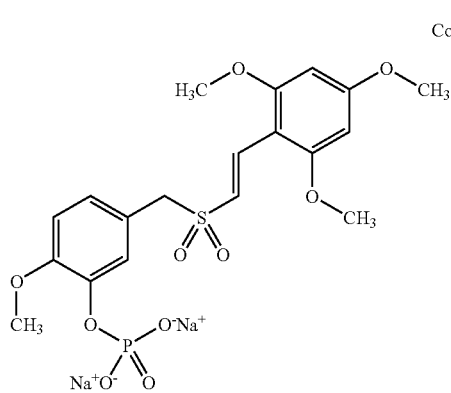

the process comprising (i) condensing sulfonylacetic acid compound 25 with 2,4,6-trimethoxy benzaldehyde compound 19

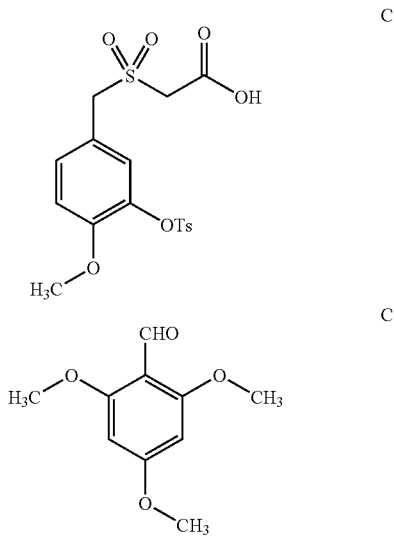

in the presence of a base to produce unsaturated sulfone compound 26;

Compound 26

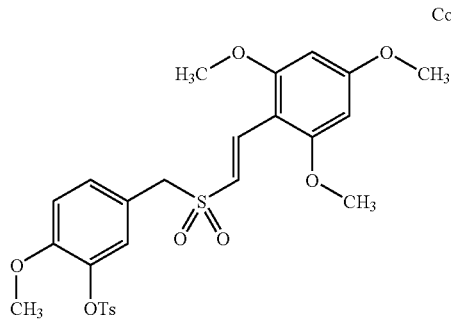

(ii) removing the tosyl group by treating unsaturated sulfone compound 26 with sodium hydroxide that yields styryl benzyl sulfone compound 20

Compound 20

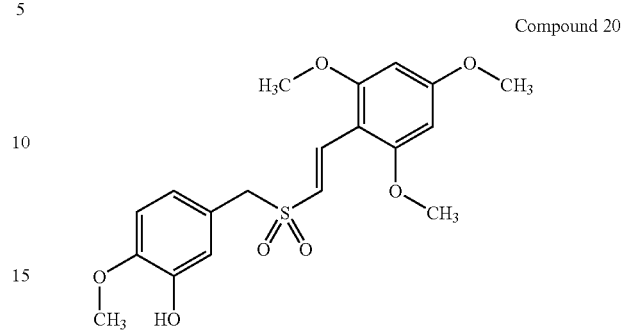

and (iii) converting compound 20 to compound 29 by using a phoshorylation process using phosphorous oxychloride, wherein the phoshphorylation process is performed according to Scheme 7 comprising:
(a) phosphorylating styryl benzyl sulfone compound 20

Compound 20

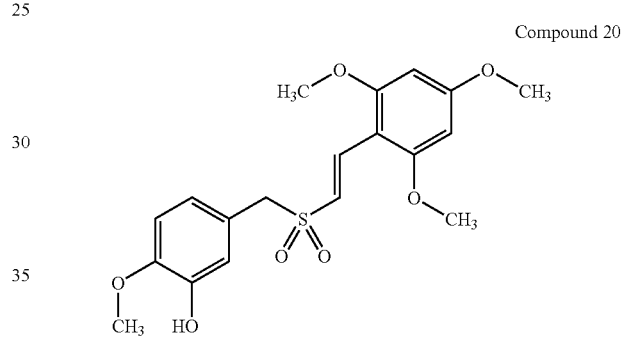

with phosphorous oxychloride under basic conditions using a neutralizing base to yield 3-O-dichloro phosphate of compound 20 that is free of impurities;
(b) treating 3-O-dichloro phosphate of compound 20 obtained in step (a) first with ice and then with aqueous potassium hydroxide and then treating with aqueous HCl to yield precipitate of the phosphoric acid derivative of compound 20 as a light yellow solid, compound 28; and
(c) treating compound 28, with an alkali in an organic solvent to yield alkali metal-O-phosphate, compound 29 at pH 8; and
(d) filtering and washing compound 29 with acetone and drying under vacuum to obtain a pure compound 29.

2. The process according to claim 1, wherein in step (a) the reaction is performed at a temperature of about 0° C.

3. The process according to claim 1, wherein in step (a) the phosphorylating agent is used in 4.3:1 proportion to phenol 20.

4. The process according to claim 1, wherein in step (c) the alkali comprises NaOH, KOH, or $NH_4OH$.

5. The process according to claim 1, wherein in step (c) the organic solvent comprises methanol, ethanol, propanol, or 2-propanol.

6. The process according to claim 1, wherein in step (a) the neutralizing base is used in 7:1 proportion to phenol 20.

7. The process according to claim 6, wherein the neutralizing base comprises triethylamine, N,N-diisopropylethyl amine, pyridine, and/or N,N-dimethylpyridine.

8. The process according to claim 6, wherein the neutralizing base is triethyl amine.

9. The process according to claim 1, wherein in step (b) the reaction sequences are performed at a temperature of about 0° C.

* * * * *

UNITED STATES PATENT AND TRADEMARK OFFICE
CERTIFICATE OF CORRECTION

PATENT NO.          : 8,735,620 B2
APPLICATION NO.     : 12/337121
DATED               : May 27, 2014
INVENTOR(S)         : Reddy Sirigireddy It is certified that error appears in the above-identified patent and that said Letters Patent is hereby corrected as shown below:

On the Title Page

On Page 1, Column 1, under the section of Assignee, please delete:

"EPR Pharmaceuticals, PVT. Ltd, Hyderabad (IN)"

and insert instead:

-- ONCONOVA THERAPEUTICS, INC. (NEWTOWN, PA) --

Signed and Sealed this
Fourth Day of November, 2014

Michelle K. Lee
*Deputy Director of the United States Patent and Trademark Office*